US011884985B2

(12) United States Patent
Perlin et al.

(10) Patent No.: US 11,884,985 B2
(45) Date of Patent: Jan. 30, 2024

(54) ASSAYS FOR FUNGAL INFECTION

(71) Applicant: Rutgers, The State University of New Jersey, New Brunswick, NJ (US)

(72) Inventors: David S. Perlin, New York, NY (US); Steven Park, Flushing, NY (US); David W. Denning, Cheshire (GB)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 38 days.

(21) Appl. No.: 17/647,610

(22) Filed: Jan. 11, 2022

(65) Prior Publication Data
US 2022/0136072 A1  May 5, 2022

Related U.S. Application Data

(62) Division of application No. 16/542,782, filed on Aug. 16, 2019, now Pat. No. 11,230,742, which is a division of application No. 15/600,882, filed on May 22, 2017, now Pat. No. 10,385,409, which is a division of application No. 12/447,606, filed as application No. PCT/US2007/023043 on Nov. 1, 2007, now Pat. No. 9,657,355.

(60) Provisional application No. 60/968,413, filed on Aug. 28, 2007, provisional application No. 60/864,146, filed on Nov. 2, 2006.

(30) Foreign Application Priority Data

Nov. 2, 2006  (GB) ..................................... 0621864
Aug. 28, 2007  (GB) ..................................... 0716687

(51) Int. Cl.
C12Q 1/6895 (2018.01)

(52) U.S. Cl.
CPC ....... *C12Q 1/6895* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 5,487,972 | A | 1/1996 | Gelfand et al. |
| 5,593,836 | A | 1/1997 | Niemiec et al. |
| 5,925,517 | A | 7/1999 | Tyagi et al. |
| 6,605,439 | B2 | 8/2003 | Einsele |
| 6,773,882 | B2 | 8/2004 | Hogan et al. |
| 2005/0009051 | A1* | 1/2005 | Han ............. C12Q 1/6895 435/6.13 |
| 2005/0227236 | A1 | 10/2005 | Forsberg et al. |

FOREIGN PATENT DOCUMENTS

| EP | 0979312 B1 | 3/2006 |
| WO | 1991019005 A1 | 12/1991 |
| WO | 2002036813 A2 | 5/2002 |
| WO | 2002079512 A2 | 10/2002 |
| WO | 2003027329 A1 | 4/2003 |

OTHER PUBLICATIONS

Diffenbach (PCR methods and Applications (1993) vol. 3, pp. S30-S37) (Year: 1993).*
Roux et al(PCR Methods and Applications (1995) vol. 4, pp. s185-s194). (Year: 1995).*
AF461784 (NCBI Website Feb. 12, 2002).
AF402685 (NCBI website Dec. 23, 2003).
Afonia et al., "Minor Groove Binder-Conjugated DNA Probes for Quantitative DNA Detection by Hybridization-Triggered Fluorescence," Biotechniques (2002); 32(4):940-949.
Altschul et al., "Basic Local Alignment Search Tool," J. Mol. Biol., (1990), 215: 403-410.
Altschul, "A Protein Alignment Scoring System Sensititve at all Evolutionary Distances," J. Mol. Evol., (1993); 36:290-300.
Ausubel et al., Current Protocols in Molecular Blology, Chpt. 2, Green Publishing and Wiley-Interscience, NY 1995, 8 pages.
Booton et al., "Multiple group I introns detected in the nuclear small subunit rDNA of the autosporic green alga *Selenastrum capricornutum*", Current Genetics, 2004 vol. 46, p. 228-234.
Buchheidt et al., "Clinical Evaluation of a Polymerase Chain Reaction Assay to Detect *Aspergillus* Species in Bronchoalveolar Lavage Samples of Neutropenic Patients," British Journal of Haematology (2002); 116:803-811.
Burik et al., "Panfungal PCR Assay for Detection of Fungal Infection in Human BLood Specimens," Journal of Clinical Microbiology (May 1998); 36(5):1169-1175.
Cushion et al., (MBIO Mar. 2013 vol. 4 p. 1).
Devereux et al., "A Comprehensive Set of Sequence Analysis Programs for the VAX," Nucleic Acids Research (1984); 12:387-395.
Fredericks et al., "Comparision of Six DNA Extraction Methods for Recovery of Fungal DNA as Assessed by Quantitative PCR," J. Clin. Microbiol., (2005); 34(10):5122-5128.
Kappe et al., "Universal fungus-specific primer systems and group-specific hybridization oligonucleotides for 18S rDNA," Mycoses(Jan. 1, 1996); 39(1/02):25-30.
Makimura et al., "Specific Detection of *Aspergillus* and *Penicillium* Species from Respiratory Specimens by Polymerase Chain Reaction (PCR)," JP J. Med. Sci. Biol. (1994); 47:141-156.
NCBI Sequence BLASTsearch of Seq ID No. 14 Downloaded Mar. 8, 2021 (Year: 2021).

(Continued)

*Primary Examiner* — Katherine D Salmon
(74) *Attorney, Agent, or Firm* — FOX ROTHSCHILD LLP

(57) ABSTRACT

Methods and kits are described for testing for the presence or absence of any fungus in a sample. Examples of fungi that can be detected include, but are not limited to, those belonging to the genera *Candida*, *Aspergillus* and *Pneumocystis*. The methods include obtaining a sample suspected of containing fungal nucleic acid, including at least one universal region of fungal nucleic acid, and testing for the presence or absence in the sample of the at least one universal region of fungal nucleic acid. Samples may be biological or non-biological.

2 Claims, 22 Drawing Sheets

Specification includes a Sequence Listing.

(56) References Cited

OTHER PUBLICATIONS

NCBI Sequence BLAST search of Seq ID No. 17 Downloaded Mar. 8, 2021 (Year: 2021).
Ribes et al., "PCR Detectioin of Pneumocystis carinii in Bronchoalveolar Lavage Specimens: Analysis of Sensitivity and Specificity," Journal of Clinical Microbiology (Apr. 1997): 35(4):830-835.
S42926 (NCBI Wesbite May 8, 1993).
Sambrook et al., "Molecular Cloning: A Laoratory Manual," Molecular Cloning: a laboratory manual, 3rd Ed., Cold SPring Harbour Laboratory Press (2001), 67 pages.
Sandhu et al., "Laboratory Diagnosis of Pneumocystis carinii Infections by PCR Directed to Genes Encoding for Mitochondrial 5S and 28S Ribosomal RNA," Dian Microbiol Infect Dis (1999): 33:157-162.
Stetzenbach et al: "Detection and enumeration of airborne biocontaminants", Current Opinion in Biotechnology 2004, vol. 15, p. 170-174.
Tsolaki et al., "Pre-AIDS Era Isolates of *Pneumocystis carinii* f. sp. *hominis*: High Genotypic SImilarity with Contemporary Isolates," Journal of Clinical Microbiology (Jan. 1998); 36(1):90-93.
Tsolaki et al., "Oropharyngeal samples for genotyping and monitoring response to treatment in AIDS patients with Pneumocystis carinii pneumonia," J. Med. Microbiol. (1999); 28:897-905.
Ann E. Wakefield, "Pneumocystis carinii" British Medical Bulletin (2002): 61:175-188.
Wakefield et al., "Amplification of mitochondrial ribosomal RNA sequences from Pneumocystis carinii DNA of rat and human origin," Molecular and Biochemical Parasitology (1990); 43:69-76.
Whitcombe et al., "Detection of PCR Products Using Self-Probing Amplicons and Fluorescence," Nature Biotechnology (1994); 117:804-807.
Widjojoatmodjo et al., "Nucleic Acid Sequence-Based Amplification (NASBA) Detection of Medically important *Candida* Species," Journal of Microbiological Methods (1999); 38(1-2):81-90.
XP055328517 "Search of Amplicon of Seq ID 1-8 No. 2 and 3 Primers against Human Datase", (Nov. 1, 2006) retrieved from Internet: http://ibis/exam/jobresult?id=424420—retrieved on Dec. 13, 2016.
XP055328485, "Neto Dias: EM-EST:BE079147," (Jan. 1, 2000)—retrieved from the internet—http://ibis/exam/dbfetch.jsp?id-em_est:be079147.
XP055327314, "Database Search: Seq ID No. 1 against human database," (Jan. 1, 2001) pp. 53-71.
XP055328487 "Anonymous: EM_PAT:CQ710182," (Jan. 1, 2002)—retrieved from the internet: http://ibis/exam/dbfetch.jsp?id=em_pat:cq710182—retrieved on Dec. 23, 2016.

* cited by examiner

```
Ctrop (SEQ ID NO:22)  ACCTTAACGAGGAACAATTGGAGGGCAAGTCTGGTGCCAGCAGCCGCGGTAATTCCAGCT 597
Cpar  (SEQ ID NO:23)  ACCTTAACGAGGAACAATTGGAGGGCAAGTCTGGTGCCAGCAGCCGCGGTAATTCCAGCT 568
Cdub  (SEQ ID NO:24)  ACCTTAACGAGGAACAATTGGAGGGCAAGTCTGGTGCCAGCAGCCGCGGTAATTCCAGCT 583
Calb  (SEQ ID NO:25)  ACCTTAACGAGGAACAATTGGAGGGCAAGTCTGGTGCCAGCAGCCGCGGTAATTCCAGCT 586
Cguil (SEQ ID NO:26)  ACCTTAACGAGGAACAATTGGAGGGCAAGTCTGGTGCCAGCAGCCGCGGTAATTCCAGCT 591
Clus  (SEQ ID NO:27)  ACCTTAACGAGGAACAATTGGAGGGCAAGTCTGGTGCCAGCAGCCGCGGTAATTCCAGCT 575
Cgla  (SEQ ID NO:28)  ACCTTAACGAGGAACAATTGGAGGGCAAGTCTGGTGCCAGCAGCCGCGGTAATTCCAGCT 588
Ckru  (SEQ ID NO:29)  ACCTTAACGAGGAACAATTGGAGGGCAAGTCTGGTGCCAGCAGCCGCGGTAATTCCAGCT 558
                     ************************************************************

Ctrop   CCAAAAGCGTATATTAAAGTTGTTGCAGTTAAAAAGCTTCGTAGTTGAACCTTGGGCTTG 657
Cpar    CCAAAAGCGTATATTAAAGTTGTTGCAGTTAAAAAGCT-CGTAGTTGAACCTTGGGCTTG 627
Cdub    CCAAAAGCGTATATTAAAGTTGTTGCAGTTAAAAAGCT-CGTAGTTGAACCTTGGGCTTG 642
Calb    CCAAAAGCGTATATTAAAGTTGTTGCAGTTAAAAAGCT-CGTAGTTGAACCTTGGGCTTG 645
Cguil   CCAATAGCGTATATTAAAGTTGTTGCAGTTAAAAAGCT-CGTAGTTGAACTTTGGGCTTG 650
Clus    CCAAGAGCGTATATTAAAGTTGTTGCAGTTAAAAAGCT-CGTAGTTGAACCTTGGGAGCG 634
Cgla    CCAATAGCGTATATTAAAGTTGTTGCAGTTAAAAAGCT-CGTAGTTGAACTTTGGGCCTG 647
Ckru    CCAATAGCGTATATTAAAGTTGTTGCAGTTAAAAAGCT-CGTAGTTGAACTTGGGCCTG 617
        **** *********************************** ********** ****    *

Ctrop   GTTGGCCGGTCCATCTTTCTGATGCGTACTGGAACCCAACCGAAGCCTTTCCTTCTGGC 717
Cpar    GTTGGCCGGTCCATCTTTTTTGATGCGTACTGGA-CCCAGCCGA-GCCTTTCCTTCTGGC 685
Cdub    GCTGGCCGGTCC-ATCTTTTTGATGCGTA-TGGA-CCCAGCCGA-GCCTTTC-TTCTGGC 697
Calb    GCTGGCCGGTCC-ATCTTTTTGATGCGTACTGGA-CCCAGCCGA-GCCTTTCCTTCTGGC 702
Cguil   GTTGGCCGGTCC-GCCTTTTTGGCGAGTACTGGA-CCCAACCGA-GCCTTTCCTTCTGGC 707
Clus    CCGTGCCGGTCC----GCTTAGGCGAGCACTGGA-----GGCGGCGCCTCTTTCCCT--C 683
Cgla    GGTGGCCGGTCC---GATTTTTCGTGTACTGGAATGCACCGG-GCCTTTCCTTCTGG 703
Ckru    GGCGGACGGTCT---ACCTATGGTAAGCACTGTT--GCGGCCGG-GTCTTTCCTTCTGGC 671
        *  *****   *   *  *  ** *  * ** *     **  *

Ctrop   TAGCCTTTT---------------GGCGAACCCAGGACTTTACTTTGAAAAAATTAGA 761
Cpar    TAGCCTTTT---------------TGGCGAACCAGGACTTTACTTTGAAAAAATTAGA 729
Cdub    TAGCCATTTA--------------TGGCGAA-CCAGGACTTTACTTTGAAAAAATTAGA 742
Calb    TAGCCATTTA--------------TGGCGAA-CCAGGACTTTACTTTGAAAAAATTAGA 747
Cguil   TAACCATTCGCCCTTGTGGTGTT-TGGCGAA-CCAGGACTTTACTTTGAAAAAATTAGA 765
Clus    CTCCTCTTAG--------------CAATAAGAGGAGGACTGTTACTTTGAGTAAATGAGA 729
Cgla    TAACCCAAGTCGTGTGGCTTGGCGGCGAA-CCAGGACTTTACTTTGAAAAAATTAGA 762
Ckru    TAGCCCTCGG--------------GCGAA-CCAGGACGATTACTTTGAGGAAATTAGA 714
            *                           ****  ********  *** ***
```

FIG. 5A

```
Ctrop   GTGTTCAAAGCAGGCCTTT-GCTCGAATATATTAGCATGGAATAATAGAATAGGACGTTA 820
Cpar    GTGTTCAAAGCAGGCCTTT-GCTCGAATATATTAGCATGGAATAATAGAATAGGACGTTA 788
Cdub    GTGTTCAAAGCAGGCCTTT-GCTCGAATATATTAGCATGGAATAATAGAATAGGACGTTA 801
Calb    GTGTTCAAAGCAGGCCTTT-GCTCGAATATATTAGCATGGAATAATAGAATAGGACGTTA 806
Cguil   GTGTTCAAAGCAGGCCTTT-GCTCGAATATATTAGCATGGAATAATAGAATAGGACGTTA 824
Clus    GTGTTCAAAGCAGGCGCAC-GCTTGAATCTGTTAGCATGGAATAATAGAATAGGACGC-A 787
Cgla    GTGTTCAAAGCAGGCGTATTGCTCGAATATATTAGCATGGAATAATGGAATAGGACGTT- 821
Ckru    GTGTTCAAAGCAGGCCTTT-GCTCGGATATATTAGCATGGAATAATAGAATAGGACGC-A 772
        *********** ***   *** * ** * ***************** *********

Ctrop   TGGTTCTATTTTGTTGGTTTCTAGGACC-ATCGTAATGATTAATAGGGACCGGTCGGGGG 879
Cpar    TGGTTCTATTTTGTTGGTTTCTAGGACC-ATCGTAATGATTAATAGGGAC-GGTCGGGGG 846
Cdub    TGGTTCTATTTTGTTGGTTTCTAGGACC-ATCGTAATGATTAATAGGGAC-GGTCGGGGG 859
Calb    TGGTTCTATTTTGTTGGTTTCTAGGACC-ATCGTAATGATTAATAGGGAC-GGTCGGGGG 864
Cguil   TGGTTCTATTTTGTTGGTTTCTAGGACC-ATCGTAATGATTAATAGGGAC-GGTCGGGGG 882
Clus    TGGTTCTATTTTGTTGGTTTCTAGGACCCATCGTAATGATTAATAGGGAC-GGTCGGGGG 846
Cgla    TGGTTCTATTTTGTTGGTTTCTAGGACC-ATCGTAATGATTAATAGGGAC-GGTCGGGGG 879
Ckru    TGGTTCTATTTTGTTGGTTTCTAGGACC-ATCGTAATGATTAATAGGGAC-GGTCGGGGG 830
        **************************** ************************ ********

Ctrop   TATCAGTATTCAGTTGTCAGAGGTGAAATTCTTGGATTTACTGAAGACTAACTACTGCGA 939
Cpar    TATCAGTATTCAGTTGTCAGAGGTGAAATTCTTGGATTTACTGAAGACTAACTACTGCGA 906
Cdub    TATCAGTATTCAGTTGTCAGAGGTGAAATTCTTGGATTTACTGAAGACTAACTACTGCGA 919
Calb    TATCAGTATTCAGTTGTCAGAGGTGAAATTCTTGGATTTACTGAAGACTAACTACTGCGA 924
Cguil   CATCAGTATTCAGTTGTCAGAGGTGAAATTCTTAGATTTACTGAAGACTAACTACTGCGA 942
Clus    CATCAGTATTCAGTTGTCAGAGGTGAAATTCTTGGATTTACTGAAGACTAACTACTGCGA 906
Cgla    CATCAGTATTCAATTGTCAGAGGTGAAATTCTTGGATTTATTGAAGACTAACTACTGCGA 939
Ckru    CATCAGTATTCAGTCGTCAGAGGTGAAATTCTTGGATTGACTGAAGACTAACTACTGCGA 890
        ********** * ****************** * **** ****************
```

FIG. 5B

```
Ctrop     AAAGCATTTACCAAGGACGTTTTGCATTAATCAAGAACGAAAGTTAGGGGATCGAAGATG 999
Cpar      AA-GCATTTACCAAGGACGTTTT-CATTAATCAAGAACGAAAGTTAGGGGATCGAAGATG 964
Cdub      AA-GCATTTACCAAGGACGTTTT-CATTAATCAAGAACGAAAGTTAGGGGATCGAAGATG 977
Calb      AA-GCATTTACCAAGGACGTTTT-CATTAATCAAGAACGAAAGTTAGGGGATCGAAGATG 982
Cguil        AA-GCATTTGCCAAGGACGTTTT-CATTAATCAAGAACGAAAGTTAGGGGATCGAAGATG
1000
Clus      AA-GCATTTGCCAAGGACGTTTT-CATTAATCAAGAACGAAAGTTAGGGGATCGAAGATG 964
Cgla      AA-GCATTTGCCAAGGACGTTTT-CATTAATCAAGAACGAAAGTTAGGGGATCGAAGATG 997
Ckru      AA-GCATTTGCCAAGGACGTTTT-CATTAATCAAGAACGAAAGTTAGGGGATCGAAGATG 948
          ** ****** ************* ************************************

Ctrop     ATCAGATACCGTCGTAGTCTTAACC-ATAAACTATGCCGACTAGGGATCGGTTGTTGTTC
1058
Cpar      ATCAGATACCGTCGTAGTCTTAACC-ATAAACTATGCCGACTAGGGATCGGTTGTTGTTC
1023
Cdub      ATCAGATACCGTCGTAGTCTTAACC-ATAAACTATGCCGACTAGGGATCGGTTGTTGTTC
1036
Calb      ATCAGATACCGTCGTAGTCTTAACC-ATAAACTATGCCGACTAGGGATCGGTTGTTGTTC
1041
Cguil     ATCAGATACCGTCGTAGTCTTAACCCATAAACTATGCCGACTAGGGATCGGTGTGTTGTTC
1060
Clus      ATCAGATACCGTCGTAGTCTTAACC-ATAAACTATGCCGACTAGGGATCGGCGGCGTTC
1023
Cgla      ATCAGATACCGTCGTAGTCTTAACC-ATAAACTATGCCGACTAGGGATCGGGTGGTGTTT
1056
Ckru      ATCAGATACCGTCGTAGTCTTAACC-ATAAACTATGCCGACTAGGGATCGGTGGTGCTA
1007
          ************************* ************************** * * *
```

FIG. 5C

MYCONOSTICA PANEL
PAN CANDIDA (HEX)
PAN ASPERGILLUS (FAM)
PAN FUNGAL v.2.3 (Cy5)
INTERNAL CONTROL (TR)

MYCONOSTICA PANEL
PAN CANDIDA (HEX)
PAN ASPERGILLUS (FAM)
PAN FUNGAL v.3.3 (Cy5)
INTERNAL CONTROL (TR)

ASSAYS FOR FUNGAL INFECTION

INFORMATION ON RELATED APPLICATIONS

The present application is a Divisional of U.S. patent application Ser. No. 16/542,782, filed Aug. 16, 2019, which will issue as U.S. patent Ser. No. 11/230,742 on Jan. 25, 2022, which is a Divisional of U.S. patent application Ser. No. 15/600,882, filed May 22, 2017, now U.S. Pat. No. 10,385,409, which is a Divisional of U.S. patent application Ser. No. 12/447,606, filed May 12, 2010, now U.S. Pat. No. 9,657,355, which is the U.S. National Phase of International Patent Application No. PCT/US2007/023043, filed Nov. 1, 2007, which claims priority to U.S. Provisional Application No. 60/968,413, filed Aug. 28, 2007, and to U.S. Provisional Application No. 60/864,146, filed Nov. 2, 2006, and to UK Patent Application No. 0716687.9, filed Aug. 28, 2007, and to UK Patent Application No. 0621864.8, filed Nov. 2, 2006, all of which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jan. 10, 2022, is named 096747.00457_ST25.txt and is 17.4 kilobytes in size.

FIELD OF THE INVENTION

The invention relates to detecting fungi in a sample. In particular, the invention relates to the rapid detection of any fungus in a sample and the rapid detection of a particular genus or species of fungus in a sample. The invention also generally relates to fungal identification. Methods and kits are also provided for testing for the presence or absence of a fungus in a sample. Examples of fungi detected include, but are not limited to, those belonging to the genera *Candida, Aspergillus* and *Pneumocystis*.

BACKGROUND OF THE INVENTION

Fungal infections are a significant cause of morbidity and mortality in a variety of severely ill patients. For instance, fungi are able to cause superficial and often fatal disseminated infections in immunocompromised patients. Systemic fungal infections cause approximately 25% of infection-related deaths in leukaemics and 5-10% of deaths in patients undergoing lung, pancreas or liver transplantation. Acquired fungal sepsis is also known to occur in up to 13% of very low birth-weight infants.

Members of the *Candida* genus are responsible for most of the fungal infections in humans. They are the fourth most common cause of nosocomial bloodstream infections. However, other fungal species are also responsible for infections in humans. The members of the *Aspergillus* genus are the second most common cause of fungal infections behind the members of the *Candida* genus. However, other genera, including *Malassezia, Trichosporon, Fusarium, Acremonium, Rhizopus, Mucor* and *Absidia*, can be responsible for disseminated infections in humans.

The impact of a fungal infection is often exacerbated by a failure to rapidly diagnose and effectively treat the infection. Numerous studies have shown that a delay in appropriate therapy is associated with increased morbidity and mortality. At present, clinical methods of detecting the presence of a fungus in a patient are unreliable and time consuming. For instance, the detection of fungal infections is usually carried out by blood culture, which takes up to 1 to 2 days to perform and often provides false negative results. In addition, some fungi, such as members of the *Pneumocystis* genus, cannot be cultured easily.

The lack of rapid diagnostic tests for particular fungal species is one of the major impediments to successful management of infected patients. Different species of fungus, even in the same genus, vary in their susceptibilities to the common anti-fungal agents. Some species even display resistance to some agents. The identification of the specific fungal species causing an infection can be even more time consuming that simply detecting the presence of a fungus and this can often further delay effective treatment of the infection.

It is also important that various non-biological samples, such as surgical fluids and drinking water, are known to be fungus free. However, there is currently a lack of rapid tests for the presence of a fungus or for particular fungal genera or species in non-biological samples.

SUMMARY OF THE INVENTION

The inventors have shown that the presence or absence of any fungus in a sample can be rapidly and reliably determined using DNA analysis. This is referred to herein as panfungal detection. In particular, the inventors have shown for the first time that panfungal detection can be carried out on non-biological samples. The inventors have also identified a novel region of fungal DNA that can be used for panfungal detection.

The inventors have also identified novel regions of DNA that are specific to fungi belonging to the genera *Candida, Aspergillus* and *Pneumocystis* and can therefore be used to detected fungi belonging to each of these genera. The inventors have further developed novel probes and primers that can be used to detect these regions either individually or simultaneously in a multiplex reaction.

The inventors have also developed novel primers and probes for the rapid detection of fungi belonging to the species *Candida tropicalis, Candida parapsilosis, Candida albicans, Candida glabrata* and *Candida krusei*. This allows all of these species to be identified simultaneously in a multiplex reaction using only one pair of primers. The inventors have also developed a new internal PCR amplification control.

The invention therefore concerns the rapid detection of any fungus in a sample. The invention also concerns the rapid detection of fungi of the genus *Candida, Aspergillus* or *Pneumocystis* in a sample. The invention further concerns the rapid detection of fungi of the species *Candida tropicalis, Candida parapsilosis, Candida albicans, Candida glabrata* or *Candida krusei* in a sample. The invention means that DNA analysis can be used to rapidly and reliably determine the presence of or the genus or species of a fungus in a sample. Accordingly, the invention provides a method for the rapid detection of the presence or absence of any fungus in a sample, comprising detecting the presence or absence in the sample of at least one universal region of fungal DNA. The invention further provides:

a method for the rapid detection of the presence or absence of a fungus belonging to the genus *Candida* in a sample, comprising detecting the presence or absence in the sample of a region of fungal DNA that shares at least 80% homology with SEQ ID NO: 5;

a method for the rapid detection of the presence or absence of a fungus belonging to the genus *Aspergillus* in a sample, comprising detecting the presence or absence in the sample of a region of fungal DNA that shares at least 80% homology with SEQ ID NO: 14;

a method for the rapid detection of the presence or absence of a fungus belonging to the genus *Pneumocystis* in a sample obtained from a human, comprising detecting the presence or absence in the sample of a region of fungal DNA that shares at least 80% homology with SEQ ID NO: 18;

a method for the rapid detection of the presence or absence of a fungus belonging to the species *Candida tropicalis* in a sample, comprising detecting the presence or absence in the sample of a region of fungal DNA as shown in SEQ ID NO: 30 using the molecular beacon probe shown in SEQ ID NO: 33;

a method for the rapid detection of the presence or absence of a fungus belonging to the species *Candida parapsilosis* in a sample, comprising detecting the presence or absence in the sample of a region of fungal DNA as shown in SEQ ID NO: 34 using the molecular beacon probe shown in SEQ ID NO: 35;

a method for the rapid detection of the presence or absence of a fungus belonging to the species *Candida albicans* in a sample, comprising detecting the presence or absence in the sample of a region of fungal DNA as shown in SEQ ID NO: 36 using the molecular beacon probe shown in SEQ ID NO: 37;

a method for the rapid detection of the presence or absence of a fungus belonging to the species *Candida glabrata* in a sample, comprising detecting the presence or absence in the sample of a region of fungal DNA as shown in SEQ ID NO: 38 using the molecular beacon probe shown in SEQ ID NO: 39;

a method for the rapid detection of the presence or absence of a fungus belonging to the species *Candida krusei* in a sample, comprising detecting the presence or absence in the sample of a region of fungal DNA as shown in SEQ ID NO: 40 using the molecular beacon probe shown in SEQ ID NO: 43;

a kit for the rapid detection of the presence or absence of any fungus in a sample, comprising the molecular beacon probe as shown in SEQ ID NO: 4 and the primers shown in SEQ ID NOs: 2 and 3;

a kit for the rapid detection of the presence or absence of any fungus in a sample, comprising (a) the molecular beacon probe as shown in SEQ ID NO: 44; (b) one or both of the sense primers shown in SEQ ID NOs: 48 and 50; and (b) one or both of the antisense primers shown in SEQ ID NOs: 49 and 51;

a kit for the rapid detection of the presence or absence of any fungus in a sample, comprising (a) the molecular beacon probe as shown in SEQ ID NO: 45; (b) one or both of the sense primers shown in SEQ ID NOs: 48 and 50; and (b) one or both of the antisense primers shown in SEQ ID NOs: 49 and 51;

a kit for the rapid detection of the presence or absence of a fungus belonging to the genus *Candida* in a sample, comprising the molecular beacon probe shown in SEQ ID NO: 8 and the primers shown in SEQ ID NOs: 6 and 7;

a kit for the rapid detection of the presence or absence of a fungus belonging to the genus *Aspergillus* in a sample, comprising the molecular beacon probe shown in SEQ ID NO: 17 and the primers shown in (a) SEQ ID NOs: 15 and 16 or (b) SEQ ID NOs: 46 and 47; a kit for the rapid detection of the presence or absence of a fungus belonging to the genus *Pneumocystis* in a sample obtained from a human, comprising the molecular beacon probe shown in SEQ ID NO: 21 and the primers shown in SEQ ID NOs: 19 and 20; and a kit for the rapid detection of the presence or absence of a fungus belonging to a particular species of *Candida* in a sample, comprising the primers shown in SEQ ID NOs: 31 and 32 or 41 and 42 and one or more of the molecular beacon probes shown in SEQ ID NOs 33, 35, 37, 39 and 43.

In one aspect, methods are provided for testing for the presence or absence of any fungus in a sample, comprising obtaining a sample suspected of containing fungal nucleic acid, including at least one universal region of fungal nucleic acid, and testing for the presence or absence in the sample of the at least one universal region of fungal nucleic acid. In some embodiments, the nucleic acid comprises DNA, and in other embodiments, the nucleic acid comprises RNA. Samples may be obtained from a wide variety of biological and/or non-biological sources.

In some embodied methods the testing step includes contacting the sample with an oligonucleotide probe comprising a nucleic acid capable of hybridizing to the at least one universal region of fungal nucleic acid under stringent conditions. The testing step may also include contacting the sample with an oligonucleotide probe comprising a nucleic acid capable of hybridizing to the at least one universal region of fungal nucleic acid under non-stringent conditions. In some embodiments, the methods further comprise amplifying the at least one universal region of fungal nucleic acid. In methods in which the universal region of the fungal nucleic acid is amplified, the amplifying step may be carried out in the presence of one or more internal PCR amplification controls to ensure appropriate amplification of any fungal nucleic acid present in the sample. In such methods the one or more internal PCR amplification controls may comprise a non-fungal sequence.

In another aspect, methods of testing for the presence or absence of a fungus belonging to a genus such as *Candida*, *Aspergillus*, or *Pneumocystis* in a sample are provided. Such methods may comprising obtaining a sample suspected of containing fungal nucleic acid, including at least one region of fungal nucleic acid characteristic of the genus of interest, and testing for the presence or absence in the sample of the at least one region of fungal nucleic acid characteristic of the that genus. The testing step may include contacting the sample with a probe. Such methods may further comprise amplifying the at least one region of fungal nucleic acid characteristic of the genus by contacting the sample with a pair of primers.

In yet another aspect, methods of testing for the presence or absence of a fungus belonging to species such as *Candida tropicalis, Candida parapsilosis, Candida albicans, Candida glabrata,* and/or *Candida krusei* in a sample are provided. Such methods may comprise, obtaining a sample suspected of containing fungal nucleic acid, including at least one region of fungal nucleic acid characteristic of the species of interest, and testing for the presence or absence in the sample of the at least one region of fungal nucleic acid characteristic of the that species. In the above embodied methods in which the fungus belongs to a *Candida* species, the methods may further comprise amplifying the at least one region of fungal nucleic acid characteristic of the *Candida* species by contacting the sample with a pair of primers.

In another aspect, testing kits are provided for a number of fungal nucleic acids. In some embodiments, a panfungal nucleic acid testing kits are provided. In other embodiments, kits are provided for testing for the presence or absence of at least one region of a fungal nucleic acid characteristic of the genus *Aspergillus,* of the genus *Pneumocystis,* or of a species of *Candida* in a sample. In another example, kits are provided for simultaneously detecting panfungal, pan*Candida* and pan*Aspergillus* targets. Other kits comprise reagents for detecting pan*Aspergillus* targets and *Pneuomcytis jirovecii.* Such kits may further comprise one or more internal PCR amplification controls.

DESCRIPTION OF THE FIGURES

FIGS. 5A, 5B and 5C show a sequence alignment between the 18S region of various members of the *Candida* genus. Ctrop is *Candida tropicalis.* Cpar is *Candida parapsilosis.* Cdub is *Candida dubliniensis.* Calb is *Candida albicans.* Cguil is *Candida guilliermondii.* Clus is *Candida lusitaniae.* Cgla is *Candida glabrata.* Ckru is *Candida krusei.* The shaded boxes that span all 8 sequences indicate the regions that were used in the Examples to design primers that amplify part of the 18S region of all eight of these *Candida* species. The primers corresponding to these regions are shown in Table 1 as SEQ ID NOs: 31 (forward) and (reverse) 32. The non-shaded boxes on the sequence for *Candida krusei* correspond to different regions that can be used to design primers that amplify part of the 18S region for this species. The primers corresponding to these regions are shown in Table 1 as SEQ ID NOs: 41 (forward) and 42 (reverse). The shaded boxes that only span the sequence of one species indicate regions that are specific for the particular species of *Candida.* These regions (SEQ ID NOs: 30, 34, 36, 38 and 40) can be used to design species-specific probes. The molecular beacon probes used to detect the different species-specific regions are shown in Table 1 as SEQ ID NOs: 33, 35, 37, 39 and 43.

DESCRIPTION OF THE SEQUENCES

Figure 1:
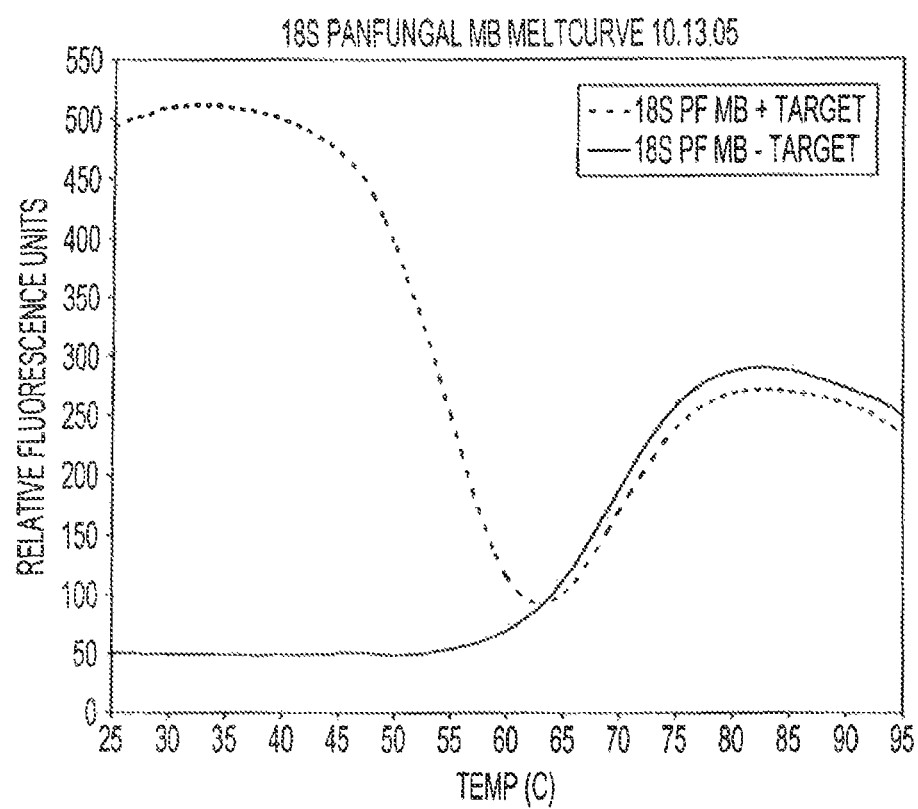
FIG. 1 shows a plot of the fluorescence released from the panfungal molecular beacon (Table 1, Ib; SEQ ID NO: 4) as the temperature is increased in the presence or absence of the target (melting curve). The dotted line shows the results with the target. The continuous line shows the results without the target.

SEQ ID NO: 1 shows the panfungal sequence that is detected in Examples 1 to 4.

SEQ ID NOs: 2 and 3 show the panfungal oligonucleotide primers used in Examples 1 to 4.

SEQ ID NO: 4 shows the panfungal molecular beacon probe used in Examples 1 to 4.

SEQ ID NO: 5 shows the *Candida*-specific sequence that is detected in Example 3.

SEQ ID NOs: 6 and 7 show the *Candida* oligonucleotide primers used in Example 3.

SEQ ID NO: 8 shows the *Candida* molecular beacon probe used in Example 3.

SEQ ID NO: 9 shows the sequence of the portion of the Maize (Zea mays) tRNA-LEU intron region used as an internal control in the Examples.

SEQ ID NO: 10 shows the sequence within SEQ ID NO: 9 that is detected as part of the internal control in the Examples.

SEQ ID NOs: 11 and 12 show the oligonucleotide primers used as part of the internal control in the Examples.

SEQ ID NO: 13 shows the molecular beacon probe used to detect SEQ ID NO 10 as part of the internal control in the Examples.

SEQ ID NO: 14 shows the *Aspergillus*-specific sequence that is detected in Examples 3 and 4.

SEQ ID NOs: 15 and 16 show the *Aspergillus* oligonucleotide primers used in Examples 3 and 4.

SEQ ID NO: 17 shows the *Aspergillus* molecular beacon probe used in Examples 3 and 4.

SEQ ID NO: 18 shows the *Pneumocystis*-specific sequence that is detected in Example 4.

SEQ ID NOs: 19 and 20 show the *Pneumocystis* oligonucleotide primers used in Example 4.

SEQ ID NO: 21 shows the *Pneumocystis* molecular beacon probe used in Example 4.

SEQ ID NO: 22 shows the sequence of 18S in *Candida tropicalis.*

SEQ ID NO: 23 shows the sequence of 18S in *Candida parapsilosis.*

SEQ ID NO: 24 shows the sequence of 18S in *Candida dubliniensis.*

SEQ ID NO: 25 shows the sequence of 18S in *Candida albicans.*

SEQ ID NO: 26 shows the sequence of 18S in *Candida guilliermondii.*

SEQ ID NO: 27 shows the sequence of 18S in *Candida lusitaniae.*

SEQ ID NO: 28 shows the sequence of 18S in *Candida glabrata.*

SEQ ID NO: 29 shows the sequence of 18S in *Candida krusei.*

SEQ ID NO: 30 shows the *Candida tropicalis*-specific sequence that is detected in Example 6.

SEQ ID NO: 31 shows the sequence of the forward primer that is used in Example 6 to amplify part of the 18S region for all five *Candida* species.

SEQ ID NO: 32 shows the sequence of the reverse primer that is used in Example 6 to amplify part of the 18S region for all five *Candida* species.

SEQ ID NO: 33 shows the sequence of the molecular beacon probe that is used in Example 6 to specifically detect *Candida tropicalis*.

SEQ ID NO: 34 shows the *Candida parapsilosis*-specific sequence that is detected in Example 6.

SEQ ID NO: 35 shows the sequence of the molecular beacon probe that is used in Example 6 to specifically detect *Candida parapsilosis*.

SEQ ID NO: 36 shows the *Candida albicans*-specific sequence that is detected in Example 6.

SEQ ID NO: 37 shows the sequence of the molecular beacon probe that is used in Example 6 to specifically detect *Candida albicans*.

SEQ ID NO: 38 shows the *Candida glabrata*-specific sequence that is detected in Example 6.

SEQ ID NO: 39 the sequence of the molecular beacon probe that is used in Example 6 to specifically detect *Candida glabrata*.

SEQ ID NO: 40 shows the *Candida &mse/*-specific sequence that is detected in Example 6.

SEQ ID NO: 41 shows the sequence of the forward primer that can be used to amplify part of the 18S region for all five species of *Candida*.

SEQ ID NO: 42 shows the sequence of the reverse primer that can be used to amplify part of the 18S region for all five species of *Candida*.

SEQ ID NO: 43 shows the sequence of the molecular beacon probe that is used in Example 6 to specifically detect *Candida krusei*.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a method" includes "methods", reference to "a probe" includes two or more such probes, reference to "a label" includes two or more such labels, reference to "fungus" includes two or more fungi, and the like.

All publications, patents and patent applications cited herein, whether supra or infra, are hereby incorporated by reference in their entirety.

The invention generally concerns the rapid detection and identification of a fungus or more than one fungus in a sample. The invention allows the rapid detection of any fungus in a sample (panfungal detection). The invention in a preferred embodiment allows the rapid detection and identification of a fungus belonging to the genus *Candida, Aspergillus* or *Pneumocystis*. In still another preferred embodiment of the invention, a method is provided for the rapid detection and identification of a fungus belonging to the species *Candida tropicalis, Candida parapsilosis, Candida albicans, Candida glabrata* or *Candida krusei*.

A Description of Selected Embodiments of the Invention

In one aspect, a method of testing for the presence or absence of any fungus in a sample is provided, comprising obtaining a sample suspected of containing fungal nucleic acid, including at least one universal region of fungal nucleic acid, and testing for the presence or absence in the sample of the at least one universal region of fungal nucleic acid. In some embodiments, the nucleic acid comprises DNA, and in other embodiments, the nucleic acid comprises RNA.

Samples may be obtained from biological or non-biological sources. For example the biological source samples can include, but are not limited to, a biological fluid, tissue, or a combination of any two or more thereof. Non-biological sources may include, but are not limited to samples obtained from the environment. For example, some non-biological sources may include an air sample, a water sample, a soil sample, or combinations thereof. Non-biological sources may also include a piece of a vehicle, watercraft, aircraft, building, or dwelling.

In some embodied methods, the at least one universal region of fungal nucleic acid includes SEQ ID NO: 1, a complement or a transcript thereof, or a sequence having 80% or more sequence homology with SEQ ID NO: 1, the complement or the transcript thereof. In other embodiments, the at least one universal region of fungal nucleic acid includes SEQ ID NO: 1, a complement or a transcript thereof, or a sequence having 90% or more sequence homology with SEQ ID NO: 1, complement or transcript thereof.

In some embodied methods the testing step includes contacting the sample with an oligonucleotide probe comprising a nucleic acid capable of hybridizing to the at least one universal region of fungal nucleic acid under stringent conditions. The testing step may also include contacting the sample with an oligonucleotide probe comprising a nucleic acid capable of hybridizing to the at least one universal region of fungal nucleic acid under non-stringent conditions. In such methods, the oligonucleotide probe may further include a detectable label. In other such methods, the probe includes SEQ ID NO: 4, complement or transcript thereof, or a sequence having 90% or more sequence homology with SEQ ID NO: 4, complement or transcript thereof.

Methods embodied herein may further comprise amplifying the at least one universal region of fungal nucleic acid. For example, the amplifying step may include contacting the sample with a pair of primers such as, but not limited to, SEQ ID NO: 2 and SEQ ID NO: 3.

In methods in which the universal region of the fungal nucleic acid is amplified, the amplifying step may be carried out in the presence of one or more internal PCR amplification controls to ensure appropriate amplification of any fungal nucleic acid present in the sample. In such methods the one or more internal PCR amplification controls may comprise a non-fungal sequence. In other such methods, the amplifying step may be carried out in the presence of a cloned or synthesized tRNA-LEU intron region, which is added to the amplification mixture in a predetermined amount to rule out the presence of inhibitors or other defective amplification steps. tRNA-LEU intron regions used in the embodied methods may comprise a portion of the Maize (*Zea mays*) tRNA-LEU intron region, for example, including but not limited to, SEQ ID NO: 9. In some such embodied methods, the method further comprises detecting the presence of a nucleic acid including SEQ ID NO: 10. In other such embodied methods, the detecting step comprises contacting the sample with a pair of oligonucleotides primers including SEQ ID NO: 11 and SEQ ID NO: 12 and a molecular beacon probe including SEQ ID NO: 13.

In another aspect, a method is provided for testing for the presence or absence of a fungus belonging to the genus *Candida* in a sample. Such methods comprise obtaining a sample suspected of containing fungal nucleic acid, including at least one region of fungal nucleic acid characteristic of the genus *Candida,* and testing for the presence or absence in the sample of the at least one region of fungal nucleic acid characteristic of the genus *Candida.* In some embodiments, the at least one region of fungal nucleic acid characteristic of the genus *Candida* includes SEQ ID NO: 5, a complement or transcript thereof, or a sequence having 80% or more sequence homology with SEQ ID NO: 5, complement or transcript thereof.

In other embodiments, the testing step includes contacting the sample with a probe including SEQ ID NO: 8. In some such embodiments the methods further comprise amplifying the at least one region of fungal nucleic acid characteristic of the genus *Candida* by contacting the sample with a pair of primers including SEQ ID NO: 6 and SEQ ID NO: 7.

In another aspect, a method of testing for the presence or absence of a fungus belonging to the genus *Aspergillus* in a sample is provided, comprising obtaining a sample suspected of containing fungal nucleic acid, including at least one region of fungal nucleic acid characteristic of the genus *Aspergillus,* and testing for the presence or absence in the sample of the at least one region of fungal nucleic acid characteristic of the genus *Aspergillus.*

In some embodiments, the at least one region of fungal nucleic acid characteristic of the genus *Aspergillus* includes SEQ ID NO: 14, a complement or transcript thereof, or a sequence having 80% or more sequence homology with SEQ ID NO: 14, complement or transcript thereof. In some such methods, the testing step includes contacting the sample with a probe including SEQ ID NO: 17. Such methods may further comprise amplifying the at least one region of fungal nucleic acid characteristic of the genus *Aspergillus* by contacting the sample with a pair of primers including SEQ ID NO: 15 and SEQ ID NO: 16.

In yet another aspect, a method of testing for the presence or absence of a fungus belonging to the genus *Pneumocystis* in a sample is provided, comprising obtaining a sample suspected of containing fungal nucleic acid, including at least one region of fungal nucleic acid characteristic of the genus *Pneumocystis,* and testing for the presence or absence in the sample of the at least one region of fungal nucleic acid characteristic of the genus *Pneumocystis.*

In some embodied methods, the at least one region of fungal nucleic acid characteristic of the genus *Pneumocystis* includes SEQ ID NO: 18, a complement or transcript thereof, or a sequence having 80% or more sequence homology with SEQ ID NO: 18, complement or transcript thereof. In some such methods, the testing step includes contacting the sample with a probe including SEQ ID NO: 21. Some such methods may further comprise amplifying the at least one region of fungal nucleic acid characteristic of the genus *Pneumocystis* by contacting the sample with a pair of primers including SEQ ID NO: 19 and SEQ ID NO: 20.

In yet another aspect, a method of testing for the presence or absence of a fungus belonging to the species *Candida tropicalis* in a sample is provided, comprising obtaining a sample suspected of containing fungal nucleic acid, including at least one region of fungal nucleic acid characteristic of the species *Candida tropicalis,* and testing for the presence or absence in the sample of the at least one region of fungal nucleic acid characteristic of the species *Candida tropicalis.* In some embodied methods, the at least one region of fungal nucleic acid characteristic of the species *Candida tropicalis* includes SEQ ID NO: 30, a complement or transcript thereof, or a sequence having 80% or more sequence homology with SEQ ID NO: 30, complement or transcript thereof. The testing step may include contacting the sample with a probe including SEQ ID NO: 33.

In yet another aspect, a method of testing for the presence or absence of a fungus belonging to the species *Candida parapsilosis* in a sample is provided, comprising obtaining a sample suspected of containing fungal nucleic acid, including at least one region of fungal nucleic acid characteristic of the species *Candida parapsilosis,* and testing for the presence or absence in the sample of the at least one region of fungal nucleic acid characteristic of the species *Candida parapsilosis.* In some embodied methods, the at least one region of fungal nucleic acid characteristic of the species *Candida parapsilosis* includes SEQ ID NO: 34, a complement or transcript thereof, or a sequence having 80% or more sequence homology with SEQ ID NO: 34, complement or transcript thereof. The some such methods, the testing step may include contacting the sample with a probe including SEQ ID NO: 35.

In yet another aspect, a method of testing for the presence or absence of a fungus belonging to the species *Candida albicans* in a sample, comprising obtaining a sample suspected of containing fungal nucleic acid, including at least one region of fungal nucleic acid characteristic of the species *Candida albicans,* and testing for the presence or absence in the sample of the at least one region of fungal nucleic acid characteristic of the species *Candida albicans.* In some embodied methods, the at least one region of fungal nucleic acid characteristic of the species *Candida albicans* includes SEQ ID NO: 36, a complement or transcript thereof, or a sequence having 80% or more sequence homology with SEQ ID NO: 36, complement or transcript thereof. In some such methods the testing step may include contacting the sample with a probe including SEQ ID NO: 37.

In another aspect, a method of testing for the presence or absence of a fungus belonging to the species *Candida glabrata* in a sample is provided, comprising obtaining a sample suspected of containing fungal nucleic acid, including at least one region of fungal nucleic acid characteristic of the species *Candida glabrata,* and testing for the presence or absence in the sample of the at least one region of fungal nucleic acid characteristic of the species *Candida glabrata.* In some embodied methods the at least one region of fungal nucleic acid characteristic of the species *Candida glabrata* includes SEQ ID NO: 38, a complement or transcript thereof, or a sequence having 80% or more sequence homology with SEQ ID NO: 38, complement or transcript thereof. In some such methods the testing step may include contacting the sample with a probe including SEQ ID NO: 39.

In yet another aspect, a method of testing for the presence or absence of a fungus belonging to the species *Candida krusei* in a sample is provided, comprising obtaining a sample suspected of containing fungal nucleic acid, including at least one region of fungal nucleic acid characteristic of the species *Candida krusei,* and testing for the presence or absence in the sample of the at least one region of fungal nucleic acid characteristic of the species *Candida krusei.* In some embodied methods, the at least one region of fungal nucleic acid characteristic of the species *Candida krusei* includes SEQ ID NO: 40, a complement or transcript thereof, or a sequence having 80% or more sequence homology with SEQ ID NO: 40, complement or transcript thereof. In such methods the testing step may include contacting the sample with a probe including SEQ ID NO: 43.

In the above embodied methods in which the fungus belongs to a *Candida* species, the methods may further comprise amplifying the at least one region of fungal nucleic acid characteristic of the *Candida* species by contacting the sample with a pair of primers including SEQ ID NO: 31, SEQ ID NO: 32, SEQ ID NO: 41, and SEQ ID NO: 42.

In other aspects, the inventive methods can be employed in multiplex reactions to simultaneously test for the presence or absence of a variety of fungi. One or more of the panfungal detection methods described below can be carried out simultaneously in a multiplex reaction with one or more of the genus detection methods described below and/or one of the species detection methods described below. Similarly, one or more of the genus detection methods described below can be carried out simultaneously in a multiplex reaction with one or more of the species detection methods described below. For example, the inventive methods can be used to simultaneously evaluate a sample for the presence of fungi generally, *Pneumocystis, Aspergillus*, as well as an internal control. In another example, the inventive methods can be used to simultaneously detect in a sample *Aspergillus* genus, *Pnemocystis jirovecii* and an internal control.

Testing kits are also provided for testing for a number of fungal nucleic acids. In some embodiments, a panfungal nucleic acid testing kit is provided comprising a molecular beacon probe including SEQ ID NO: 4 and a pair of primers including SEQ ID NO: 2 and SEQ ID NO: 3. In other embodiments, a kit for testing for the presence or absence of at least one region of fungal nucleic acid characteristic of the genus *Candida* in a sample is provided, comprising a molecular beacon probe including SEQ ID NO: 8 and a pair of primers including SEQ ID NO: 6 and SEQ ID NO: 7.

In yet other embodiments, a kit for testing for the presence or absence of at least one region of fungal nucleic acid characteristic of the genus *Aspergillus* in a sample is provided, comprising a molecular beacon probe including SEQ ID NO: 17 and a pair of primers including SEQ ID NO: 15 and SEQ ID NO: 16.

In yet other embodiments, a kit for testing for the presence or absence of at least one region of fungal nucleic acid characteristic of the genus *Pneumocystis* in a sample is provided, comprising a molecular beacon probe including SEQ ID NO: 21 and a pair of primers including SEQ ID NO: 19 and SEQ ID NO: 20.

In yet other embodiments, a kit for testing for the presence or absence of at least one region of fungal nucleic acid characteristic of a species of *Candida* in a sample is provided, comprising one or more molecular beacon probes including SEQ ID NO: 33, SEQ ID NO: 35, SEQ ID NO: 37, SEQ ID NO: 39, SEQ ID NO: 43, or combinations thereof and a pair of primers including SEQ ID NO: 31 and SEQ ID NO: 32, SEQ ID NO: 41 and SEQ ID NO: 42, or both pairs. Such kits may further comprise one or more internal PCR amplification controls.

Panfungal Detection Method

The invention provides a method for the rapid detection of the presence or absence of any fungus in a sample. This is referred to herein as the panfungal detection method. The panfungal detection method involves determining whether or not a sample comprises any fungus. The method therefore involves determining whether or not a sample comprises a fungus that belongs to any fungal phylum, any fungal genus or any fungal species. The method can be used in relation to any fungus. The fungus can belong to any of the five fungal phyla, Chytridiomycota, Zygomycota, Glomeromycota, Ascomycota or Basidiomycota. The fungus can be mould, yeast, smut or mushroom. The fungus is preferably a fungus that is capable of infecting humans or animals. The fungus can belong to any fungal genus. The fungus preferably belongs to the genus *Candida, Aspergillus, Pneumocystis, Cryptococcus, Blastomyces, Coccidioides, Paracoccidioides, Penicillium, Mucor, Scedosporium, Saccharomyces, Histoplasma, Fusarium, Paecilomyces, Trichosporon, Acremonium, Rhizopus, Rhizomucor, Mucor, Cuninghamella, Malezzesia, Blastoschizomyces, Scedosporium, Goetrichum, Trichophyton, Exophiala, Exserohilum, Fonsecea, Cladosporium, Curvularia, Basidiobolus Aureobasidium, Schizophyllum, Sporothrix, Scopulariopsis* or *Absidia*. The fungus can belong to any fungal species. The fungus can belong to any of the species exemplified below.

The panfungal detection method gives an indication of the fungus-containing status of the sample. The method indicates either that there is a fungus or fungi present in the sample or that there is no fungus present in the sample. The method allows the detection of a fungus in a sample without the need to test for a specific fungal genus or for a specific fungus species.

The panfungal detection method can be carried out on any sample. In one embodiment, the sample is a non-biological sample. Specific types of sample are discussed in more detail below. The panfungal detection method is typically carried out on a sample whose fungus-containing status is not known. In other words, the panfungal detection method is typically carried out when it is not known whether or not a sample contains a fungus. The panfungal detection method is preferably carried out on a sample that is suspected of containing a fungus. The method can be carried out on a sample that is known to contain a fungus to confirm the presence of the fungus.

The panfungal detection method comprises detecting the presence or absence in the sample of at least one universal region of fungal DNA. The presence of a universal region in the sample is indicative of the presence of a fungus in the sample. The absence of a universal region from the sample is indicative of the absence of a fungus from the sample. The method may involve detecting 1, 2, 3, 4, 5, 10, 15, 20 or more universal regions. A universal region of fungal DNA (hereinafter "universal region") is a region of DNA that is present in the genomes of all fungi. The universal region is not present in any other organism, particularly a microorganism such as a bacteria or a virus. For example, a universal region is region of DNA that is present in all fungi but that is not present in *Escherichia coli* and *Staphylococcus aureus*. A region of fungal DNA is a DNA sequence within the genome of a fungus. The region can be part of a gene, such as an intron, an exon or a part thereof. Alternatively, the region can incorporate a part of one or more genes.

The universal region is typically at least 5, at least 6, at least 7, at least 8, at least 9, at least 10, at least 15, at least 20, at least 25, at least 30, at least 35, at least 45, at least 50, at least 75 or at least 100 nucleotides in length. For example, the universal region can be from 5 to 200, from 7 to 100 or from 10 to 50 nucleotides in length. The region is preferably 5, 10, 15, 20, 25, 30, 35 or 40 nucleotides in length.

In one embodiment, only the universal region is detected. In another embodiment, the universal sequence is detected as part of larger sequence. For instance, the universal region can be detected as part of a sequence that has flanking sequences at the 5' end, the 3' end or at both the 5' and 3' ends of the universal region. The flanking sequences can be at least 1, at least 2, at least 5, at least 10, at least 15, at least 20, at least 25, at least 30, at least 35, at least 45, at least 50, at least 75 or at least 100 nucleotides in length. For example, the flanking regions can be from 1 to 100, from 5 to 50 or from 10 to 20 nucleotides in length.

The universal region is preferably part of the 18 S region.

The universal region is preferably a sequence that shares at least 80%, at least 85%, at least 90%, at least 95%, at least 98% or at least 99% homology or sequence identity with SEQ ID NO: 1. The universal region is even more preferably a sequence that is identical to SEQ ID NO: 1.

In another embodiment, the panfungal detection methods involve detecting the presence or absence in a sample of at least one universal region of fungal DNA present in at least the following fungi: *Gymnopus* spp., *Rhodocollybia butyracea*, *Hypholoma fasciculare*, *Saccharomyces cerevisiae*, *Tuber* spp., *Bothia castanella*, *Rhizosphere* spp., *Herpotrichiellaceae* spp., *Verrucariaceae* spp., *Marchandiomyces* spp., *Minimedusa* spp., *Marchandiobasidium aurantiacum*, *Marchandiomyces corallinus*, *Marchandiomyces lignicola*, *Burgoa* spp., *Athelia arachnoidea*, *Alternaria alternata*, *Alternaria* spp., *Boletus edulis*, *Leccinum aurantiacum*, *Trametes versicolor*, *Trametes* spp., *Sympodiomycopsis* spp., *Flavocetraria nivalis*, *Ampelomyces* spp., *Gymnopus biformis*, *Gymnopus* spp., *Gymnopus conβluens*, *Gymnopus spongiosus*, *Collybia readii*, *Marasmiellus stenophyllus*, *Marasmiellus ramealis*, *Marasmius scorodonius*, *Collybia marasmioides*, *Micromphale brassicolens*, *Caŋpia montagnei*, *Rhodocollybia* spp., *Anthracophyllum lateŋum*, *Anthracophyllum archeri*, *Anthracophyllum* spp., *Phanerochaete* spp., *Schizosaccharomyces pombe*, *Saccharomyces cerevisiae*, *Aspergillus fumigatus*, *Aspergillus flavus*, *Aspergillus niger*, *Aspergillus* spp., *Tricholoma imbricatum*, *Tricholoma βlavovirens*, *Tomentella sublilacina*, *Rhizopogon* spp., *Laccaria* spp., *Inocybe* spp., *Hebeloma* spp., *Cortinarius* spp., *Clavulina* spp., *Xerocomus* spp., *Amanita* spp., *Eurotium herbariorum*, *Edyuillia athecia*, *Warcupiella spinulosa*, *Hemicarpenteles paradoxus*, *Hemicarpenteles acanthosporus*, *Hemicarpenteles* spp., *Chaetosartorya cremea*, *Petromyces* spp., *Graphium tectonae*, *Diplolaimelloides* spp., *Rhabdolaimus* spp., *Hohenbuehelia petalodes*, *Glomerella graminicola*, *Cryptococcus arboriformis*, *Cryptococcus neoformans*, *Cryptococcus* spp., *Gamsylella parvicollis*, *Monacrosporium haptotylum*, *Monacrosporium sichuanense*, *Monacrosporium* Spp., *Monacrosporium gephyropagum*, *Monacrosporium* spp., *Drechslerella coelobrocha*, *Drechslerella dactyloides*, *Drechslerella* spp., *Arthrobotrys musiformis*, *Arthrobotrys flagrans*, *Arthrobotrys hertziana*, *Arthrobotrys oligospora*, *Arthrobotrys vermicola*, *Arthrobotrys* spp., *Monacrosporium drechsleri*, *Vermispora* spp., *Pseudallescheria boydii* (*Scedosporium apiospermum*), *Scedosporium inflatum*, *Geosmithia* spp., *Glomerella cingulata*, *Lophodermium piceae*, *Fusarium asiaticum*, *Fusarium* spp., *Pleurotus eryngii*, *Cintractia sorghi-vulgaris*, *Cantharocybe gruberi*, *Bourdotia* spp., *Auricularia* spp., *Puccinia bartholomaei*, *Puccinia* spp., *Diaporthe phaseolorum*, *Melanconis stilbostoma*, *Xylaria* spp., *Trichophyton equinum*, *Trichophyton tonsurans*, *Trichophytum violaceum*, *Trichophytum rubrum*, *Trichophytum interdigitale*, *Trichophytum schoenleinii* *Trichophyton* spp., *Chlorophyllum agaricoides*, *Cenococcum geophilum*, *Helotiales* spp., *Rhizoscyphus ericae*, *Lactarius pubescens*, *Lactarius* spp., *Piloderma fallax*, *Suillus luteus*, *Amanita muscaŋa*, *Tricholoma* spp., *Laccaria* cf. *bicolour*, *Cortinarius purpurascens*, *Seiridium* spp., *Apiospora montagnei*, *Chondrostereum purpureum*, *Botryobasidium subcoronatum*, *Boletellus shichianus*, *Boletellus* spp., *Hypocrea farinose*, *Hypocrea* spp., *Sarcostroma restionis*, *Sarcostroma* spp., *Truncatella betulae*, *Truncatella* spp., *Pestalotiopsis matildae*, *Paraconiothyrium* spp., *Phoma* spp., *Cunninghamella bainieri*, *Cunninghamella bertholletiae*, *Cantharellus cibarius*, *Apiospora bambusae*, *Apiospora* spp., *Discostroma botan*, *Cercophora caudate*, *Gnomonia ribicola*, *Faurelina elongate*, *Mycorrhiza fungi*, *Geomyces pannorum*, *Coprinus* spp., *Acremonium* spp., *Clones tachys* spp., *Phoma eupyrena*, *Tetracladium* spp., *Mortierella* spp., *Tulasnella calospora*, *Epulorhiza* spp., *Tulasnella calospora*, *Antarctomyces psychrotrophicus*, *Amphisphaeriaceae* spp., *Phomopsis* spp., *Trichoderma* spp., *Pestalotiopsis* spp., *Pestalotiopsis* spp., *Trichocomaceae* spp., *Coniochaetales* spp., *Tremellales* spp., *Dothideales* spp., *Phyllachoraceae* spp., *Saccharomycetales* spp., *Herpotrichiellaceae* spp., *Liliopsida* spp., *Trichosporonales* spp., *Trichosporon mycotoxinivorans*, *Trichosporon* spp., *Dothioraceae* spp., *Hypocreales* spp., *Mycosphaerellaceae* spp., *Sporidioholales* spp., *Clavicipitaceae* spp., *Pleosporales* spp., *Ustilaginaceae* spp., *Phyllachoraceae* spp., *Mucoraceae* spp., *Sordariales* spp., *Filobasidiales* spp., *Calosphaeriaceae* spp., *Clavicipitaceae* spp., *Mucor ales* spp., *Herpotrichiellaceae* spp., *Microdochium* spp., *Phyllachoraceae* spp., *Zopfiaceae* spp., *Botryosphaeriaceae* spp., *Helotiaceae* spp., *Bionectriaceae* spp., *Lachnocladiaceae* spp., *Dipodascaceae* spp., *Caulerpaceae* spp., *Micros tromatales* spp., *Aphyllophorales* spp., *Montagnulaceae* spp., *Gymnoascaceae* spp., *Cryphonectriaceae* spp., *Xylariales* spp., *Montagnulaceae* spp., *Chaetomiaceae* spp., *Xanthoria elegans*, *Rhizopus* spp., *Penicillium* spp., *Cetraria aculeate*, *Nephromopsis laureri*, *Tuckermannopsis chlorophylla*, *Cetraria ericetorum*, *Cetraria* spp., *Flavocetraria cucullata*, *Kaernefeltia merrillii*, *Amorosia littoralis*, *Quambalaria cyanescens*, *Cordyceps roseostromata*, *Cordyceps* spp., *Russula* spp., *Clavulina* spp., *Tuber quercicola*, *Gymnomyces* spp., *Tetrachaetum elegans*, *Anguillospora longissima*, *Hypocrea* spp., *Sirococcus conigenus*, *Rhizopogon roseolus*, *Rhizopogon olivaceotinctus*, *Rhizopogon* spp., *Pisolithus microcarpus*, *Rhizoscyphus ericae*, *Cortinarius glaucopus*, *Paxillus* spp., *Suillus variegates*, *Pyrobaculum aerophilum*, *Tulasnella* spp., *Hohenbuehelia* spp., *Cochliobolus lunatus*, *Plicaturopsis crispa*, *Bondarcevomyces taxi*, *Tapinella panuoides*, *Tapinella* spp., *Austropaxillus* spp., *Gomphidius roseus*, *Gyrodon lividus*, *Phylloporus pelletieri*, *Chamonixia caespitose*, *Porphyrellus porphyrosporus*, *Truncocolumella citrina*, *Tapinella atrotomentosa*, *Scleroderma leave*, *Suillus variegates*, *Suillus* spp., *Porphyrellus porphyrosporus*, *Pisolithus arrhizus*, *Phaeogyroporus portentosus*, *Melanogaster variegates*, *Leucogyrophana mollusca*, *Hydnomerulius pinastri*, *Gomphidius roseus*, *Gyrodon lividus*, *Gyroporus cyanescens*, *Chalciporus piperatus*, *Chamonixia caespitose*, *Bondarcevomyces taxi*, *Dendryphiella triticicola*, *Guignardia* spp., *Shiraia* spp., *Cladosporium* spp., *Phomopsis* spp., *Diaporthales* spp., *Pestalotiopsis* spp., *Lophiostoma* spp., *Verticillium chlamydosporium*, *Paecilomyces lilacinus*, *Paecilomyces varioti*, *Paecilomyces* spp., *Ceratorhiza oryzae-sativae*, *Geosmithia pallida*, *Geosmithia* spp., *Geosiphon pyriformis*, *Agonimia* spp., *Pyrgillus javanicus*, *Exophiala dermatitidis*, *Exophiala pisciphila*, *Exophiala* spp., *Ramichloridium anceps*, *Ramichloridium* spp., *Capronia pilosella*, *Isaria farinose*, *Pochonia suchlasporia*, *Lecanicillium psalliotae*, *Dothideomycete* spp., *Leotiomycete* spp., *Ustilaginoidea vixens*, *Hyphozyma lignicola*, *Coniochaeta malacotricha*, *Coniochaeta* spp., *Torrubiella confragosa*, *Isaria tenuipes*, *Microsporum canis*, *Microsporum audouinii*, *Microsporum* spp., *Epicoccum floccosum*, *Gigaspora* rosea, Gigaspora spp., Ganoderma spp., Pseudoperonospora cubensis, Hyaloperonospora parasitica, Plectophomella spp., Aureobasidium pullulans, Gloeophyllum sepiarium, Gloeophyllum spp., Donkioporia expansa, Antrodia sinuosa, Phaeoacremonium rubrigenum, Phaeoacremonium spp., Albertiniella polyporicola, Cephalotheca sulfurea, Fragosphaeria reniformis, Fragosphaeria spp., Phialemonium dimorphosporum, Phialemonium spp., Pichia norvegensis, Pichia spp., Candida albicans, Candida tropicalis, Candida glabrata, Candida par apsilosis, Candida spp., Gondwanamyces spp., Graphium spp., Ambrosiella spp., Microglossum spp., Neobulgaria pur a, Holwaya mucida, Chlorovibrissea spp., Chlorociboria spp., Thaxterogaster spp., Cortinaηus spp., Setchelliogaster spp., Timgrovea spp., Descomyces spp., Hymenogaster arenarius, Quadrispora tuber cularis, Quadrispora spp., Protoglossum violaceum, Ceratostomella pyrenaica, Ceratosphaeria lampadophora, Fonsecaea pedrosoi, Phlebia acerina, Phlebia spp., Pestalotiopsis disseminata, Paracoccidioides brasiliensis, Racospermyces koae, Endoraecium acaciae, Uromycladium tepperianum, Uromycladium spp., Agaricus bisporus, Agaricus spp., Psilocybe quebecensis, Psilocybe merdaria, Psilocybe spp., Gymnopilus luteofolius, Gymnopilus liquiritiae, Gymnopilus spp., Hypholoma tuberosum, Melanotus hartii, Panaeolus uliginosus, Stropharia rugosoannulata, Dermocybe semisanguinea, Dermocybe spp., Helicoma monilipes, Helicoma spp., Tubeufla helicomyces, Tubeufla spp., Leohumicola verrucosa, Leptosphaerulina chartarum, Macrophoma spp., Marssonina rosae, Botryotinia fuckeliana, Pestalotiopsis spp., Chrysosporium carmichaelii, Chrysosporium spp., Dactylella oxyspora, Dactylellina lobatum, Cucurbitaceae spp., Chrysophyllum spars iβlorum, Chrysophyllum spp., Blumeria graminis, Sawadaea polyβida, Sawadaea spp., Parauncinula septata, Erysiphe mori, Erysiphe spp., Typhulochaeta japonica, Golovinomyces orontii, Golovinomyces spp., Podosphaera xanthii, Podosphaera spp., Arthrocladiella mougeotii, Neoerysiphe galeopsidis, Phyllactinia kakicola, Phyllactinia spp., Cyphellophora laciniata, Sphaerographium tenuirostrum, Microsphaera trifolii, Sphaerotheca spiraeae, Sphaerotheca spp., Uncinuliella australiana, Absidia corymbifera, Absidia spp., Geotrichum spp., Nectria curta, Anamika lactaηolens, Hebeloma velutipes, Stropharia ambigua, Agrocybe praecox, Hydnum rufescens, Hydnum spp., Meliniomyces variabilis, Rhizoscyphus ericae, Cryptosporiopsis ericae, Hyalodendron spp., Leptographium lundbergii, Leptographium spp., Termitomyces spp., Coccidioides posadasii, Coccidioides immitis, Sclerotinia sclerotiorum, Phomopsis spp., Metarhizium anisopliae, Cordyceps spp., Tilletiopsis washingtonensis, Cerrena unicolor, Stachybotrys chartarum, Phaeococcomyces nigricans, Ganoderma philippii, Ganoderma spp., Gloeophyllum sepiarium, Cystotheca lanestris, Leveillula tauηca, Phyllactinia Varicosporium elodeae, Rhinocladiella basitonum, Melanchlenus oligospermus, Clavispora lusitaniae, Rhizopus spp., Phizomucor spp., Mucor spp., Conidiobolus coronatus, Conidobolus spp., Basidiobolus ranarum, basidiobolus spp., Ochronis spp., Histoplasma capsulatum, histoplasma spp., Wikoxina mikolae, Lasiodiplodia spp., Physcia caesia, Physcia spp., Brachyconidiellopsis spp., Conocybe lacteal, Gastrocybe lateritia, Gastrocybe spp., Agrocybe semiorbiculaηs, Taphrina pruni, Taphrina spp., Asterophora parasitica, Asterophora spp., Eremothecium ashbyi, Tricladium splendens, Ramaria flava, Ramaria spp., Laccaria fraternal, Scutellospora spp., Illosporium carneum, Hobsonia christiansenii, Marchandiomyces corallinus, Fusicoccum luteum, Botryosphaeria ribis, Pseudozyma aphidis, Pseudozyma spp., Peso turn erubescens, Battarrea stevenii, Battarrea spp., Harposporium janus, Harposporium spp., Hirsutella rhossiliensis, Arthroderma ciferrii, Arthroderma spp., Pucciniastrum goeppertianum, Cronartium occidentale, Cronartium arizonicum, Cronartium spp., Peridermium harknessii, Peridermium spp., Chrysomyxa arctostaphyli, Holleya sinecauda, Holleya spp., Zoophthora radicans, Smittium culisetae, Auxarthron zuffianum, Renispora flavissima, Ctenomyces serratus, and Sporothrix schenckii.

Standard methods in the art may be used to determine homology. For example the UWGCG Package provides the BESTFIT program which can be used to calculate homology, for example used on its default settings (Devereux et al, Nucleic Acids Research, 1984; 12: 387-395). The PILEUP and BLAST algorithms can be used to calculate homology or line up sequences (such as identifying equivalent residues or corresponding sequences (typically on their default settings)), for example as described in Altschul J Mol Evol, 1993; 36: 290-300; Altschul, et al (J Mol Biol, 1990; 215: 403-10). Software for performing BLAST analyses is publicly available through the National Center for Biotechnology Information (http://www.ncbi.nlm.nih.gov/).

In one embodiment, the universal region itself is detected. In another embodiment, RNA transcribed from the universal region is detected. The presence in the sample of RNA transcribed from a universal region is itself indicative of the presence of the universal region in the sample. The manner in which the universal region or any RNA transcribed therefrom is detected is discussed in more detail below.

The universal region or the RNA transcribed therefrom is typically extracted from fungal cells present in the sample before it is detected. The universal region can be extracted using routine methods known in the art. For instance, suitable methods for extracting fungal DNA are disclosed in Fredricks et al, J. Clin. Microbiol., 2005; 43(1): 5122-5128, US Patent Application No. 2002/0115077, and U.S. Pat. No. 6,605,439. Suitable methods of extracting fungal RNA are disclosed in the art, such as the lithium chloride purification method disclosed in Sambrook et al, 2001, Molecular Cloning: a laboratory manual, 3rd edition, Cold Spring Harbour Laboratory Press. Kits for the extraction of fungal RNA, such as the RNeasy mini kit (Qiagen), are also commercially available.

The universal region can be detected using any method known in the art. The universal region is preferably detected using a probe that specifically hybridizes to the universal region. Typically, the detecting comprises contacting the probe with the sample under conditions in which the probe specifically hybridizes to the region, if present, and determining the presence or absence of the hybridization product. The presence of the hybridization product indicates the presence of the universal region. Conversely, the absence of the hybridization product indicates the absence of the universal region.

The probe is typically a nucleic acid, such as DNA, RNA, PNA or a synthetic nucleic acid. A probe specifically hybridizes to the universal region if it preferentially or selectively hybridizes to the universal region but does not hybridize to any other DNA or RNA sequences.

The probe preferably specifically hybridizes to the universal region under stringent conditions. Conditions that permit the hybridization are well-known in the art (for example, Sambrook et al, 2001, Molecular Cloning: a laboratory manual, 3rd edition, Cold Spring Harbour Laboratory Press; and Current Protocols in Molecular Biology, Chapter 2, Ausubel et al, Eds., Greene Publishing and Wiley-Interscience, New York (1995)). Detection can be carried out under low stringency conditions, for example in the presence of a buffered solution of 30 to 35% formamide, 1 M NaCl and 1% SDS (sodium dodecyl sulfate) at 37° C. followed by a wash in from IX (0.1650 M Na+) to 2× (0.33 M Na+) SSC (standard sodium citrate) at 500 C. Detection can be carried out under moderate stringency conditions, for example in the presence of a buffer solution of 40 to 45% formamide, 1 M NaCl, and 1% SDS at 370 C, followed by a wash in from 0.5× (0.0825 M Na+) to IX (0.1650 M Na+) SSC at 550 C. Detection can be carried out under high stringency conditions, for example in the presence of a buffered solution of 50% formamide, 1 M NaCl, 1% SDS at 37° C., followed by a wash in 0.1× (0.0165 M Na+) SSC at 600 C.

The probe can be the same length as, shorter than or longer than the universal region. The probe is typically at least 5, at least 6, at least 7, at least 8, at least 9, at least 10, at least 15, at least 20, at least 25, at least 30, at least 35, at least 45, at least 50, at least 75 or at least 100 nucleotides in length. For example, the probe can be from 5 to 200, from 7 to 100, from 10 to 50 nucleotides in length. The probe is preferably 5, 10, 15, 20, 25, 30, 35 or 40 nucleotides in length. The probe preferably includes a sequence that shares at least 80%, at least 85%, at least 90%, at least 95%, at least 98%, at least 99% homology based on sequence identity with the universal region. Homology can be determined as discussed above.

The probe is detectably-labeled. The detectable label allows the presence or absence of the hybridization product formed by specific hybridization between the probe and the universal region (and thereby the presence or absence of the universal region) to be determined. Any label can be used. Suitable labels include, but are not limited to, fluorescent molecules, radioisotopes, e.g. 1251, 35S, enzymes, antibodies and linkers such as biotin.

The probe can be a scorpion probe, which is a probe linked to primer. The primer part of the probe can be designed to amplify the region of fungal DNA to be detected and the probe part can designed to detect the amplified region. Scorpion probes are well-known in the art. They are described in, for example, Whitcombe et al. (Nat. Biotechnol., 1994; 1 17: 804-807).

The probe can be a molecular beacon probe. Molecular beacon probes comprise a fluorescent label at one end and a quenching molecule at the other. In the absence of the region to be detected, the probe forms a hairpin loop and the quenching molecule is brought into close proximity with the fluorescent label so that no signal can be detected. Upon hybridization of the probe to the region to be detected, the loop unzips and the fluorescent molecule is separated from the quencher such that a signal can be detected. Suitable fluorescent molecule and quencher combinations for use in molecular beacons are known in the art. Such combinations include, but are not limited to, carboxyfluorsecein (FAM) and dabcyl. The probe is preferably the molecular beacon shown in SEQ ID NO: 4, SEQ ID NO: 44 or SEQ ID NO: 45.

The region of fungal DNA can be detected using TaqMan PCR. This technique is well-known in the art.

The probe may be immobilised on a support using any technology which is known in the art. Suitable solid supports are well-known in the art and include plates, such as multi well plates, filters, membranes, beads, chips, pins, dipsticks and porous carriers. The nanoparticles may be immobilised on a support using any technology which is known in the art.

The detecting of the universal region preferably comprises the step of amplifying the universal region or the RNA transcribed therefrom. In one embodiment, the region is amplified before its presence is determined. In another embodiment, the region is detected in real time as its presence is determined. Real-time methods are disclosed in the Examples and have been described in the art. Such methods are described in, for example, U.S. Pat. No. 5,487,972 and Afonia et al. (Biotechniques, 2002; 32: 946-9).

In one embodiment, only the region to be detected is amplified. In other embodiments, the region to be detected is amplified as part of a much larger length of fungal DNA or RNA. Sequences of DNA or RNA having at least 10, at least 20, at least 30, at least 40, at least 50, at least 60, at least 70, at least 80, at least 90, at least 100, at least 150, at least 200, at least 250, at least 300, at least 400 or at least 500 nucleotides and comprising the region to be detected can be amplified. For example, sequences having from 10 to 2000, from 20 to 1500, from 50 to 1000 or from 100 to 500 nucleotides can be amplified.

The DNA or RNA can be amplified using routine methods that are known in the art. The amplification of fungal DNA is preferably carried out using polymerase chain reaction (PCR) or nucleic acid sequence based analysis (NASBA). Suitable methods for PCR are disclosed in, for example, U.S. Pat. No. 6,605,439, EP-B-0979312 and Buchheidt et al. (British Journal of Haematology, 2002; 116: 8030811).

A suitable method for the amplification of fungal DNA by NASBA is described in Widjojoatmodjo et al, J. Microbiol. Methods, 1999; 38(1-2): 81-90.

Fungal RNA can be amplified using routine methods in the art, such as reverse transcription-PCR.

A person skilled in the art will be able to design specific primers to amplify the universal region. Primers are normally designed to be complementary to sequences at either end of the sequence to be amplified but not complementary to any other sequences. Primer design is discussed in, for example, Sambrook et al, 2001, supra.

Primers that amplify the 18S region are disclosed in, for example, Buchheidt et al. (British Journal of Haematology, 2002; 1 16: 803081 1) and Makimura et al. (Japan J. Med. Sci. Biol., 1994; 47: 144-156).

The universal region is preferably amplified using (a) the primers shown in SEQ ID NOs: 2 and 3; or (b) one of the sense primers shown in SEQ ID NOs: 48 and 50 and one of the antisense primers shown in SEQ ID NOs: 49 and 51.

The universal region or RNA transcribed therefrom is extracted from fungal cells and so may be contaminated with one or factors that interfere with the amplification and/or detection steps. For this reason, the universal region is typically detected in the presence of an internal PCR amplification control. This ensures that any DNA present in the sample is amplified correctly. The internal PCR amplification control preferably comprises a non-fungal sequence. The universal region is preferably detected in the presence of a cloned or synthesized tRNA-LEU intron region added to the amplification mixture in a predetermined amount to rule out the presence of inhibitors or other defective amplification steps. The tRNA-LEU intron region preferably comprises a portion of the Maize (*Zea mays*) tRNA-LEU intron region as shown in SEQ ID NO: 9. The sequence of the Maize (*Zea mays*) tRNA-LEU intron region lacks homology with any sequence present in humans or pathogenic fungal species. The internal PCR amplification control preferably involves detecting a specific portion of SEQ ID NO: 9 as shown in SEQ ID NO: 10. SEQ ID NO: 10 can be detected using a detectably-labeled probe that specifically hybridizes to SEQ ID NO: 10 as described above. The probe preferably includes a sequence that shares at least 80%, at least 85%, at least 90%, at least 95%, at least 98%, at least 99% homology based on sequence identity with SEQ ID NO: 10. The probe more preferably comprises a sequence that is identical to SEQ ID NO: 10. The detection of SEQ ID NO: 10 is most preferably carried out using the pair of oligonucleotides primers shown in SEQ ID NOs: 11 and 12 and the molecular beacon as shown in SEQ ID NO: 13. The primers are capable of amplifying a sequence within the Maize (*Zea mays*) tRNA-LEU intron region that contains SEQ ID NO: 10 as shown in Table 1 and the molecular beacon is capable of specifically detecting the presence of SEQ ID NO: 10.

Genera Detection Methods

The invention also provides methods for the rapid detection of the presence or absence in a sample of a fungus belonging to the genus *Candida*, *Aspergillus* or *Pneumocystis*. The methods give a rapid indication of whether or not a fungus belonging to the genus *Candida*, *Aspergillus* or *Pneumocystis* is contained within a sample. The methods involve detecting in the sample a region of fungal DNA that is specific for *Candida*, *Aspergillus* or *Pneumocystis*. The presence in a sample of a region of fungal DNA that is specific for a particular genus is indicative of the presence of a fungus belonging to that genus in the sample. The absence from the sample of a region of fungal DNA that is specific for a particular genus is indicative of the absence of a fungus belonging to that genus from the sample. A region of DNA that is specific for a genus is a region of DNA that is only present in that genus of fungi. Hence, a region of fungal DNA that is specific for a genus is present in the genomes of all the species of the genus but is not present in the genomes of species of other fungal genera. A region of fungal DNA that is specific for a genus is not present in the genome of any other organism, particularly microorganisms such as a bacteria or a virus.

The methods for detecting the presence or absence of a fungus belonging to the genera *Candida* and *Aspergillus* can be carried out on any sample. The method for detecting the presence or absence of a fungus belonging to the genus *Pneumocystis* is carried out on a sample obtained from a human. Specific types of sample are discussed in more detail below. In one embodiment, the methods are carried out on a sample that is known to contain a fungus. For instance, the methods can be carried out on a sample that has already undergone the panfungal detection method described above and a positive result was achieved. The methods can be carried out on a sample to confirm the identity of one or more fungi whose presence in the sample is known. In another embodiment, the methods are carried on a sample whose fungus-containing status is not known. The methods are typically carried out on a sample that is suspected of a fungus belonging to the genus *Candida*, *Aspergillus* or *Pneumocystis*.

SEQ ID NO: 5 shows a region of fungal DNA that is specific for *Candida*. The method for detecting the presence or absence of a fungus belonging to the genus *Candida* comprises detecting in the sample the presence or absence of a region of fungal DNA that shares at least 80% homology or sequence identity with SEQ ID NO: 5. The region preferably shares at least 85%, at least 90%, at least 95%, at least 98% or at least 99% homology or sequence identity with SEQ ID NO: 5. The sequence is more preferably identical to SEQ ID NO: 5. Homology can be determined as described above.

This method can be used to detect the presence or absence of any species of fungus belonging to the genus *Candida*. The fungus can be *Candida albicans, Candida dubliniensis, Candida famata, Candida glabrata, Candida guilliermondii, Candida haemulonii, Candida keyjyr, Candida krusei, Candida lusitaniae, Candida Hpolytica, Candida norvegensis, Candida parapsilosis, Candida tropicalis, Candida viswanathii, Candida inconspicua, Candida catenulata* (also known as *Candida brumptii* and *Candida ravautii*), *Candida pseudotropicalis, Candida parapsilosis, Candida metapsilosis, Candida orthopsilosis, Candida ciferrii, Candida famata, Candida lipolytica, Candida norvegensis, Candida rugosa, Candida viswanathii* or *Candida zeylanoides*.

SEQ ID NO: 14 shows a region of fungal DNA that is specific for *Aspergillus*. The method for detecting the presence or absence of a fungus belonging to the genus *Aspergillus* comprises detecting in the sample the presence or absence of a region of fungal DNA that shares at least 80% homology or sequence identity with SEQ ID NO: 14. The region preferably shares at least 85%, at least 90%, at least 95%, at least 98% or at least 99% homology or sequence identity with SEQ ID NO: 14. The sequence is more preferably identical to SEQ ID NO: 14. Homology can be determined as described above.

This method can be used to detect the presence or absence of any species of fungus belonging to the genus *Aspergillus*. The fungus can be *Aspergillus alliaceus, Aspergillus alutaceus, Aspergillus atroviolaceus, Aspergillus caesiellus, Aspergillus candidus, Aspergillus carneus, Aspergillus chevalieri, Aspergillus clavato-nanicus, Aspergillus clavatus, Aspergillus conicus, Aspergillus deflectus, Aspergillus fischerianus, Aspergillus flavipes, Aspergillus flavus, Aspergillus fumigatus, Aspergillus glaucus, Aspergillus hollandicus, Aspergillus janus, Aspergillus japonicus, Aspergillus nidulans, Aspergillus niger, Aspergillus niger* var. *awamorii, Aspergillus niveus, Aspergillus ochraceus, Aspergillus oryzae, Aspergillus penicilloides, Aspergillus reptans, Aspergillus restrictus, Aspergillus rubrobrunneus, Aspergillus spinosus, Aspergillus sydowii, Aspergillus tamarii, Aspergillus terreus, Aspergillus tetrazonus, Aspergillus unguis, Aspergillus ustus* or *Aspergillus versicolor*.

SEQ ID NO: 18 shows a region of fungal DNA that is specific for *Pneumocystis*. The method for detecting the presence or absence of a fungus belonging to the genus *Pneumocystis* comprises detecting in the sample the presence or absence of a region of fungal DNA that shares at least 80% homology with SEQ ID NO: 18. The region preferably shares at least 85%, at least 90%, at least 95%, at least 98% or at least 99% homology or sequence identity with SEQ ID NO: 18. The sequence is more preferably identical to SEQ ID NO: 18. Homology can be determined as described above.

This method can be used to detect the presence or absence of any species of fungus belonging to the genus *Pneumocystis*. The fungus can be *Pneumocystis carinii* or *Pneumocystis jirovecii*.

In one embodiment, the region of fungal DNA that is specific for *Candida*, *Aspergillus* or *Pneumocystis* (i.e. that is homologous to SEQ ID NO: 5, 14 and 18) is itself detected. In another embodiment, any RNA transcribed from the region is detected.

In one embodiment, only the region of fungal DNA is detected. In another embodiment, the region of fungal DNA is detected as part of larger sequence. For instance, the region can be detected as part of a sequence that has flanking sequences as described above with reference to the panfungal detection method.

The region of fungal DNA or any RNA transcribed therefrom can be extracted as described above with reference to the panfungal detection method.

The region of fungal DNA or any RNA transcribed therefrom can be detected using any method described above with reference to the panfungal method. The detecting of the region of fungal DNA preferably comprises the step of amplifying the fungal DNA or any RNA transcribed therefrom as described above with reference to the panfungal detection method.

The region of fungal DNA that is specific for *Candida* (i.e. the region that is homologous to SEQ ID NO: 5) is preferably detected using the molecular beacon probe shown in SEQ ID NO: 8. The region of fungal DNA that is specific for *Candida* is preferably amplified using the primers shown in SEQ ID NOs: 6 and 7.

The region of fungal DNA that is specific for *Aspergillus* (i.e. the region that is homologus to SEQ ID NO: 14) is preferably detected using the molecular beacon probe shown in SEQ ID NO: 17. The region of fungal DNA that is specific for *Aspergillus* is preferably amplified using (a) the primers shown in SEQ ID NOs: 15 and 16; or (b) the primers shown in SEQ ID NOs: 46 and 47.

The region of fungal DNA that is specific for *Pneumocystis* (i.e. the region that is homologus to SEQ ID NO: 18) is preferably detected using the molecular beacon probe shown in SEQ ID NO: 21. The region of fungal DNA that is specific for *Pneumocystis* is preferably amplified using the primers shown in SEQ ID NOs: 19 and 20.

The molecular beacon probes used in any of the above genus detection methods are detectably-labeled. The molecular beacon probes can be labeled in any manner described above with reference to the panfungal detection method.

The region of fungal DNA is typically detected in these methods in the presence of an internal PCR amplification control as described above with reference to the panfungal detection method.

Two or three of the above methods can be carried out simultaneously. Hence, the presence or absence of fungi belonging to (i) *Candida* and *Aspergillus*, (ii) *Candida* and *Pneumocystis* or (iii) *Aspergillus* and *Pneumocystis* can be simultaneously detected in a sample. Similarly, the presence or absence of fungi belonging to *Candida*, *Aspergillus* and *Pneumocystis* can be simultaneously detected in a sample. Simultaneous detection means that the fungi belonging to the two or more genera are detected at the same time. The two or more genera are typically detected in the same volume of sample. In other words, the two or more genera are not typically detected in different aliquots of the sample. One, two or three of the above methods for detecting the presence or absence of fungi belonging to *Candida*, *Aspergillus* and *Pneumocystis* can be carried out simultaneously in a multiplex reaction with one or more of the panfungal detection methods described above and/or with one or more of the species detection methods described below. For instance, the presence or absence of (i) any fungus (i.e. panfungal) and a fungus belonging to *Candida*, (ii) any fungus and a fungus belonging to *Aspergillus*, (iii) any fungus and a fungus belonging to *Pneumocystis*, (iv) any fungus, a fungus belonging to *Candida* and a fungus belonging to *Aspergillus*, (v) any fungus, a fungus belonging to *Candida* and a fungus belonging to *Pneumocystis*, or (vi) any fungus, a fungus belonging to *Aspergillus* and a fungus belonging to *Pneumocystis*, can be simultaneously detected in a sample. Any of embodiments (i) to (vi) can further involve the simultaneous detection of the presence or absence of one or more, such as 2, 3, 4 or 5, of *Candida tropicalis, Candida parapsilosis, Candida albicans, Candida glabrata* or *Candida krusei*. Alternatively, the presence or absence of a fungus belonging to one, two or three of *Candida, Aspergillus* and *Pneumocystis* and one or more, such as 2, 3, 4 or 5, of *Candida tropicalis, Candida parapsilosis, Candida albicans, Candida glabrata* and *Candida krusei* can be simultaneously detected in a sample. The methods are typically carried out simultaneously in the same volume of sample, i.e. they are not typically carried out in different aliquots of the sample.

If more than one of the methods are carried out simultaneously, the different probes used to detect the different regions of fungal DNA (which indicate the presence or absence of a fungus or the different genera or species) are typically labeled with different labels. Probes having different labels are preferable when the different regions of fungal DNA are being detected simultaneously in the same volume of sample. When the two or more fungi are being detected in the same volume of sample, it must be possible to distinguish between the different labels and hence detect the different regions of fungal DNA. For instance, fluorescent molecules that emit different wavelengths of light can be used. A suitable group of fluorescent labels, each of which can be simultaneously detected, is HEX hexachloro fluorescein phosphoramidite (HEX), carboxyfluorescein (FAM), Cy® 5 and Texas Red®. Other suitable groups of labels are known in the art.

Species Detection Methods

The invention also provides methods for the rapid detection of the presence or absence of in a sample of a fungus belonging to the species *Candida tropicalis, Candida parapsilosis, Candida albicans, Candida glabrata* or *Candida krusei*. The fungus belonging to the species *Candida parapsilosis* can belong to group I (also known as *Candida parapsilosis*), group II (also known as *Candida orthopsilosis*) or group III (also known as *Candida metapsilosis*). The methods give a rapid indication of whether or not a fungus belonging to the particular species are contained within a sample. The methods involve detecting in the sample a region of fungal DNA using specific molecular beacon probes. The specific molecular beacon probes detect regions of fungal DNA that are specific for each species. These regions are shown as shaded boxes that only span the sequence of one species in FIG. 5 (SEQ ID NOs: 30, 34, 36, 38 and 40). A region of DNA that is specific for a species is a region of DNA that is only present in that species of fungi. Hence, a region of fungal DNA that is specific for a species is not present in the genomes of other species, even those of the same genus. A region of fungal DNA that is specific for a genus is not present in the genome of any other organism, particularly micro-organisms such as a bacteria or a virus. The presence in the sample of the region of DNA that is specific for a particular species is indicative of the presence of a fungus belonging to that species in the sample. The absence from the sample of the region of DNA that is specific for a particular species is indicative of the absence of a fungus belonging to that species from the sample.

The methods can be carried out on any sample. Specific types of sample are discussed in more detail below. In one embodiment, the methods are carried out on a sample that is known to contain a fungus as described above with reference to the panfungal detection method. In another embodiment, the methods are carried on a sample whose fungus-containing status is not known. The methods are typically carried out on a sample that is suspected of a fungus belonging to the species *Candida tropicalis, Candida parapsilosis, Candida albicans, Candida glabrata* or *Candida krusei*.

In one embodiment, the region of fungal DNA is itself detected. In another embodiment, any RNA transcribed from the region is detected.

In one embodiment, only the region of fungal DNA is detected. In another embodiment, the region of fungal DNA is detected as part of larger sequence. For instance, the region can be detected as part of a sequence that has flanking sequences as discussed above with reference to the panfungal detection method.

The region of fungal DNA or any RNA transcribed therefrom can be extracted as described above with reference to the panfungal detection method.

The presence or absence of the region of fungal DNA that is specific for *Candida tropicalis* is detected using the molecular beacon probe shown in SEQ ID NO: 33. The presence or absence of the region of fungal DNA that is specific for *Candida parapsilosis* is detected using the molecular beacon probe shown in SEQ ID NO: 35. The presence or absence of the region of fungal DNA that is specific for *Candida albicans* is detected using the molecular beacon probe shown in SEQ ID NO: 37. The presence or absence of the region of fungal DNA that is specific for *Candida glabrata* is detected using the molecular beacon probe shown in SEQ ID NO: 39. The presence or absence of the region of fungal DNA that is specific for *Candida krusei* is detected using the molecular beacon probe shown in SEQ ID NO: 43. The molecular beacon probes are detectably-labeled. The molecular beacon probes can be labeled in any manner described above with reference to the panfungal detection method.

The detecting of the region of fungal DNA preferably comprises the step of amplifying the fungal DNA or any RNA transcribed therefrom as described above with reference to the panfungal detection method. The region of fungal DNA in any one of the five species is preferably amplified using the primers shown in SEQ ID NOs: 31 and 32. The region of fungal DNA in *Candida krusei* can be detected using the primers shown in SEQ ID NOs: 41 and 42.

The region of fungal DNA is typically detected in these methods in the presence of an internal PCR amplification control as described above with reference to the panfungal detection method.

More than one of the above species detection methods can be carried out simultaneously. In particular, 2, 3, 4 or 5 of the methods can be carried out simultaneously in any combination. Hence, the presence or absence of fungi belonging to 2, 3, 4 or 5 of the particular species can be simultaneously detecting in a sample. Simultaneous detection means that the fungi belonging to the two or more species are detected at the same time. The two or more species are typically detected in the same volume of sample. In other words, the two or more species are not typically detected in different aliquots of the sample. One or more, such 2, 3, 4 or 5, of the above methods for detecting the presence or absence of particular species of *Candida* can be carried out simultaneously with one or more of the panfungal detection methods described above and/or one or more, such as 2 or 3, of the genus detection methods described above. For instance, in addition to the combinations described above, the presence or absence of any fungus (i.e. panfungal) and one or more, such as 2, 3, 4 or 5, of *Candida tropicalis, Candida parapsilosis, Candida albicans, Candida glabrata* and *Candida krusei* can be simultaneously detected in a sample. The methods are typically carried out simultaneously in the same volume of sample, i.e. they are not typically carried out in different aliquots of the sample.

When more than one of the particular species is being detected simultaneously, the different regions of fungal DNA (which indicate the different species) are preferably amplified using the primers shown in SEQ ID NOs: 31 and 32. These primers will amplify the appropriate region in each of the five particular species of fungus.

If the two or three of the methods are carried out simultaneously, the different probes used to detect the different regions of fungal DNA (which indicate the presence or absence of a fungus or the different genera or species) are typically labeled with different labels as discussed above with reference to the genus detection methods.

Sample

The sample used in the invention may be any suitable sample. The invention is typically carried out on a biological sample. The invention is preferably carried out in vitro on a biological sample. The biological sample can be obtained from or extracted from any organism. The organism is typically eukaryotic and can belong the plantae kingdom or the animalia kingdom. The sample can be a colony of fungus.

The sample is preferably a fluid sample. The sample typically comprises a body fluid. The sample may be urine, lymph, saliva, cerebrospinal fluid, peritoneal fluid, pericardial fluid, vitreous or other ocular sample, plural fluid, vaginal fluid, mucus, pus or amniotic fluid but is preferably blood, plasma or serum. The sample can be a cell or tissue sample, such as lung, brain, liver, skin or nails.

Typically, the sample is human in origin, but alternatively it may be non-human. For instance, the sample can be from animals such as from commercially farmed animals such as horses, cattle, sheep or pigs or may alternatively be pets such as cats or dogs. The sample can also be from other organisms, such as insects. The sample can be from a human or non-human animal undergoing treatment with an anti-fungal agent.

The invention can also be carried out on a non-biological sample. The non-biological sample can be a fluid or a solid. Examples of a non-biological sample include surgical fluids, air, water such as drinking water, reagents for laboratory tests and household containers. The sample may also be a particle collection device containing air, water, another liquid or a material.

The sample is typically processed prior to being used in the invention, for example by centrifugation or by passage through a membrane that filters out unwanted molecules or cells, such as red blood cells. The sample may have undergone polymerase chain reaction before being used in the invention. The sample may be measured immediately upon being taken. The sample may also be stored prior to assay, preferably below −70° C.

Kits

The invention also provides various kits for carrying out the methods of the invention. In particular, the invention provides a kit:

for the rapid detection of the presence or absence of any fungus in a sample, comprising (a) the molecular beacon probe shown in SEQ ID NO: 4 and the primers shown in SEQ ID NOs: 2 and 3; (b) the molecular beacon probe shown in SEQ ID NO: 44, one or both of the sense primers shown in SEQ ID NOs: 48 and 50 and one or both of the antisense primers shown in SEQ ID NOs: 49 and 51; or (c) the molecular beacon probe shown in SEQ ID NO: 45, one or both of the sense primers shown in SEQ ID NOs: 48 and 50 and one or both of the antisense primers shown in SEQ ID NOs: 49 and 51;

for the rapid detection of the presence or absence a fungus belonging to the genus *Candida* in a sample, comprising the molecular beacon probe shown in SEQ ID NO: 8 and the primers shown in SEQ ID NOs: 6 and 7;

for the rapid detection of the presence or absence of a fungus belonging to the genus *Aspergillus* in a sample, comprising the molecular beacon probe shown in SEQ ID NO: 17 and (a) the primers shown in SEQ ID NOs: 15 and 16 or (b) primers shown in SEQ ID NOs: 46 and 47; and for the rapid detection of the presence or absence of a fungus belonging to the genus *Pneumocystis* in a sample, comprising the molecular beacon probe shown in SEQ ID NO: 21 and the primers shown in SEQ ID NOs: 19 and 20; and for the rapid detection of the presence or absence of a fungus belonging to a particular species of *Candida* in a sample, comprising the primers shown in SEQ ID NOs: 31 and 32 or 41 and 42 and one or more of the molecular beacon probes shown in SEQ ID NOs 33, 35, 37, 39 and 43.

The kit for the rapid detection of the presence or absence of a fungus belonging to a particular species of *Candida* in a sample can comprise 1, 2, 3, 4 or all 5 of the molecular beacon probes shown in SEQ ID NOs 33, 35, 37, 39 and 43 in any combination.

The kits preferably further comprise reagents for extracting fungal DNA or RNA from a sample and/or primers that can be used to amplify the region of fungal DNA and/or an internal control for the amplification and detection stages. The internal control preferably comprises the portion of the Maize (*Zea mays*) tRNA-LEU intron region shown in SEQ ID NO: 9, the pair of oligonucleotides primers shown in SEQ ID NOs: 11 and 12 and the molecular beacon probe shown in SEQ ID NO: 13. The kit may additionally comprise one or more other reagents or instruments which enable the method of the invention as described above to be carried out. Such reagents or instruments include one or more of the following: suitable buffer(s) (aqueous solutions), means to obtain a sample from the subject (such as a vessel or an instrument comprising a needle) or a support comprising wells on which reactions can be done. Reagants may be present in the kit in a dry state such that a fluid sample resuspends the reagents. The kit may, optionally, comprise instructions to enable the kit to be used in a method of the invention.

Uses of the Invention

The invention concerns the detection and identification of a fungus in a sample. The invention can therefore be used for the diagnosis of a fungal infection in a patient. The invention can also be used to determine the presence of a fungus in or on any non-biological product and hence the likelihood that the product will cause a fungal infection. There are many situations in which it is important to ensure that a non-biological sample is fungus free. Examples include drinking water and liquids used in laboratories. In particular, the invention may be used to pretest the components in a fungal diagnostic kit to ensure the components are free from fungal nucleic acid (i.e. a quality control step). Other uses of the invention are clear to a person skilled in the art.

EXAMPLES

TABLE 1 the sequences of the primers and probes used in the Examples.

```
I-Panfungal
Sequence detected: TCGATTCCGGAGAGGGAGC (SEQ ID NO: 1)
Sequence detected: CTGCGGCTTAATTTGACTCA (SEQ ID NO: 52)
Sequence detected: ACATCCAAGGAAGGCAGCAG (SEQ ID NO: 53)

Ia-Panfungal Oligonucleotide Primers
5'-GCCCTATCAACTTTCGATGG-3' (SEQ ID NO: 2)
5'-GCCTTCCTTGGATGTGGTAG-3' (SEQ ID NO: 3)

Ib Panfungal Molecular Beacon Probe
5'-CGCGATTCGATTCCGGAGAGGGAGCATCGCG-3' (SEQ ID NO: 4)
(Hairpin structure nucleotides italicized)

II-Candida
Sequence detected: GATGATTCATAATAACTTTTCG (SEQ ID NO: 5)

IIa-Candida Oligonucleotide Primers
5'-TAGATAAAAAATCAATGCCTTCGG-3' (SEQ ID NO: 6)
5'-CATGGTAGGCCACTATCCTAC-3' (SEQ ID NO: 7)

IIb-Candida Molecular Beacon Probe
5'-CGCGATGATGATTCATAATAACTTTTCGATCGCG-3' (SEQ ID NO: 8)
(Hairpin structure nucleotides italicized)

III-Internal Control
Portion of the Maize (Zea mayis) tRNA-LEU intron region (SEQ ID NO: 9)
  1 TAATGAATTCAATGATTCAAAAAAAACTAAGAGATGGATTAAATTATACAAGGAATCCTG
 61 GTTTCAAAGAAAAGTAAAATGGGGATATGGCGAAATCGGTAGACGCTACGGACTTGATTG
121 TATTGAGCCTTGGTATGGAAACCTGCTAAGTGGTAACTTCCAAATTCAGAGAAACCCTGG
181 AATGAAAAATGGGCAATCCTGAGCCAAATCCCTTTTTTGAAAAACAAGTGGTTCTCAAAC
241 TAGAACCCAAAGGAAAAGGATAGGTGCAGAGACTCAATGGAAGCTGTTCTAACGAATCGA
301 AGTAATAACGATTAATCACAGAACCCATATTATAATATAGGTTCTTTATTTTATTTTTAG
361 AATGAAATTAGGAATGATTATGAAATAGAAAATTCATAATTTTTTTTTAGAATTATTGTG
421 AATCTATTCCAATCAAATATTGAGTAATCAAATCCTTCAATTCATTGTTTTCGAGATCTT
481 TTAATTTTAAAAAGTGGATTAATCGGACGAGGATAAAGAGAGAGTCCCATTCTACATGTC
541 AATACTGACAACAATGAAATTTCTAGTAAAAGGAAAATCCGTCGACTTTATAAGTCGTGA
601 GGGTTCAAGTCCCTCTATCCCCAAACCCTCTTTTATTCCC
```

The sequence highlighted in bold (SEQ ID NO: 10) was detected using the molecular beacon probe shown below (SEQ ID NO: 13). The sequences underlined show the sequences to which the primers shown below (SEQ ID NOs: 11 and 12) bind.

```
IIIa-Internal Control Oligonucleotide Primers
                                       (SEQ ID NO: 11)
5'-CCTGCTAAGTGGTAACTTCC-3'

(SEQ ID NO: 12)
5'-TGAGTCTCTGCACCTATCCT-3'

IIIb-Internal Control Molecular Beacon Probe
                                       (SEQ ID NO: 13)
5'-CGCACGCAATCCTGAGCCAAATCCCTCGTGCG-3'

(Hairpin structure nucleotides italicized)

IV-Aspergillus
Sequence detected:
                                       (SEQ ID NO: 14)
AGTTGAACCTTGGGTCTGGC IVa-Aspergillus Oligonucleotide Primers
                                       (SEQ ID NO: 15)
5'-GGTAATTCCAGCTCCAATAGC-3'

(SEQ ID NO: 16)
5'-GGCCTGCTTTGAACACTCTAA-3'

IVb-Aspergillus Molecular Beacon Probe
                                       (SEQ ID NO: 17)
5'-CGCGATAGTTGAACCTTGGGTCTGGCATCGCG-3'

(Hairpin structure nucleotides italicized)

V-Pneumocystis
Sequence detected:
                                       (SEQ ID NO: 18)
CTAGGATATAGCTGGTTTTCTGC Va-Pneumocystis Oligonucleotide Primers
                                       (SEQ ID NO: 19)
5'-GCAAAGTACTCAGAAGAATTGTGG-3'

(SEQ ID NO: 20)
5'-TCCCTCGAGATATTCAGTGC-3'

Vb-Pneumocystis Molecular Beacon Probe
                                       (SEQ ID NO: 21)
5'-CGCAGCCT AGG AT AGCTGGTTTTCTGCGCTGCG-3'

(Hairpin structure nucleotides italicized)

VI-Candida tropicalis
Sequence detected:
                                       (SEQ ID NO: 30)
CCTTTTGGCGAACCCAGGAC VIa-Oligonucleotide Primers
                                       (SEQ ID NO: 31)
5'-ATTGGAGGGCAAGTCTGGTG-3'

(SEQ ID NO: 32)
5'-CCGATCCCTAGTCGGCATAG-3'

VIb-Candida tropicalis Molecular Beacon Probe
                                       (SEQ ID NO: 33)
5'-CGCAGCCCTTTTGGCGAACCCAGGACGCTGCG-3'

(Hairpin structure nucleotides italicized)

VII-Candida parapsilosis
Sequence detected:
                                       (SEQ ID NO: 34)
TCTGGCTAGCCTTTTTGGCG VIIa-Oligonucleotide Primers-
SEQ ID NOs: 31 and 32 above VIIb-Candida parapsilosis Molecular Beacon Probe
                                       (SEQ ID NO: 35)
5'-CGGACGTCTGGCT AGCCTTTTTGGCGCGTCCG-3'

(Hairpin structure nucleotides italicized)

VIII-Candida albicans
Sequence detected:
                                       (SEQ ID NO: 36)
TTCTGGGTAGCCATTTATGG VIIIa-Oligonucleotide Primers-
SEQ ID NOs: 31 and 32 above VIIIb-Candida albi cans Molecular Beacon Probe
                                       (SEQ ID NO: 37)
5'-CGGACGTTCTGGGT AGCCATTT ATGGCGTCCG-3'

(Hairpin structure nucleotides italicized)

IX-Candida glabrata
Sequence detected:
                                       (SEQ ID NO: 38)
GCTAACCCCAAGTCCTTGTG IXa-Oligonucleotide Primers-
SEQ ID NOs: 31 and 32 above IXb-Candida glabrata Molecular Beacon Probe
                                       (SEQ ID NO: 39)
5'-CGGACGGCTAACCCCAAGTCCTTGTGCGTCCG-3'

(Hairpin structure nucleotides italicized)

X-Candida krusei
Sequence detected:
                                       (SEQ ID NO: 40)
TCGGGCGAACCAGGACGATT Xa-Oligonucleotide Primers
SEQ ID NOs: 31 and 32 above OR (SEQ ID NO: 41)
5'-GCAGTTAAAAAGCTCGTAGTTGAAC-3'

(SEQ ID NO: 42)
5'-AAAGGCCTGCTTTGAACACTCT-3'

Xb-Candida krusei Molecular Beacon Probe
                                       (SEQ ID NO: 43)
5'-CGCAGCTCGGGCGAACCAGGACGATTGCTGCG-3'

(Hairpin structure nucleotides italicized)
```

Example 1

Melting Curve for Panfungal Molecular Beacon Probes

Reported sequences for the design of primers and molecular beacon probes were used. Molecular beacon probes and DNA primers (Table 1, I) were designed using Beacon Designer 3.0 software (PREMIER Biosoft, Palo Alto, CA.). The default software parameters were applied for all molecular beacon probe and primer construction. Molecular beacon probes were labeled with fluorophores 5-carboxyfluorescein (FAM) at the 5' end and with dabcyl at the 3' end. The molecular beacon probes and primers were purchased from Biosearch Technologies (Biosearch Technologies, Novato, CA.). The hybridization properties of the molecular beacon probes were tested for the full temperature range, 25° C.-95° C., with single-stranded target oligonucleotides. Molecular beacon probe-target hybridization was performed with the Stratagene MX4000 Multiplex Quantitative PCR system (Stratagene, La Jolla, CA.). The "Molecular Beacon Melting Curve" experiment type was chosen in the MX4000 software for data monitoring and analysis.

Each 50 µl hybridization reaction mixture contained 1× Stratagene Core PCR buffer, 4 mM MgCl$_2$, 100 pmol of individual target oligonucleotide and 5 pmol of molecular beacon probe. The thermal conditions of experiment comprised heating at 95° C. for 3 minutes and cooling to 80° C. with subsequent cooling down to 25° C. using 112, 30-seconds steps with a temperature gradient −0.5° C. Fluorescence output for each individual reaction was measured at the end of the cooling step. Melting temperature ($T_m$) for each molecular beacon-target pair was determined by MX4000 software as a temperature point corresponding to maximal value of the first derivative of the fluorescence output −R'(T).

Example 2

Detection of Any Fungus (Panfungal Detection)

A real-time amplification assay was carried out using the primers and probes described in Table I (SEQ ID NOs: 2 to 4). The assay included DNA amplification by the polymerase chain reaction (PCR) with real-time detection utilizing molecular beacon probes. DNA from multiple fungal species were tested, together with negative controls consisting of DNA extracted from a Gram positive and Gram negative bacteria. Species tested were *Aspergillus flavus, Aspergillus fumigatus, Aspergillus japonicus, Aspergillus nidulans, Aspergillus niger, Aspergillus terreus, Candida albicans, Candida dubliniensis, Candida glabrata, Candida keyfr, Candida krusei, Candida lusitaniae, Candida lipolytica, Candida parapsilosis, Candida rugosa, Candida tropicalis, Cryptococcus neoformans, Saccharomyces cerevisiae, Pneumocystis carinii, Pneumocystis jirovecii, Escherichia coli* and *Staphylococcus aureus*. With the exception of the Pneumocystis samples, which were obtained from clinical samples, the DNA used was derived from strains obtained from ATCC (ATCC, Manassas, VA, USA)

The procedure was as follows. Real-time PCR experiments were performed on a Stratagene Mx4000 Multiplex Quantitative PCR System using the "Quantitative PCR (Multiple Standards)" setting. Reagents from Eurogentec (Liege, Belgium) were used for all reactions. Each 50-µl PCR reaction contained 1× Eurogentec reaction buffer, 0.2 µM of molecular beacon probe (1b, SEQ ID NO: 3), 0.25 µM of each of the primers of Ia shown in Table 1 (SEQ ID NOs: 1 and 2), 1.25 U of HotGoldStart Taq DNA polymerase (Eurogentec, Liege, Belgium), 0.4 mM dNTPs, 5 mM MgCl$_2$ between 10 pg and 100 ng of fungal chromosomal DNA. Real-time PCR thermal cycler parameters were: 1 cycle of 10 min at 95° C., 45 cycles of 30 s at 95° C., 30 s at 50° C. and 30 s at 72° C. The filter gain set of the Mx4000 System was changed to FAM-960. The fluorescence was measured 3 times during the annealing step.

Fluorescence signals coming from Stratagene Mx4000 System during PCR amplification were monitored using Mx4000 software in real time. At the end of each run, the amplification plots data were converted to graphic format and stored as image files or exported into Microsoft Office Excel and stored as spreadsheet files. Total changes in fluorescence for individual fluorophores (Rpost−Rpre) were taken as values for analysis. Results were converted to graphic or numerical format and stored as image or spreadsheet files. A summary of the results is shown in Table 2.

TABLE 2

A summary of the results of a real time PCR experiment using panfungal primers and molecular beacon probes (Ia and 1b (SEQ ID NOs: 2 to 4) in Table 1) to detect DNA from a variety of fungal and bacterial organisms.

| Sample | Organism | Realtime PCR Result |
|---|---|---|
| 1 | A. flavus | + |
| 2 | A. fumigatus | + |
| 3 | A. japonicus | + |
| 4 | A. nidulans | + |
| 5 | A. niger | + |
| 6 | A. terreus | + |
| 7 | C. albicans | + |
| 8 | C. dubliniensis | + |
| 9 | C. glabrata | + |
| 10 | C. guillermondii | + |
| 11 | C. keyfr | + |
| 12 | C. krusei | + |
| 13 | C. lusitaniae | + |
| 14 | C. lipolytica | + |
| 15 | C. parapsilosis | + |
| 16 | C. rugosa | + |
| 17 | C. tropicalis | + |
| 18 | C. neoformans | + |
| 19 | S. cerevisiae | + |
| 20 | P. carinii | + |
| 21 | P. jirovecii | + |
| 22 | E. coil | − |
| 23 | S. aureus | − |
| 24 | Water | − |

Example 3

Multiplex Detection of *Aspergillus* and *Candida* DNA

A real-time amplification assay was carried out for the detection of *Aspergillus, Candida* and panfungal (presence of any fungal) DNA using the primers and probes described in Table 1, I (SEQ ID NOs: 2 to 4), II (SEQ ID NOs: 6 to 7) and IV (SEQ ID NOs: 15 to 17), together with an assay for the presence of the Internal Control DNA using the primers and probes described in Table 1, III (SEQ ID NOs: 11 to 13). Fluorophores were conjugated to the beacon probes to allow detection. The fluorophores used are shown in Table 3.

TABLE 3

The fluorophores used to label each molecular beacon probe

Figure 11:
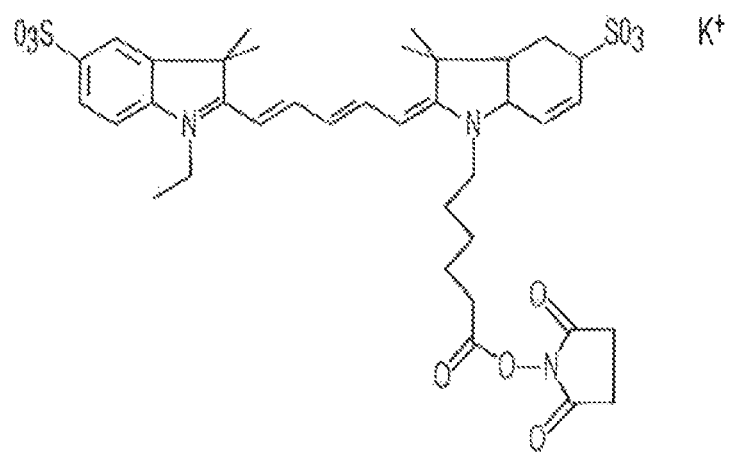
FIG. 11 shows the structure of Cy® 5 mono NHS ester.
Figure 12:
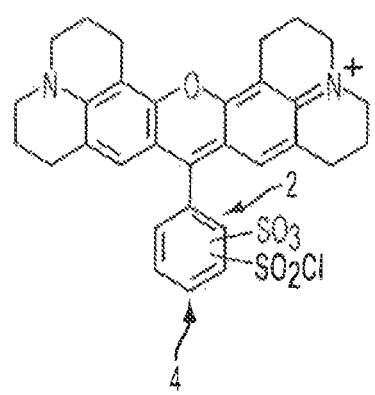
FIG. 12 shows the structure of Texas Red®.
Figure 13A:
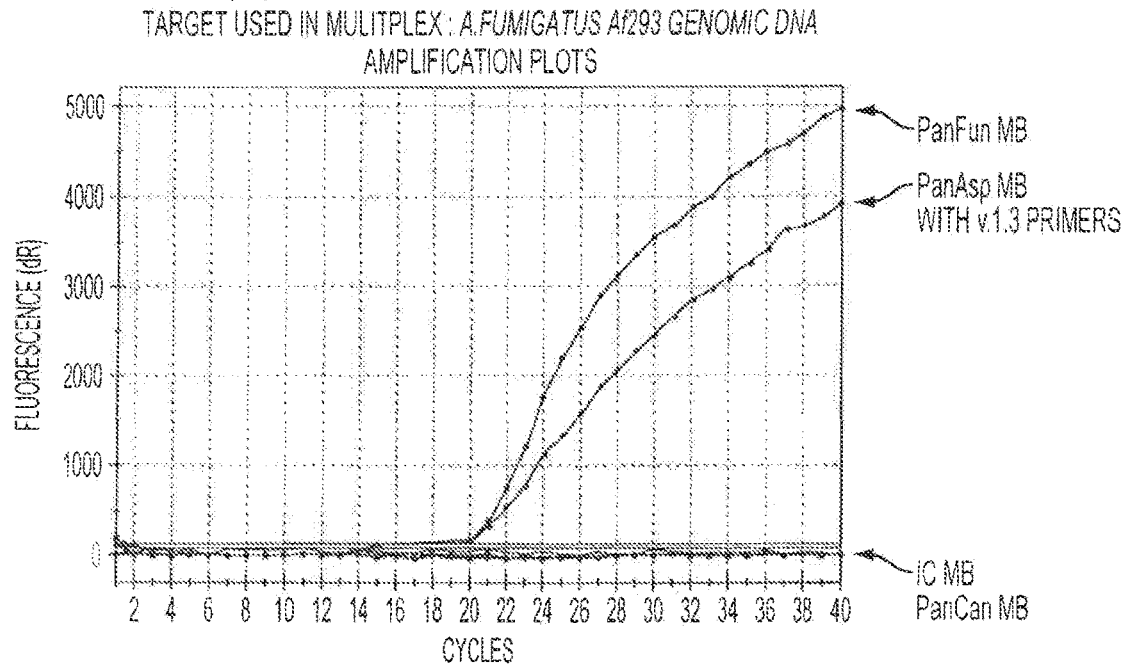
FIGS. 13A, 13B, 13C, 13D, 13E, 13F, 13G, 13H, 13I, 13J, 13K, 13L, 13M and 13N depict graphical displays of real-time PCR results from multiplex panel experiments (see Example 7).
Figure 13B:
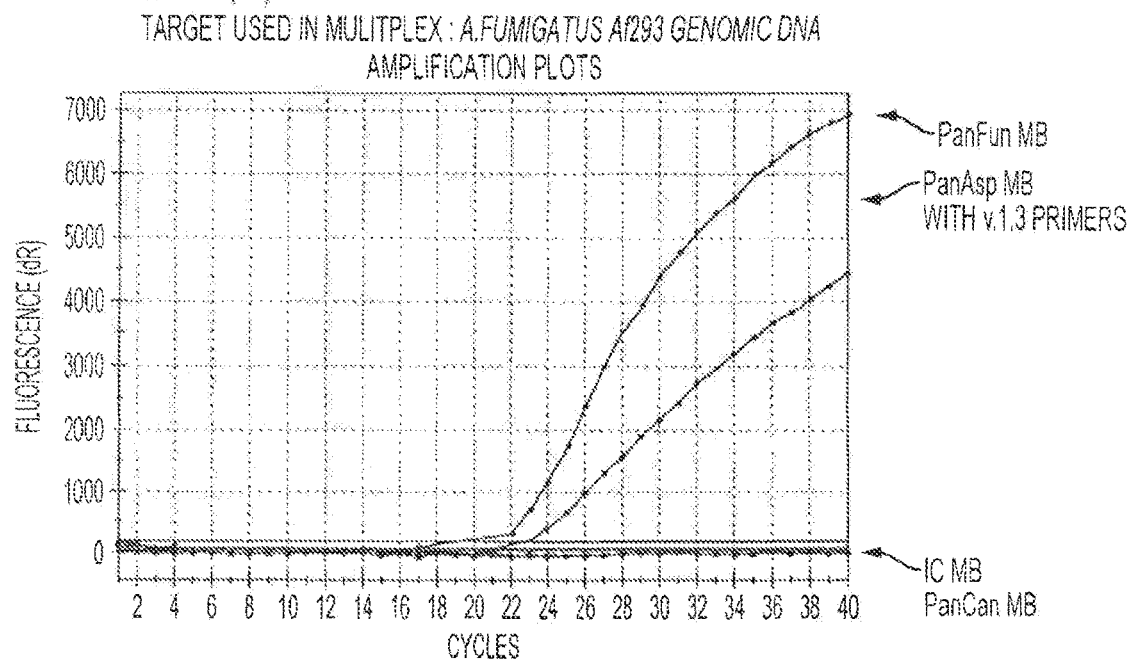
Figure 13C:
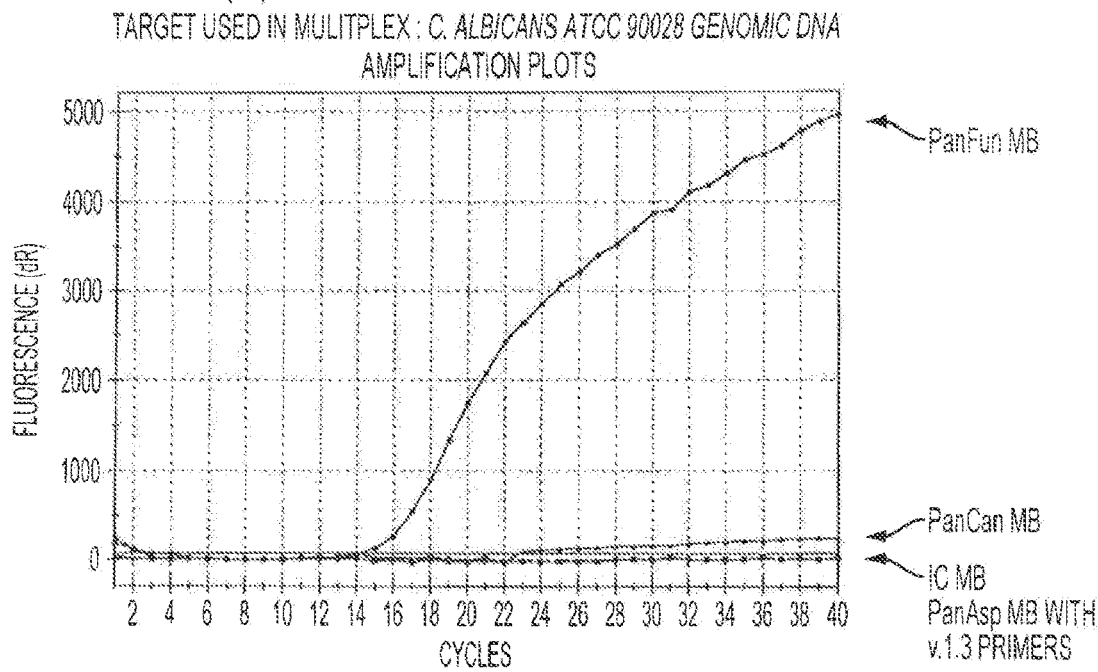
Figure 13D:
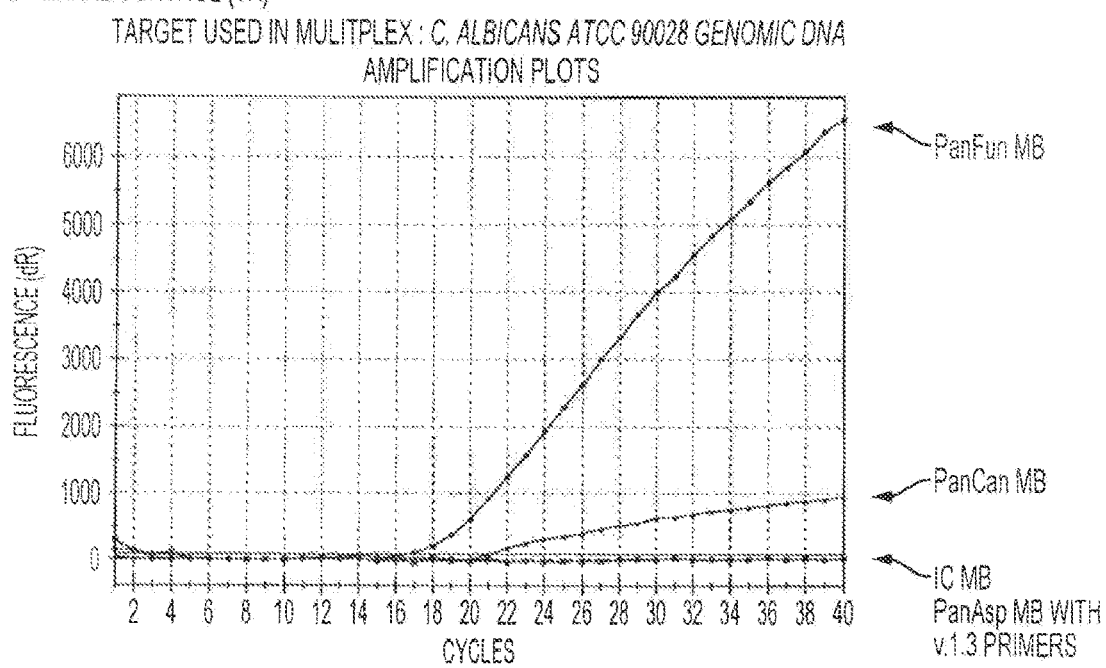
Figure 13E:
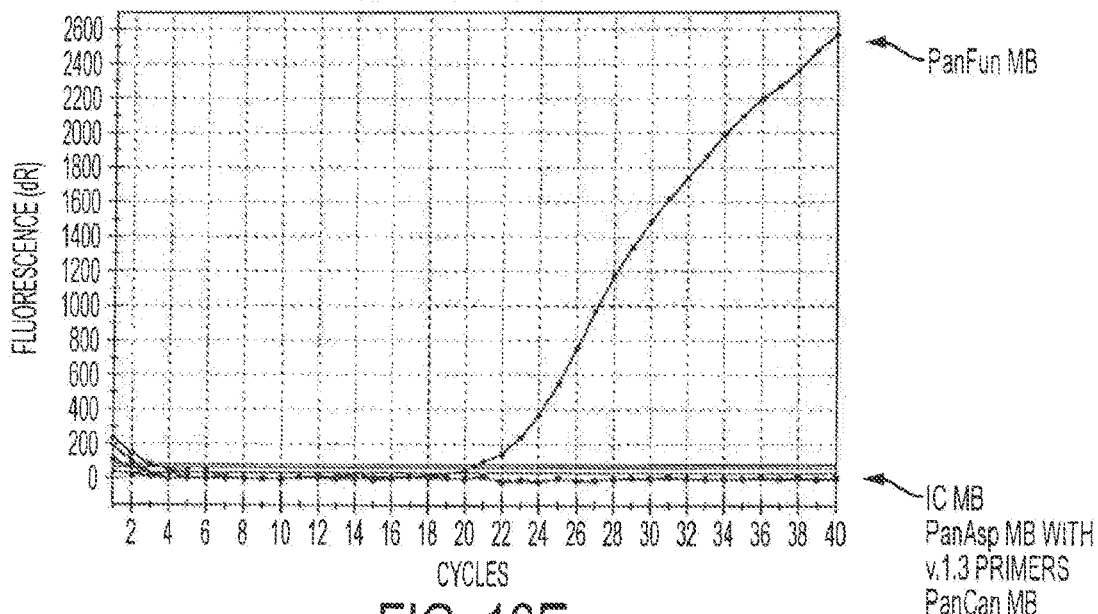
Figure 13F:
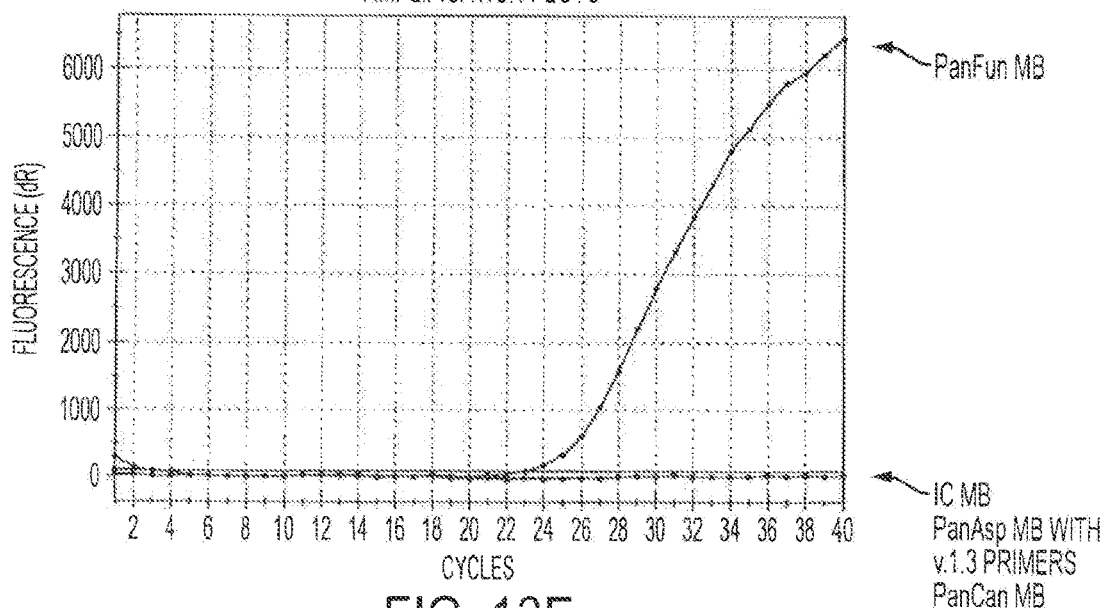
Figure 13G:
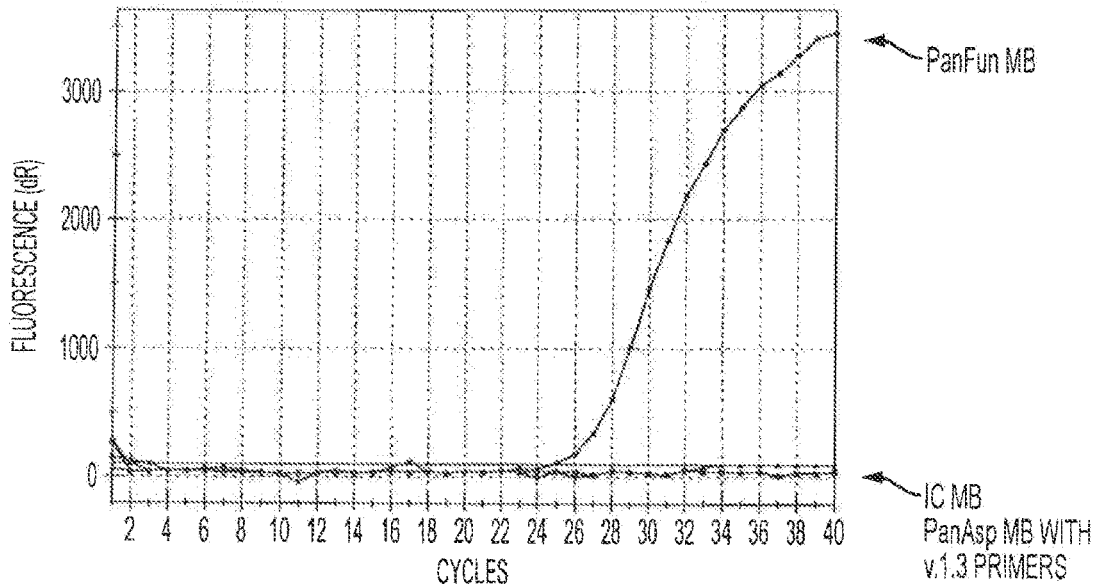
Figure 13H:
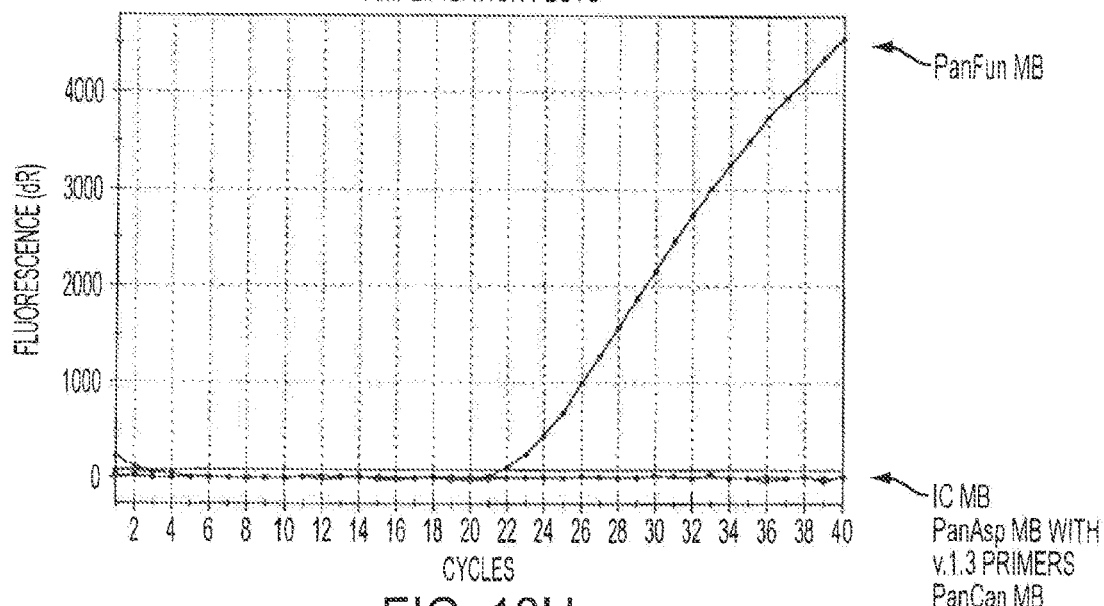
Figure 13I:
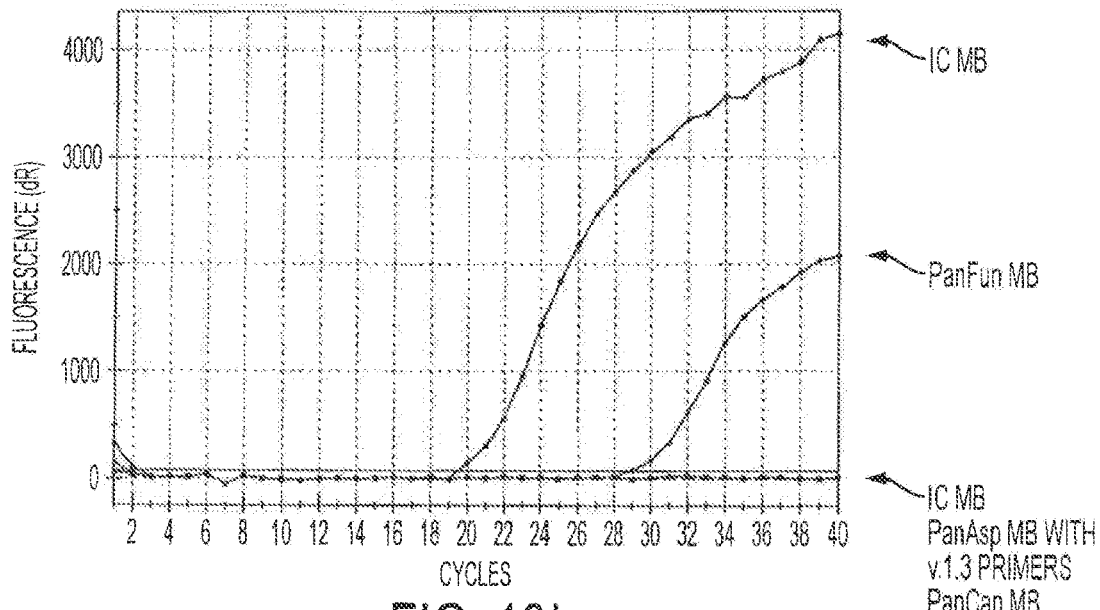
Figure 13J:
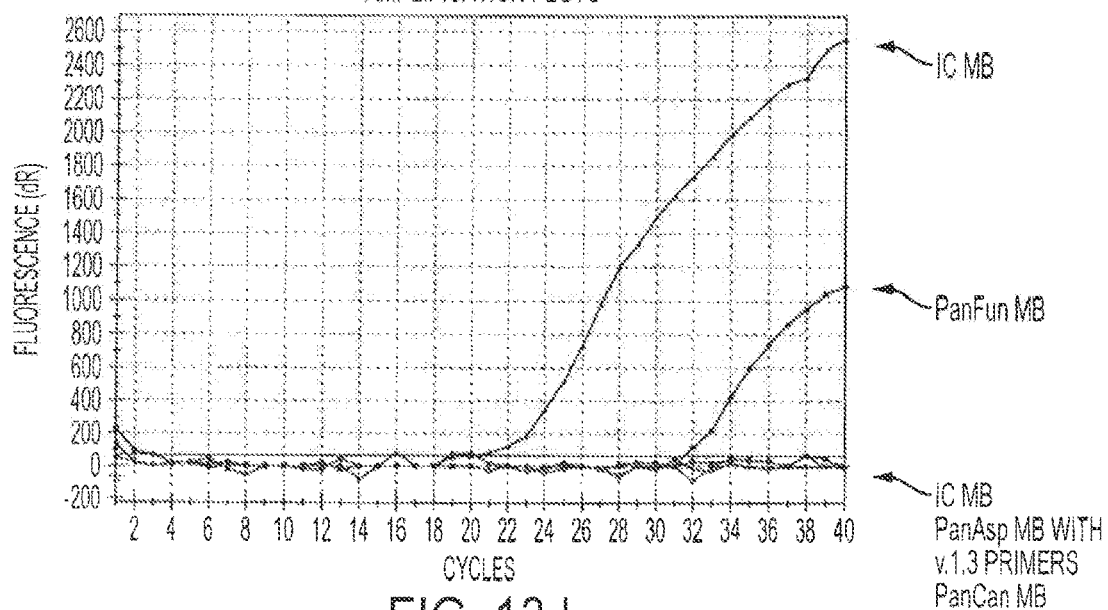
Figure 13K:
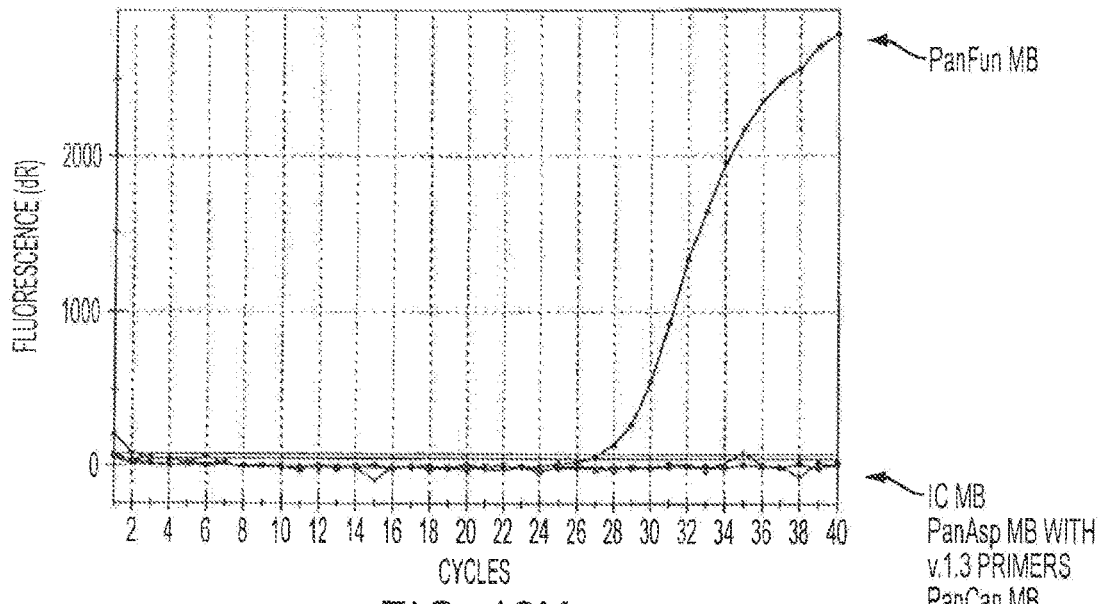
Figure 13L:
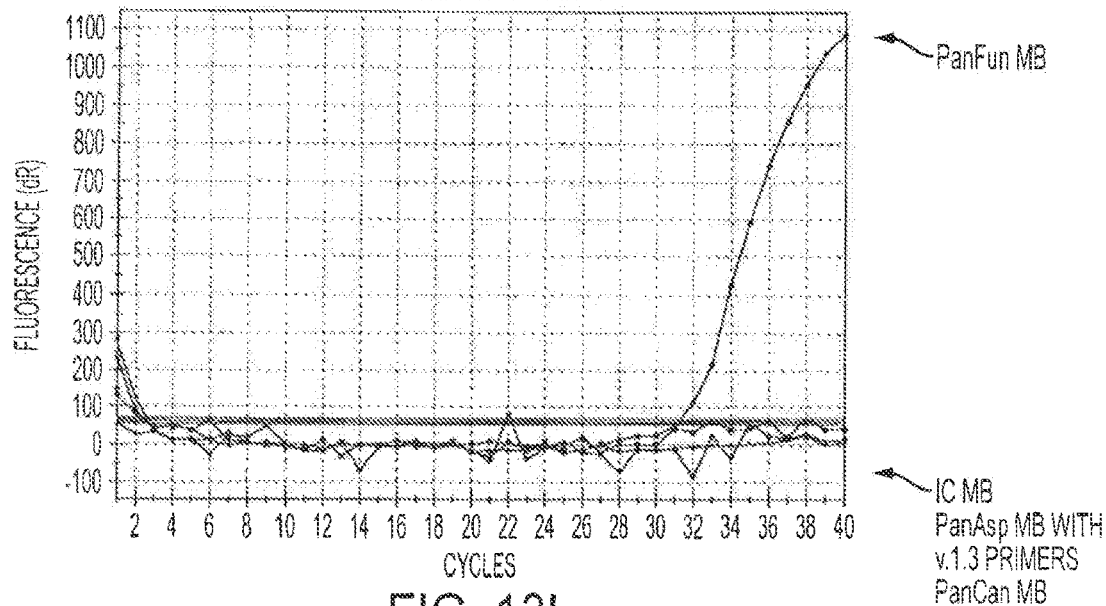
Figure 13M:
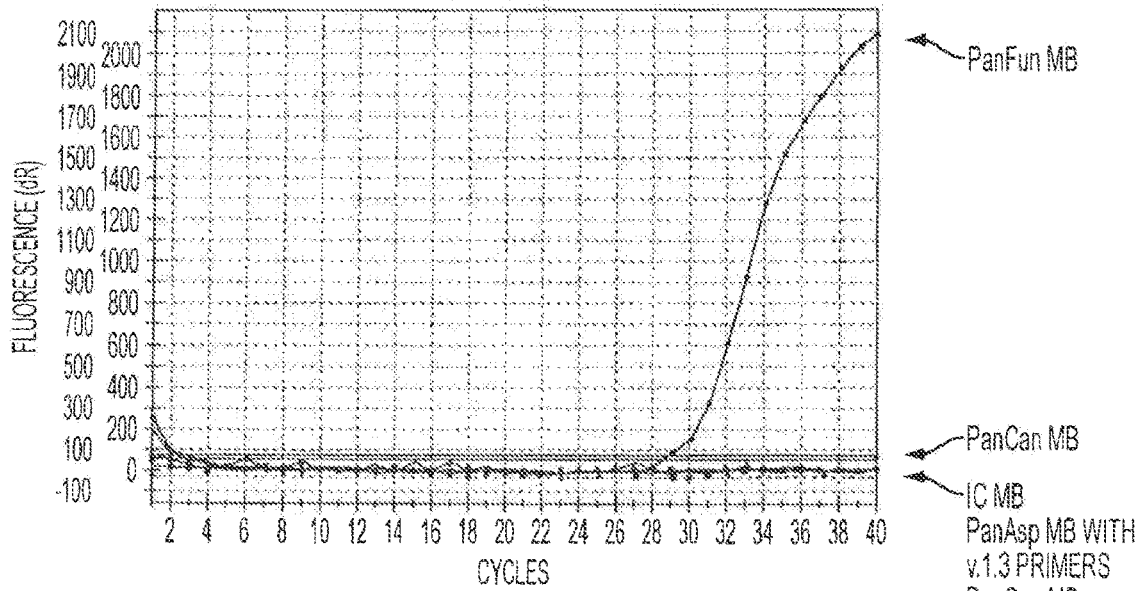
Figure 13N:
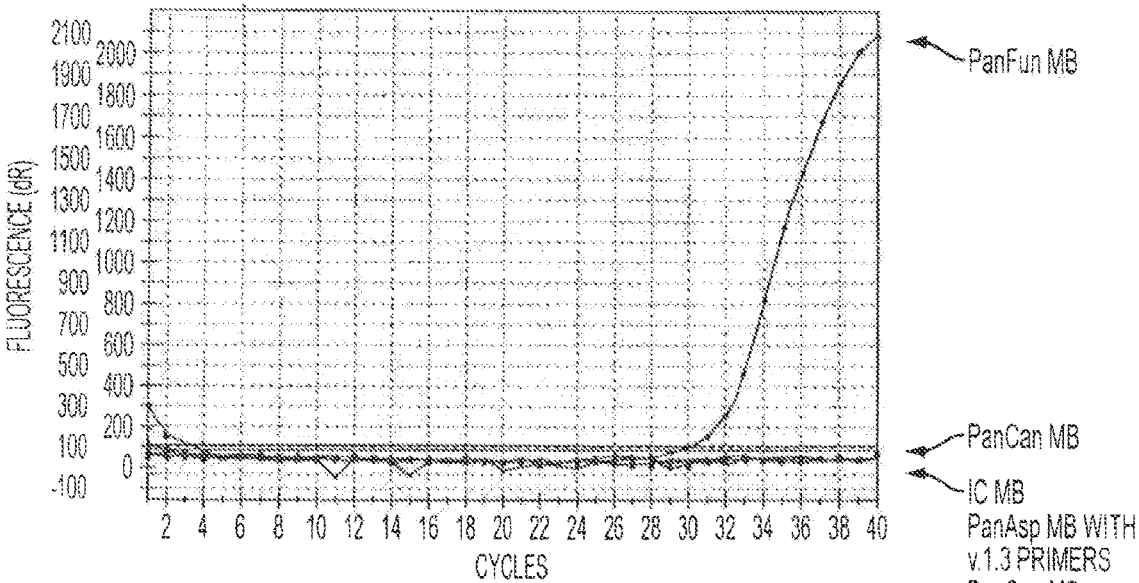

| Molecular Beacon Probe | Fluorophore |
|---|---|
| Aspergillus | HEX (hexachlorofluorescein phosphoramidite) |
| Candida | FAM (carboxyfluorescein) |
| Panfungal | Cy ®5 (a registered trade mark of GE Lifesciences. FIG. 11 shows the structure of Cy5 mono NHS ester) |
| Internal Control | Texas Red ® (registered trade mark of Molecular Probes, Inc. FIG. 12 shows the structure of Texas Red sulphonyl chloride). |

The assay included DNA amplification by the polymerase chain reaction (PCR) with real-time detection utilizing molecular beacon probes. DNA from multiple fungal species was tested, together with a DNA-template free negative control.

Real-time PCR experiments were performed on Stratagene Mx4000 Multiplex Quantitative PCR System using the "Quantitative PCR (Multiple Standards)" setting. Eurogentec qPCR MasterMix No ROX Kit was used for all reactions. Each 50-µl PCR reaction contained, 1× pPCR MasterMix with 4 mM $MgCl_2$, 20 pmol of each molecular beacon, 10-20 pmol of each primer and up to 100 ng of each DNA or water for the no template control. PCR reactions were performed using the parameters, as follows: 1 cycle of 10 min at 95° C., 45 cycles of 30 sat 95° C., 30 s at 50° C. and 30 s at 72° C. The fluorescence was measured 30 times during the annealing step.

Figure 2:
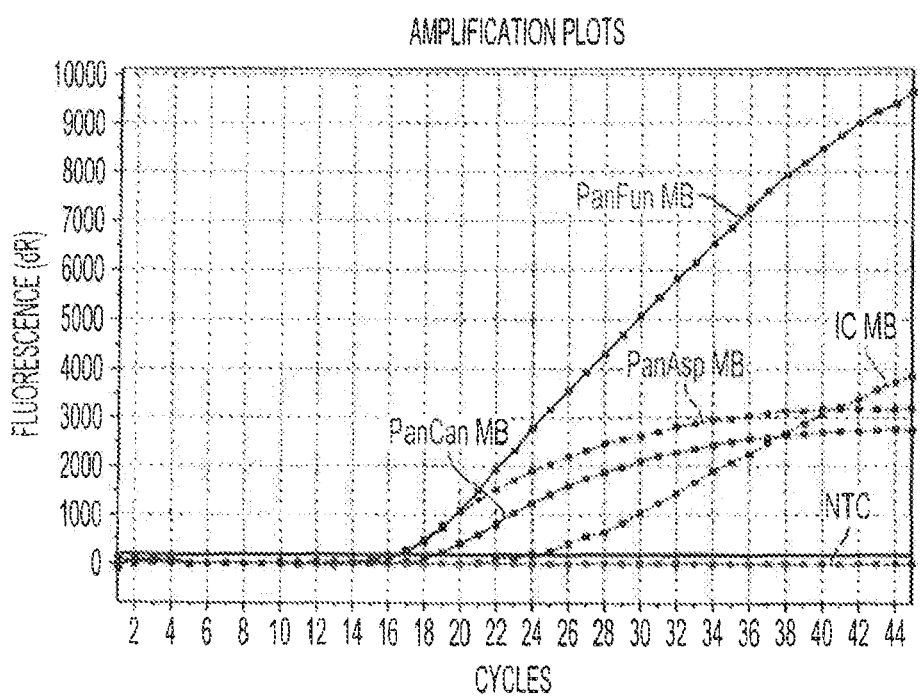
FIG. 2 shows the detection of *Candida* (PanCan), *Aspergillus* (PanAsp) and fungal (PanFun) DNA together with an internal control (IC) in a multiplex reaction.

Fluorescence signals coming from Stratagene Mx4000 System during PCR amplification were monitored using Mx4000 software in real time. At the end of each run, the amplification plots data were converted to graphic format and stored as image files or exported into Microsoft Office Excel and stored as spreadsheet files. Total changes in fluorescence for individual fluorophores (Rpost–Rpre) were taken as values for analysis. Results were converted to graphic or numerical format and stored as image or spreadsheet files. A summary of the results is shown in FIG. 2.

Example 4

Multiplex Detection of *Aspergillus* and *Pneumocytsis* DNA

A real-time amplification assay was carried out for the detection of *Aspergillus, Pneumocystis* (PCP) and panfungal (presence of any fungal) DNA using primers and probes described in Table 1, I (SEQ ID NOs: 2 to 4), IV (SEQ ID NOs: 15 to 17) and V (SEQ ID NOs: 19 to 21), together with an assay for the presence of the Internal Control DNA using the primers and probes described in Table 1, III (SEQ ID NOs: 11 to 13).

Fluorophores were conjugated to the beacon probes to allow detection. The fluorophores used are shown in Table 4.

TABLE 4

| Beacon probe | Fluorophore |
|---|---|
| The fluorophores used to label each molecular beacon probe | |
| *Aspergillus* | HEX (hexachlorofluorescein phosphoramidite) |
| *Pneumocystis* | FAM (carboxyfluorescein) |
| Panfungal | Cy ®5 (a registered trade mark of GE Lifesciences. FIG. 11 shows the structure of Cy5 mono NHS ester) |
| Internal Control | Texas Red ® (registered trade mark of Molecular Probes, Inc. FIG. 12 shows the structure of Texas Red sulphonyl chloride). |

The assay included DNA amplification by the polymerase chain reaction (PCR) with real-time detection utilizing molecular beacon probes. DNA from multiple fungal species were tested, together with a DNA-template free negative control.

Real-time PCR experiments were performed on Stratagene Mx4000 Multiplex Quantitative PCR System using the "Quantitative PCR (Multiple Standards)" setting. Eurogentec qPCR MasterMix No ROX Kit was used for all reactions. Each 50111 PCR reaction contained, 1× pPCR MasterMix with 4 mM $MgCl_2$, 20 pmol of each molecular beacon, 10-20 pmol of each primer and up to 100 ng of each DNA or water for the no template control. PCR reactions were performed using the parameters, as follows: 1 cycle of 10 min at 95° C., 45 cycles of 30 sat 95° C., 30 s at 50° C. and 30 s at 72° C. The fluorescence was measured 30 times during the annealing step.

Figure 3:
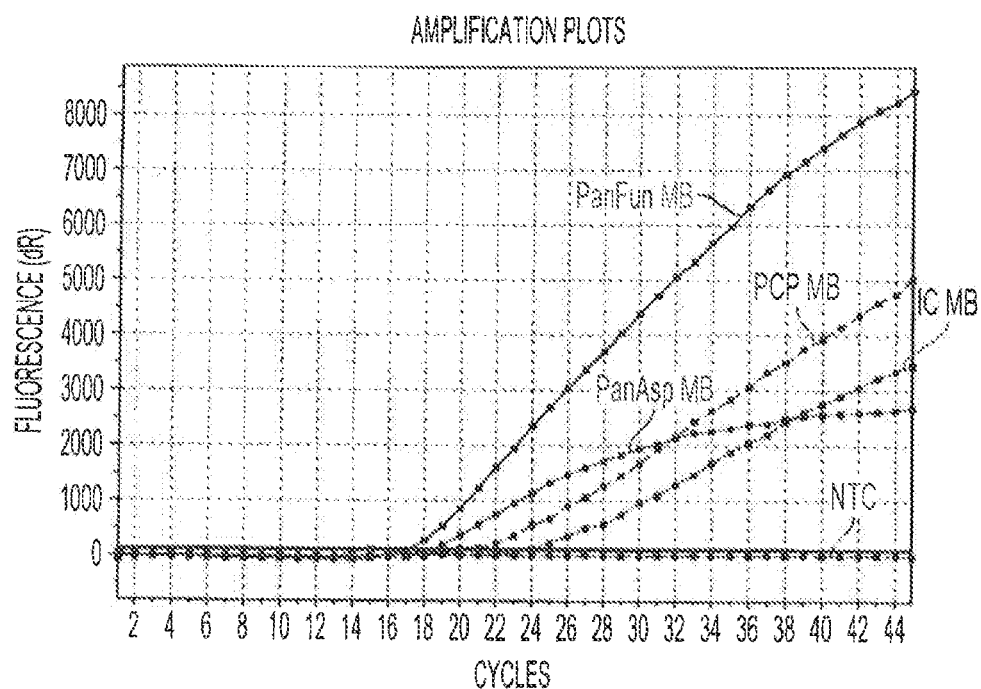
FIG. 3 shows the detection of *Pneumocystis* (PCP), *Aspergillus* (PanAsp) and any fungal (PanFun) DNA together with an internal control (IC) in a multiplex reaction.

Fluorescence signals coming from Stratagene Mx4000 System during PCR amplification were monitored using Mx4000 software in real time. At the end of each run, the amplification plots data were converted to graphic format and stored as image files or exported into Microsoft Office Excel and stored as spreadsheet files. Total changes in fluorescence for individual fluorophores (Rpost–Rpre) were taken as values for analysis. Results were converted to graphic or numerical format and stored as image or spreadsheet files. A summary of the results is shown in FIG. 3.

Example 5

Detection of Fungus in Non-Biological Samples

A real-time amplification assay was carried out for the detection of panfungal (presence of any fungal) DNA using primers and probes described in Table 1, I (SEQ ID NOs: 2 to 4). Nine samples of water were taken from various rooms throughout a Hospital and were tested together with sterilized laboratory water, a positive (extracted *Aspergillus* genomic DNA) and negative (sterile PBS) control.

The procedure was as follows. Real-time PCR experiments were performed on a Stratagene Mx4000 Multiplex Quantitative PCR System using the "Quantitative PCR (Multiple Standards)" setting. Reagents from Eurogentec (Liege, Belgium) were used for all reactions. Each 50-µl PCR reaction contained 1× Eurogentec reaction buffer, 0.2 µM of molecular beacon probe (Ib, SEQ ID NO: 3), 0.25 µM of each of the primers of Ia shown in Table 1 (SEQ ID NOs: 1 and 2), 1.25 U of HotGoldStart Taq DNA polymerase (Eurogentec, Liege, Belgium), 0.4 mM dNTPs, 5 mM $MgCl_2$ between 10 pg and 100 ng of fungal chromosomal DNA. Real-time PCR thermal cycler parameters were: 1 cycle of 10 min at 95° C., 45 cycles of 30 s at 95° C., 30 s at 50° C. and 30 s at 72° C. The filter gain set of the Mx4000 System was changed to FAM-960. The fluorescence was measured 3 times during the annealing step.

Figure 4:
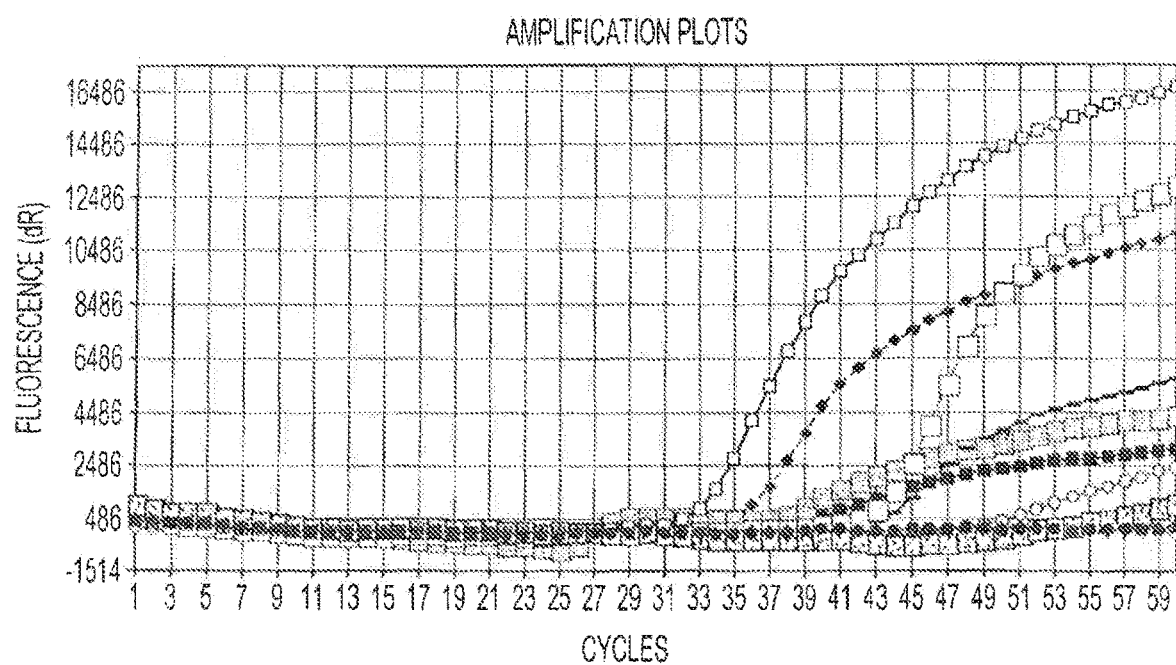
FIG. 4 shows the detection of fungal DNA in various water samples from a Hospital.

Fluorescence signals coming from Stratagene Mx4000 System during PCR amplification were monitored using Mx4000 software in real time. At the end of each run, the amplification plots data were converted to graphic format and stored as image files or exported into Microsoft Office Excel and stored as spreadsheet files. Total changes in fluorescence for individual fluorophores (Rpost–Rpre) were taken as values for analysis. Results were converted to graphic or numerical format and stored as image or spreadsheet files. A summary of the results is shown in Table 5 and FIG. 4.

TABLE 5

A summary of the results of a real time PCR experiment using panfungal primers and molecular beacon probes (Ia and Ib (SEQ ID NOs: 2 to 4) in Table 1) to detect panfungal DNA in a variety of Hospital water samples.

| Well | Assay | Well Type | Threshold (dR) | Ct (dR) | Sample no. | Sample type |
|------|-------|-----------|----------------|---------|------------|-------------|
| D4 | FAM | Unknown | 833.626 | 52 | 1 | Room 16, patient bathroom |
| D5 | FAM | Unknown | 833.626 | 41.52 | 2 | Room 9, patient bathroom |
| D6 | FAM | Unknown | 833.626 | No Ct | 3 | Hepa room 19, patient bathroom |
| D7 | FAM | Unknown | 833.626 | 35.78 | 4 | Room 2, patient bathroom |
| D8 | FAM | Unknown | 833.626 | 38.8 | 5 | Procedure room outpatient area |
| D9 | FAM | Unknown | 833.626 | No Ct | 6 | Main kitchen |
| E4 | FAM | Unknown | 833.626 | 44.35 | 7 | Stores Basement Sluice |
| E5 | FAM | Unknown | 833.626 | 43.05 | 8 | Ward 1 kitchen |
| E6 | FAM | Unknown | 833.626 | 58.74 | 9 | May Draper Tea bar |
| E7 | FAM | Unknown | 833.626 | No Ct | control | Wythenshawe ERC lab |
| E8 | FAM | Unknown | 833.626 | 33 | control | Positive |
| E9 | FAM | NTC | 833.626 | No Ct | control | Negative |

Example 6

Detection of Specific Species of *Candida*

Experiments were performed as discussed above for Examples 2 to 5.

Figure 6:
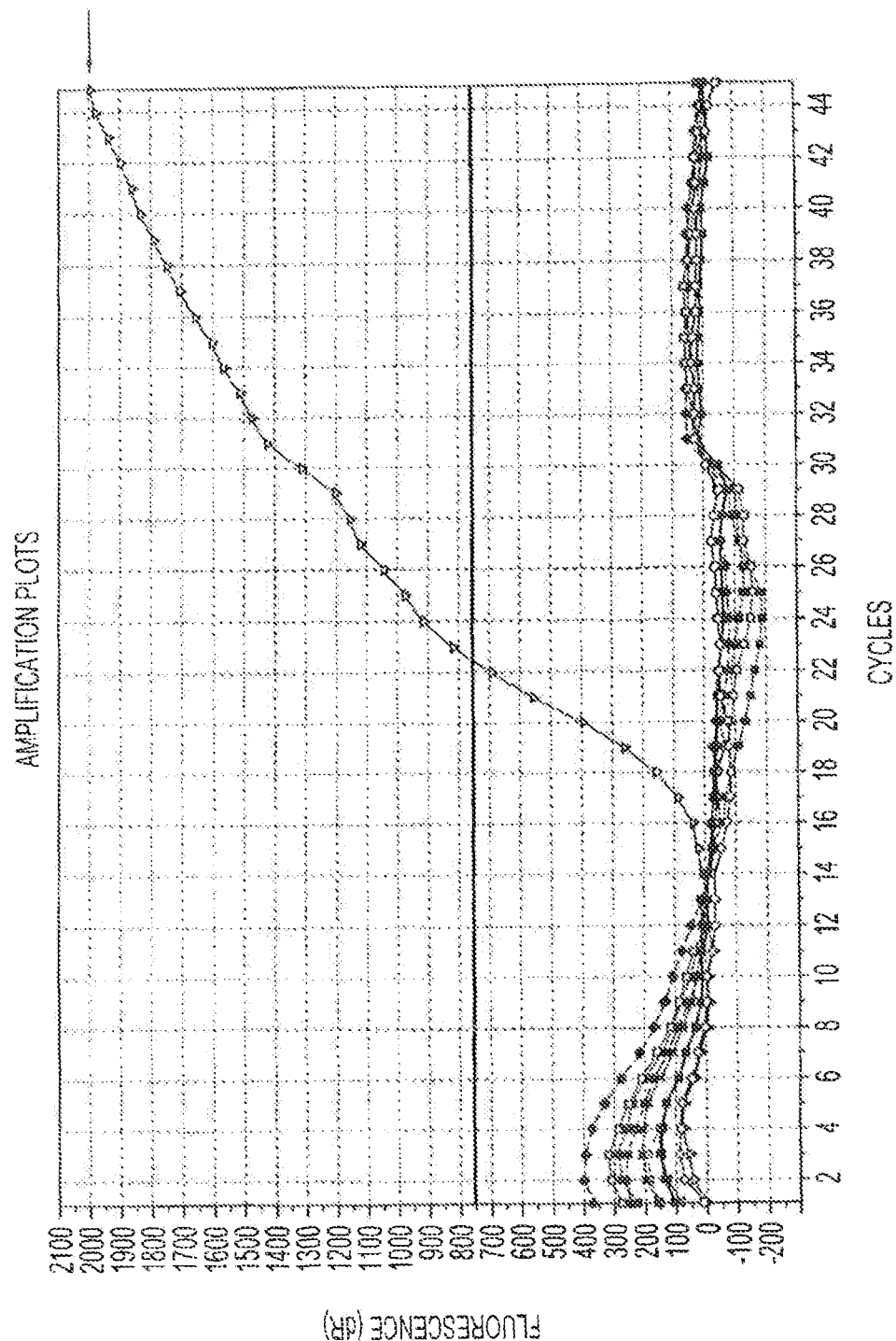
FIG. 6 shows the specific detection of *Candida tropicalis* DNA (see arrow) in a multiplex reaction.

A real-time amplification assay was carried out for the detection of *Candida tropicalis* using primers and probes described in Table 1, VI (SEQ ID NOs: 31 to 33). The other samples simultaneously tested in a multiplex reaction were DNA extracted from *Candida albicans, Candida krusei, Candida neoformans, Candida dubliniensis, Candida lusitaniae, Staphylococcus, Cerevisiae, Candida glabrata, Candida parapsilosis, Aspergillus fumigatus, Candida guilliermondii* and *Candida tropicalis* as well as water. A summary of the results is shown in FIG. 6.

Figure 7:
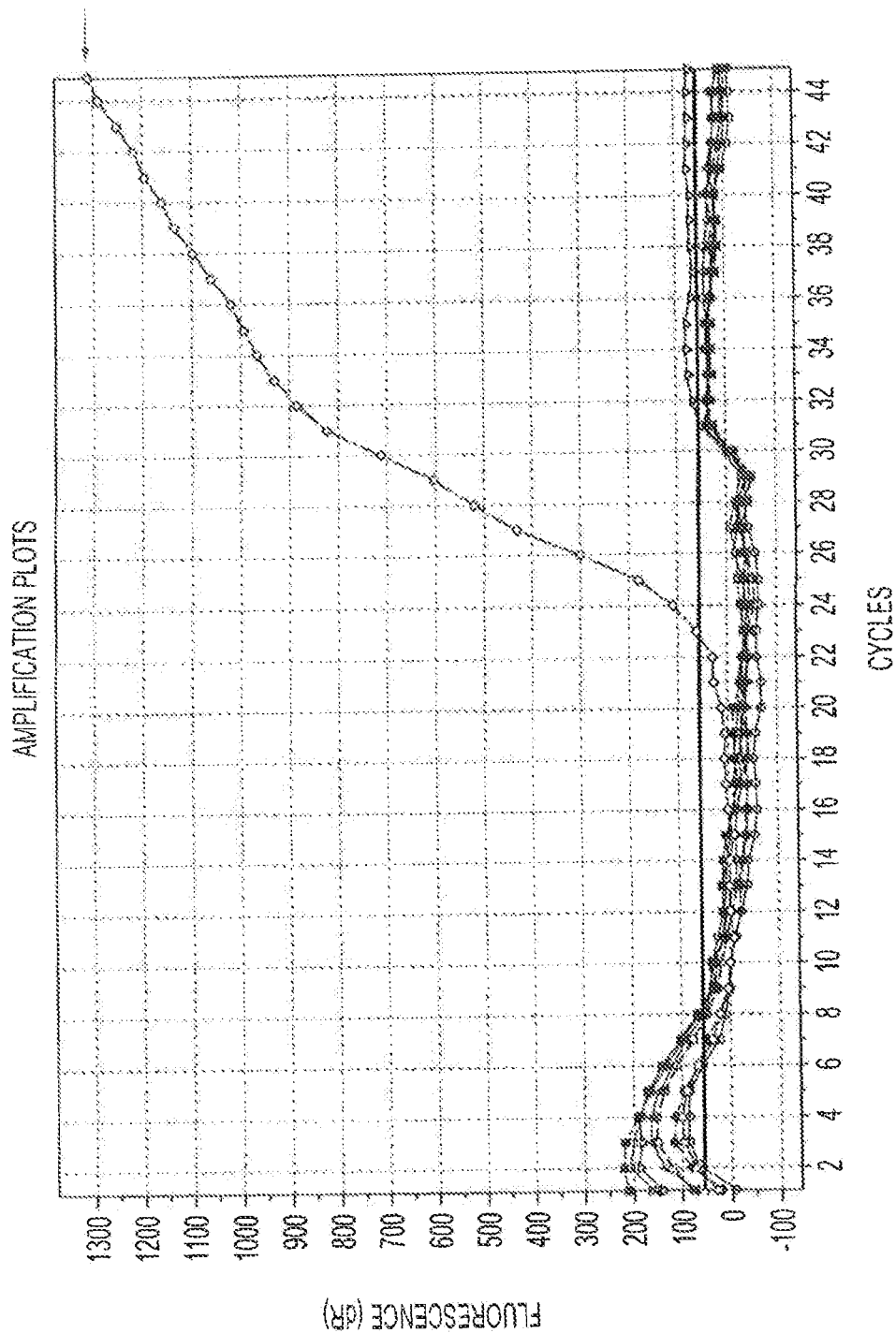
FIG. 7 shows the specific detection of *Candida parapsilosis* DNA (see arrow) in a multiplex reaction.

A real-time amplification assay was carried out for the detection of *Candida parapsilosis* using primers and probes described in Table 1, VII (SEQ ID NOs: 31, 32 and 35). The samples tested were the same as tested for *Candida tropicalis*. A summary of the results is shown in FIG. 7.

Figure 8:
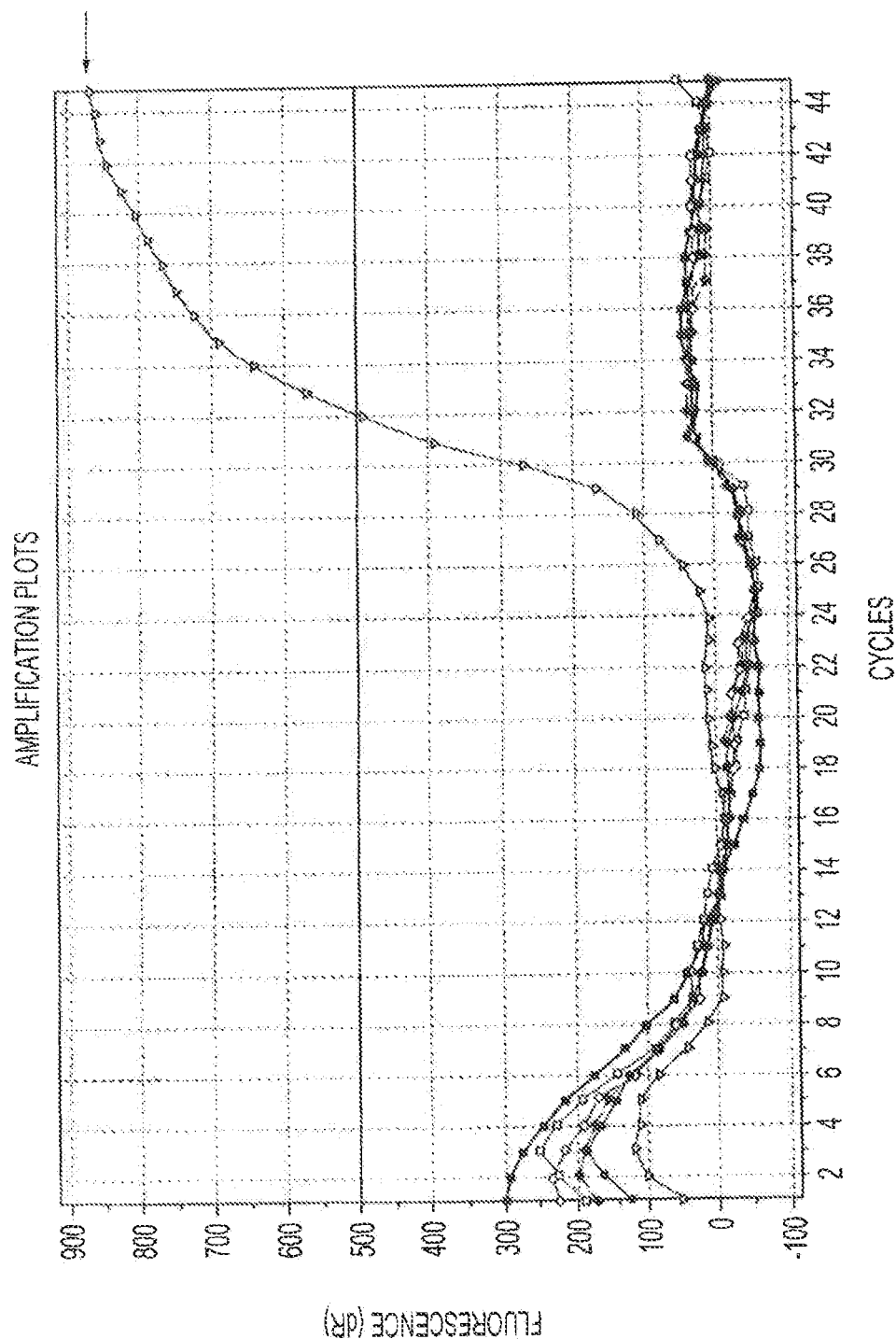
FIG. 8 shows the specific detection of *Candida albicans* DNA (see arrow) in a multiplex reaction.

A real-time amplification assay was carried out for the detection of *Candida albicans* using primers and probes described in Table 1, VIII (SEQ ID NOs: 31, 32 and 37). The samples tested were the same as tested for *Candida tropicalis*. A summary of the results is shown in FIG. 8.

Figure 9:
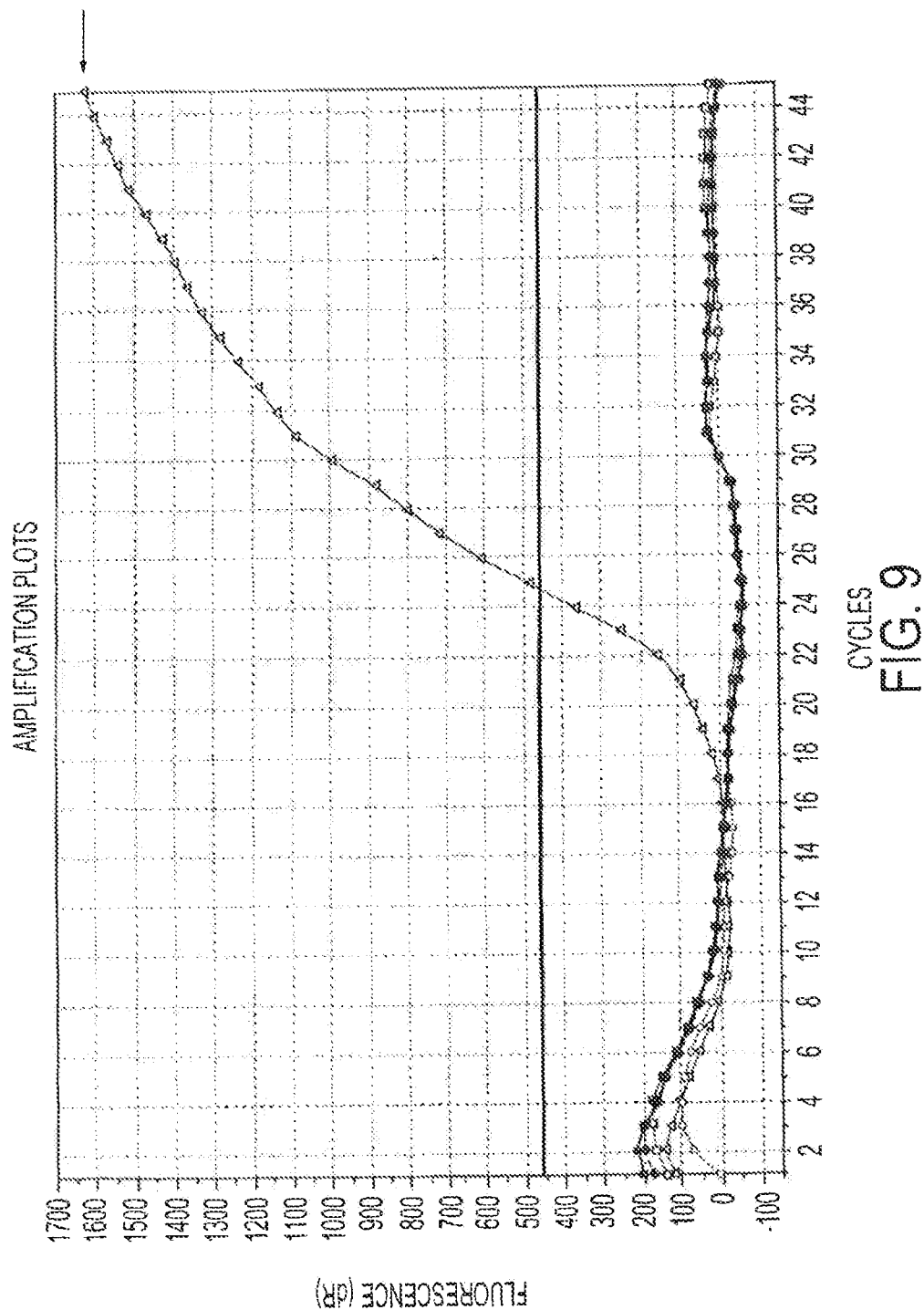
FIG. 9 shows the specific detection of *Candida glabrata* DNA (see arrow) in a multiplex reaction.

A real-time amplification assay was carried out for the detection of *Candida glabrata* using primers and probes described in Table 1, IX (SEQ ID NOs: 31, 32 and 39). The samples tested were the same as tested for *Candida tropicalis*. A summary of the results is shown in FIG. 9.

Figure 10:
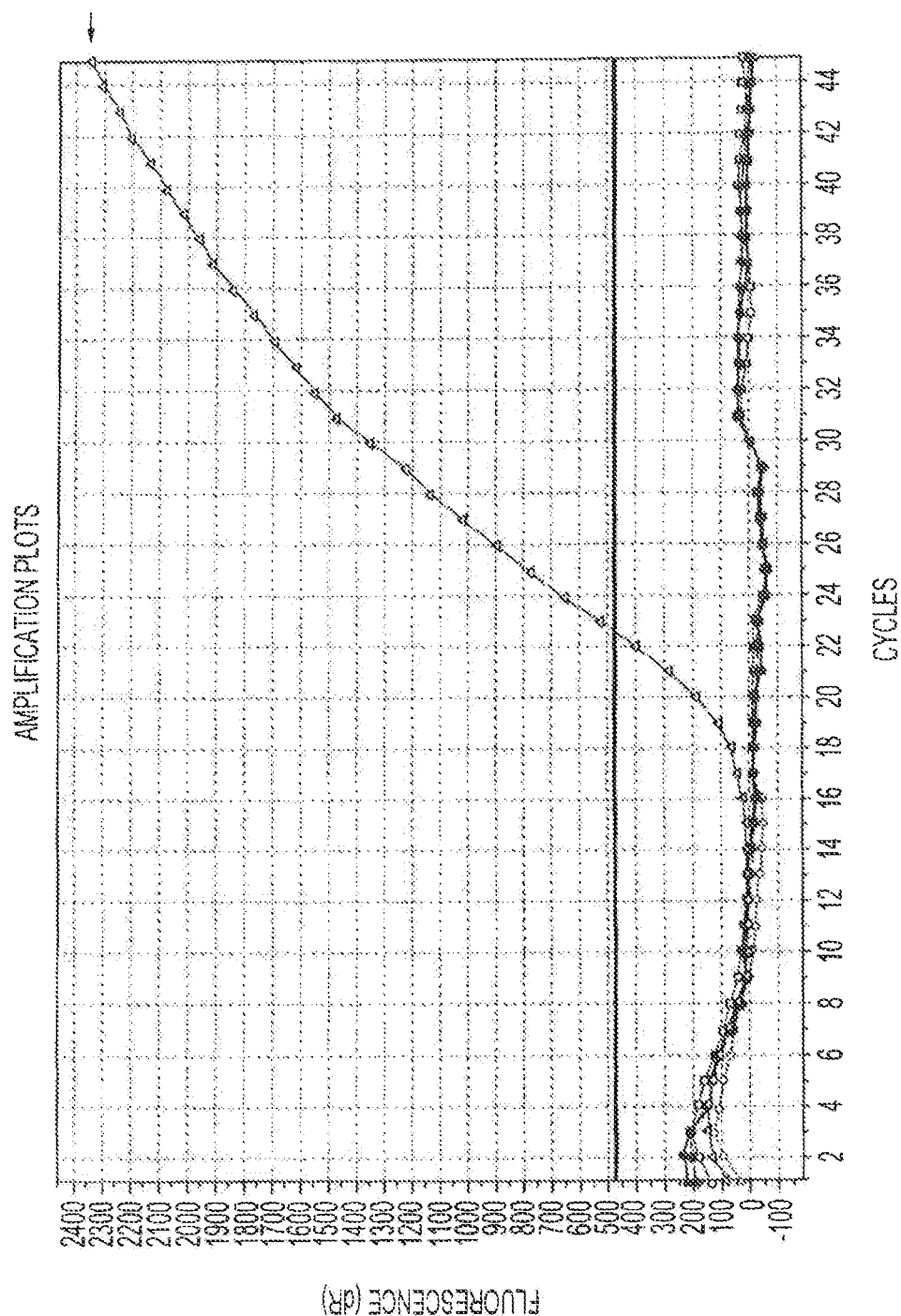
FIG. 10 shows the specific detection of *Candida krusei* DNA (see arrow) in a multiplex reaction.

A real-time amplification assay was carried out for the detection of *Candida krusei* using primers and probes described in Table 1, X (SEQ ID NOs: 31, 32 and 43). The samples tested were the same as tested for *Candida tropicalis*. A summary of the results is shown in FIG. 10.

It is understood that the present invention is not limited to the preferred embodiments and examples presented herein, which serve only to illustrate certain aspects of the invention to one of ordinary skill in the art. Other embodiments of the invention, which would be apparent to those of ordinary skill, are considered to fall within the scope and spirit of the invention.

Example 7

Use of Four Color Multiplex Molecular Beacon Probes for the Detection of Fungal Pathogens and an Internal Control A four color multiplex approach for the detection of pathogenic fungi and an internal control was developed for real time quantitative PCR with molecular beacon probes. The multiplex panel included the detection of all fungi (panfungal), all *Candida* species (pan*Candida*), all *Apspergillus* species (pan*Aspergillus*) and a novel non-human and non-fungal internal control DNA sequence (internal control).

To enhance detection sensitivity for the pan*Aspergillus* probe, two new primers were designed (SEQ ID Nos 46 and 47) and new target regions in the 18S ribosomal gene were also identified that had broad panfungal coverage. Using these regions, primers, denoted as "v.2" and "v.3," and molecular beacons, denoted as "v.2.3" and "v.3.3," were designed. See Tables 6 and 7 below.

Two panels of four color multiplex probes were employed using either Panfungal v2.3 or v.3.3 plus the internal control, pan*Candida* and pan*Aspergillus*. Each panel was evaluated using a variety of target genomic DNA to assess the multiplex specificity.

Real-time PCR experiments were performed on a Stratagene Mx4000 Multiplex Quantitative PCR System using the "Quantitative PCR (Multiple Standards)" setting. Eurogentec qPCR MasterMix No ROX Kit was used for all reactions. Each 50 µl PCR reaction contained, 1× pPCR MasterMix with 4 mM MgCl$_2$, 20 pmol of each molecular beacon, 10-20 pmol of each primer and up to 100 ng of each DNA or water for the no template control. PCR reactions were performed as follows: 1 cycle of 10 min at 95° C., 45 cycles of 30 s at 95° C., 30 s at 50° C. and 30 s at 72° C. The fluorescence was measured 30 times during the annealing step.

Real time PCR was performed with the two multiplex panels using a single template to evaluate each panel's specificity. *A. fumigatus, C. albicans, C. neoformans, R. oryzae, S. aureus* and *Z. mays* genomic DNA were used as templates for this assay.

TABLE 6

Molecular beacon probes

| Molecular Beacon Probe | 5' Reporter Dye | 3' Quencher | Oligonucleotide sequence |
|---|---|---|---|
| panCandida (PanCan) (SEQ ID NO: 8) | HEX | DABCYL | cgcgatGATGATTCATAATAACTTTTC Gatcgcg |
| panAspergillus (PanAsp) (SEQ ID NO: 17) | FAM | DABCYL | cgcgatAGTTGAACCTTGGGTCTGGCa tcgcg |
| panfungal (PanFunv2.3) (SEQ ID NO: 44) | Cy5 | DABCYL | ccgtggCTGCGGCTTAATTTGACTCAc cacgg |
| panfungal (PanFunv3.3) (SEQ ID NO: 45) | Cy5 | DABCYL | cgcgacACATCCAAGGAAGGCAGCAGg tcgcg |
| Internal Control (IC) | Texas Red | DABCYL | cgcacgCAATCCTGAGCCAAATCCCTc gtgcg |

TABLE 7

Real time PCR primers

| Primer Name | Direction | 5'-3' Sequence |
|---|---|---|
| PanCandida (SEQ ID NO: 6) | sense | TAGATAAAAAATCAATGCCTTCGG (SEQ ID NO: 6) |
| | antisense | CATGGTAGGCCACTATCCTAC (SEQ ID NO: 7) |
| PanAspergillus v.1.3 | sense | TAATTCCAGCTCCAATAGCG (SEQ ID NO: 46) |
| | antisense | CCAGAAGGAAAGGTCCAGCC (SEQ ID NO: 47) |
| PanFungal v.2 | sense | AATTGACGGAAGGGCACCAC (SEQ ID NO: 48) |
| | antisense | TGTCTGGACCTGGTGAGTTT (SEQ ID NO: 49) |
| PanFungal v.3 | sense | AGAGGGAGCCTGAGAAACGG (SEQ ID NO: 50) |
| | antisense | CGGCTGCTGGCACCAGACTT (SEQ ID NO: 51) |
| Internal Control | sense | CCTGCTAAGTGGTAACTTCC (SEQ ID NO: 11) |
| | antisense | TGAGTCTCTGCACCTATCCT (SEQ ID NO: 12) |

FIG. 13 provides graphical displays of real-time PCR results from multiplex panel experiments.

Real-time PCR experiments were performed on a Stratagene Mx4000 Multiplex Quantitative PCR System using the "Quantitative PCR (Multiple Standards)" setting. Stratagene Brilliant QPCR MasterMix was used for all reactions. Each 25-µl PCR reaction contained 1× QPCR MasterMix with 5.5 mM MgCl$_2$, 5 pmol of each molecular beacon, 10 pmol of each primer and up to 100 ng of each DNA or water for the no template control. PCR reactions were performed as follows: 1 cycle of 10 min at 95° C., 45 cycles of 30 s at 95° C., 30 s at 50° C. and 30 s at 72° C. The fluorescence was measured 3 times during the annealing step.

The two panfungal probes assayed in simplex reactions identified a panel of diverse fungal DNA (n=21) that included Zygomycetes. Both probes also detected signal from water containing Ochronis gallopavum and respiratory samples from patients which did not grow various human pathogenic fungi, suggesting increased sensitivity of detection. The panAspergillus primers increased the detection sensitivity by at least 10-fold when compared to earlier primers in a multiplex primer assay that contained the PanAsp beacon and all the primers in the multiplex. The panCandida probe produced lower fluorescence than other beacons as a result of incorrect gain settings on the HEX detection channel of the Stratagene instrument. In general, the specific assays in both multiplex panels effectively detected their respective analytes, confirming the functionality of each multiplex panel.

Example 8

Multiplex Detection of Aspergillus and Pnemocytis Jirovecii

A real-time amplification assay was designed to simultaneously detect numerous Aspergillus species, Pneumocystis jirovecii and an internal control. The assay included DNA amplification by the polymerase chain reaction (PCR) with real-time detection utilizing molecular beacon probes. In particular, the primers and probes described in Tables 8-9 were employed using these amplification and detection conditions. The setup required a total volume of 25 uL, of which 5 uL was clinical sample, positive or negative control. The Positive Control molecule was a recombinant plasmid harboring the Aspergillus and Pneumocystis target sequences. The microtitre tray was prepared in a PCR hood and run on an AB7500 thermocycler using the following run conditions: a single cycle of 95° C. for 10 min then 95° C. for 30 sec, 60° C. for 1 min and 72° C. for 30 sec, for 40 cycles. The threshold setting was set at 0.2 for Aspergillus, at 0.1 for Pneumocystis and IAC.

The Aspergillus DNA template lies within the 18S region, which has 35-90 copies per genome. The template is common to all Aspergillus genus and possesses little overlap with other fungal pathogens. The P. jirovecii DNA template lies within the Mitchondrial Large Sub Unit.

TABLE 8

Molecular beacon probes

| Molecular Beacon Probe | 5' Reporter Dye | 3' Quencher | Oligonucleotide sequence |
|---|---|---|---|
| *Aspergillus* Beacon | FAM | DDQ1 | CGCGATAGTTGAACCTTGGGTCTGGCATCGCG (SEQ ID NO: 17) |
| *Pneumocystis* Beacon | HEX | DDQ1 | CGCAGCCTAGGATATAGCTGGTTTTCTGCGCTGC (SEQ ID NO: 21) |
| Internal Control Beacon | Atto647N | DDQ1 | CGCACGCAATCCTGAGCCAAATCCCTCGTGCG (SEQ ID NO: 13) |

DDQ1 = Deep Dark Quencher 1

TABLE 9

Amplification primers

| Primer Name | Direction | 5'-3' Sequence |
|---|---|---|
| *Aspergillus* primer, sense | Sense | GGTAATTCCAGCTCCAATAGC (SEQ ID NO: 15) |
| *Aspergillus* primer, antisense | Antisense | GGCCTGCTTTGAACACTCTAA (SEQ ID NO: 16) |
| *Pneumocystis* primer, sense | Sense | GCAAAGfACTCAGAAGAATTGTGG (SEQ ID NO: 19) |
| *Pneumocystis* primer, antisense | Antisense | TCCCTCGAGATATTCAGTGC (SEQ ID NO: 20) |
| Internal control primer, sense | Sense | CCTGCTAAGTGGTAACTTCC (SEQ ID NO:11) |
| Internal control primer, antisense | Antisense | TGAGTCTCTGCACCTATCCT (SEQ ID NO: 12) |

Sample Processing

Fungal DNA from clinical respiratory (and in some cases, other) samples were obtained from clinical collaborators. The samples had been stored in most instances for a number of years, either as the clinical specimens or as DNA. A small number of samples were collected prospectively. Where DNA had not been extracted from the samples, this was achieved using MycXtra™ Fungal DNA Extraction Kit (Myconostica, Manchester, UK) containing resin beads.

The methods used in each centre for microscopy and culture of BAL are summarized in the table below. The samples from Manchester were taken as part of a research study with informed consent but processed by standard microbiology procedures.

TABLE 10

Bronchoalveolar lavage fluid (BAL) Processing

| Primary processing | Innsbruck Class 2 hood | Lausanne Class 2 hood | Leuven Class 2 hood | Manchester CL3 laboratory + class 1 hood |
|---|---|---|---|---|
| Microscopy for fungi | All BALs | Yes when requested | Only on request | yes (gram stain only) |
| Volume used | 1 drop | 50-250 uL | 0.4 mL | 1 drop |
| Centrifuged? | 15 000 g/5 min; resuspend | Cytocentrifugation | Yes, cytocentrifuge | yes |
| Method | Calcoflour White | GMS | Fungi-FluorTM Kit | gram stain |
| PCP method | Calcafluor | GMS | Yes, if urgent, Immy kit | GMS stain (histopathology) |
| Volume Used | | 50-250 ul | | |
| Centrifuged? | 15 000 g/5 min; Resuspend in 5 mL | Cytocentrifugation | | |
| Fungal culture | | | Yes if req, or yeast/hyphae seen | All |
| Volume used | 1-5 mL | 5 mL | 1-2 drops | 2-3 drops |
| Centrifuged? | 15 000 g/5 min; resuspend | 3000 rpm (2000 g) × 10 min | No | Yes 3000 rpm/5 mins |
| Medium 1 | Sabouraud + Cloramphenicol | Sabouraud | Sabouraud + chloramphenicol | Sabouraud + chloramphenicol |
| Medium 2 | Brain heart Infusion | | | |

TABLE 10-continued

Bronchoalveolar lavage fluid (BAL) Processing

| Primary processing | Innsbruck Class 2 hood | Lausanne Class 2 hood | Leuven Class 2 hood | Manchester CL3 laboratory + class 1 hood |
|---|---|---|---|---|
| Medium 3 Plate or slant? | Malt exract | Plate | Slant | Slant |
| Temperature(s) | 30 C., 37 C. | 30 C. | 35-37 C. for 48 hrs then 30 C. | 30 C. for 10 days |

As can be seen, the method of sample handling varied by centre. Both the volume of BAL used for standard and *Pneumocystis* microscopy and fungal culture varied, as well. For example, Innsbruck, Lausanne and Manchester used a centrifugation step prior to fungal culture, whereas Leuven did not. These differences may account for some of the differences in yield observed. At the Leuven site, 800 µL of sample was used for DNA extraction with the MycXtra™ kit, and there was no initial centrifugation step to collect and concentrate fungal cells. Once extracted, nucleic acid from each sample was shipped and stored at −80° C. prior to testing.

Specificity

Table 11 provides the results of cross reactivity testing using a variety of fungi.

| Organism | Aspergillus Channel | Pneumocystis Channel |
|---|---|---|
| Aspergillus fumigates | 2/2 | 0/2 |
| Aspergillus niger | 10/10 | 0/9 |
| Aspergillus terreus | 6/6 | 0/6 |
| Aspergillus nidulans | 3/3 | 0/3 |
| Aspergillusflavus | 2/2 | 0/2 |
| Aspergillus versicolor | 2/2 | 0/2 |
| Aspergillus glaucus | 1/1 | 0/1 |
| Aspergillus tubingensis | 2/2 | 0/2 |
| Aspergillus foetidus | 2/2 | 0/2 |
| All Aspergillus | 30/30 | 0/30 |
| Penicillium notatum | 1/1 | 0/1 |
| Penicillium spp. | 3/3 | 0/3 |
| All Penicillium | 4/4 | 0/4 |
| Fusarium solani | 1/1 | 1/1 |
| Fusarium dimerium | 1/1 | 0/1 |
| All Fusarium | 2/2 | 1/2 |
| Cladosporium spp, | 1/1 | 0/1 |
| Alternaria alternaria | 0/1 | 0/1 |
| Rhizomucor pusillus | 0/1 | 0/1 |
| Scedosporium prolificans | 0/1 | 0/1 |
| Candida albicans | 0/5 | 0/5 |
| Candida glabrata | 0/3 | 0/3 |
| Candida tropicalis | 0/1 | 0/1 |
| Candida krusei | 0/3 | 0/3 |
| Candida parapsilosis | 0/5 | 0/5 |
| Candida sake | 0/2 | 0/2 |
| Candida novogenesis | 0/1 | 0/1 |
| Candida kefyr | 0/2 | 0/2 |
| Candida rugosa | 0/2 | 0/2 |
| Candida inconspicua | 0/2 | 0/2 |
| Candida humicola | 0/1 | 0/1 |
| All Candida | 0/27 | 0/27 |
| Trichosporon cutaneum | 1/3 | 0/3 |
| Trichosporon asahii | 0/1 | 0/1 |
| Trichosporon mucoides | 0/1 | 0/1 |
| All Trichosporon | 1/5 | 0/5 |
| Sporothrix schenkii | 1/2 | 0/2 |
| Saccharomyces cerevisiae | 0/5 | 0/5 |
| Cryptococcus neoformans | 0/7 | 0/7 |
| Rhodotorula rubrum | 0/2 | 0/2 |
| Blastoschizomyces capitatus | 0/2 | 0/2 |
| Geotrichum candidum | 0/1 | 0/1 |
| Viral DNA | 0/7 | 0/7 |

-continued

| Organism | Aspergillus Channel | Pneumocystis Channel |
|---|---|---|
| Bacterial DNA | 0/3 | 0/3 |
| Human DNA | 0/1 | 0/1 |

Sensitivity

Figure 14:
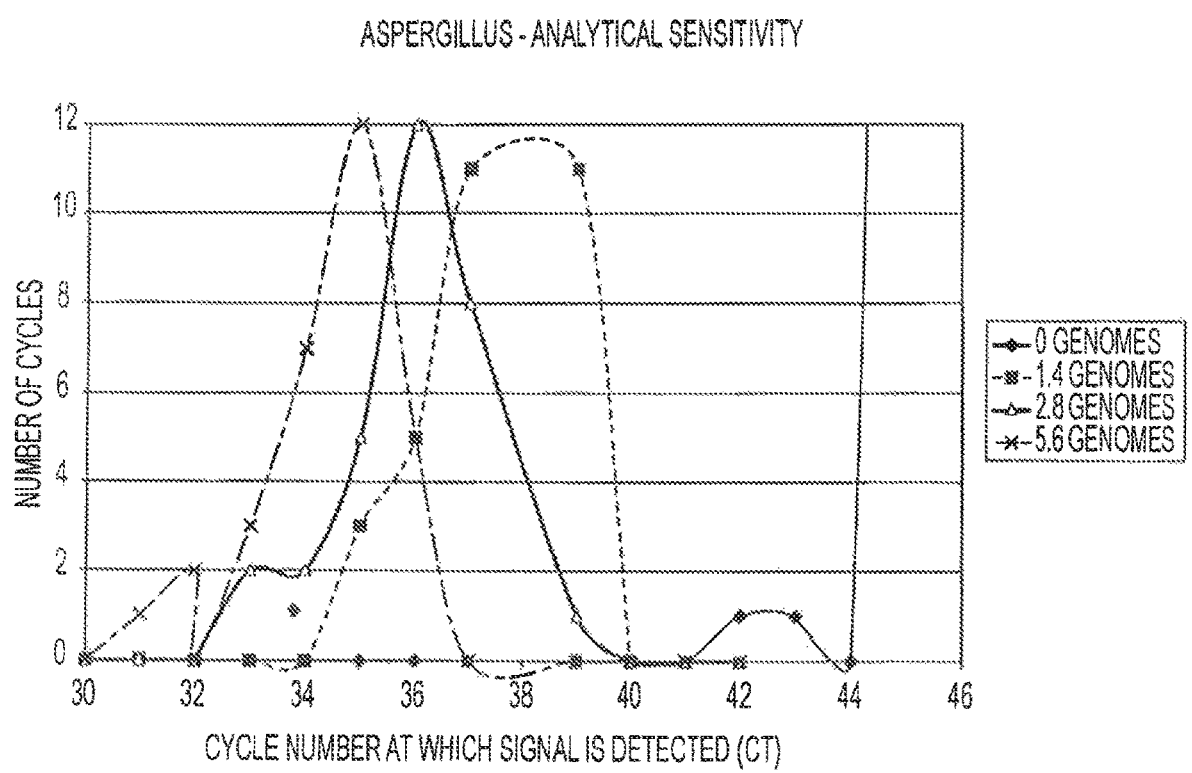
FIG. 14 shows the Limit of Detection for *Aspergillus* for a multiplex assay designed to detect *Aspergillus* genus, *Pneumocystis jirovecii* and an internal control.

Analytical Sensitivity for *Aspergillus* was determined using quantified DNA extracted from *A. fumigatus* A293. FIG. 14 shows that a Limit of Detection of one genomecopy can be obtained using standard methodology (CLSI EP17-A—"Protocols for Determination of Limits of Detection and Limits of Quantitation").

Figure 15:
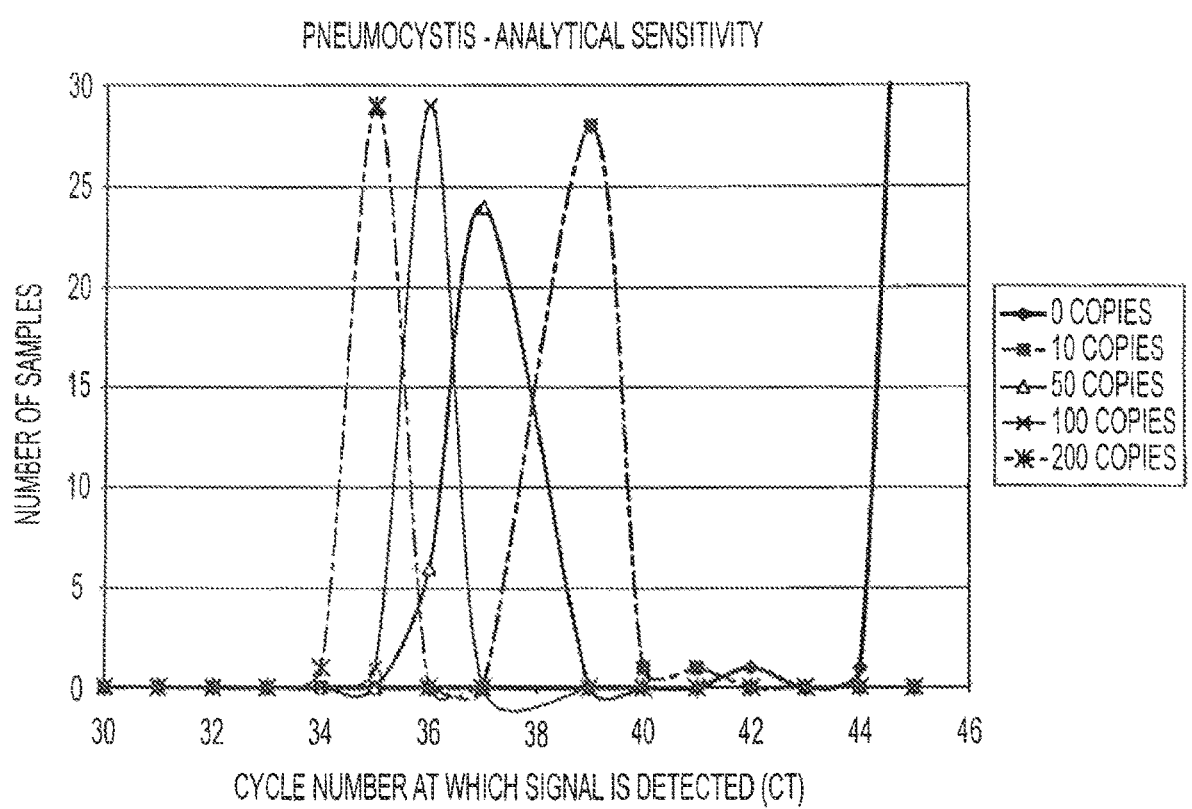
FIG. 15 shows the Limit of Detection for *Pneumocystis* for a multiplex assay designed to detect *Aspergillus* genus, *Pneumocystis jirovecii* and an internal control.

Analytical Sensitivity for *Pneumocystis* was determined using quantified recombinant plasmid DNA. FIG. 15 shows that a Limit of Detection of six target copies can be obtained using standard methodology (CLSI EP 17-A—"Protocols for Determination of Limits of Detection and Limits of Quantitation"). The target is a multicopy gene, but the number of copies within the genome, and therefore the per-organism detection limit is unknown.

Table 12 provides the sensitivity and limit of detection for these primers and probes.

TABLE 12

| | Limit of Detection (Ct) | Target number equivalent |
|---|---|---|
| Aspergillus fumigatus | 38.6 | 34 |
| Pneumocystis jirovecii | 38.5 | 6 |

The value for the *Aspergillus* target was determined using the A293 strain of *Aspergillus fumigatus* from which the genome has been fully sequenced. It is known there are 37 copies of the target within the genome, determined by optical mapping and thus 34 target copies represent approximately 1 genome copy.

The value for the *Pneumocystis* target was determined using a recombinant DNA plasmid harbouring the target sequence. As the *Pneumocystis* target sequence is a mitochondrial target, there will be numerous copies per cell, but it not known how many. For comparison there are 13 mitochondrial genomes per *A. fumigatus* nuclear genome (in AF293) and an unknown number of subunit repeat sequences per mitochondrion in *Pneumocystis jirovecii*.

Internal Amplification Control

There was some preliminary evidence of the introduction of a low-level inhibitor into the reaction from the extraction process. This was overcome with a smaller eluate volume in the FXG assay. Therefore in order to assess the effect of altering the amount of sample included in the reaction, the Internal Amplification Control values of the samples were examined and compared. The reproducibility of the internal amplification control was determined in 32 assays conducted in 6 experiments (table below). The cut-off was taken as +/3 standard deviations from the mean (Ct=32-36.2).

TABLE 13

| Mean | SD | 3 × SD | Range Min | Max |
|---|---|---|---|---|
| 34.58 | 0.54 | 1.61 | 33.0 | 36.2 |

In the tests of the clinical samples where 5)11_, of sample was added to the reaction, only 26 samples of 399 (5.8%) were out of range, 2 with a low Ct value and 24 with an elevated Ct value indication PCR inhibition. 13 of these showed complete inhibition of PCR (recorded as a Ct of 41 for the purposes of analysis). The mean Ct value for the 399 samples assayed was 34.68+/−1.42.

In the tests where 2 μL of sample was added to the reaction, only 2 of the Internal Amplification Control results were outside of the allowed range. In both cases the Ct value was lower than the range (i.e. not due to inhibition). No sample demonstrating inhibition was identified with the 2 μL test.

Both samples with low Ct values, consistent with an accelerated PCR reaction, were from Lausanne, and this result was seen in both 2 μL and 5 μL reactions. The nature of this accelerated reaction was not determined.

Overall, the 50 μL volume was selected for further analysis, based on the demonstration of inhibition in clinical samples and inspection of the clinical results and their correlation with culture and microscopy.

*Pneumocystis* Results

The results were analyzed as follows: (i) samples which had an internal amplification control (IAC) out of range were highlighted and removed; (ii) only those samples with microscopy results which were appropriate for the detection of *P. jirovecii* and/or those in whom the clinical diagnosis of *Pneumocystis* pneumonia was diagnosed were selected; (iii) PCR positive results were sorted by Ct value to assess lowest appropriate cut-off for positivity; and (iv) 2×2 table of results were constructed using microscopy (+2 clinically diagnosed cases) to determine the sensitivity, specificity, positive (PPV) and negative predictive (NPV) values. A secondary analysis of HIV/AIDS patients also was conducted to evaluate the cutoff value in these different populations.

A total of 190 results were analysed: 42 from patients with AIDS or HIV infection and 148 from other patients. The appropriate cutoff for positivity was determined to be at the limit of detection of the assay i.e. a Ct value of 38.5. Using this cutoff the results are shown in the following tables:

TABLE 14

| PCP AIDS and non-AIDS | | | | |
|---|---|---|---|---|
| | FXG PCR+ | FXG PCR− | total | % |
| *Pneumocystis* microscopy+ | 67 | 2 | 69 | 97.10 Sensitivity |
| *Pneumocystis* microscopy− | 16 | 105 | 121 | 86.78 Specificity |
| Total | 83 | 107 | 190 | |
| | 80.72 PPV | 98.13 NPV | | |

Ct values ranged from 23.55 to the limit of detection (38.5) indicative of a wide range of organism loads. It can be seen that the sensitivity of 97.1% is a good result with only 2 samples positive by microscopy not detected. The NPV is very high (98.13) consistent with a highly sensitive test. The specificity was not as high, as 16 samples showed positive results, but were microscopy negative and no clinical diagnosis of *Pneumocystis* pneumonia was made. This is consistent with the published literature indicating a higher sensitivity of PCR assays compared with microscopy, and with missed clinical diagnoses. One of the 2 samples which was negative was from a non-AIDS patient and the BAL was not centrifuged.

The data were separated into AIDS/HIV results and all others for further analysis.

TABLE 15

| PCP AIDS/HIV | | | | |
|---|---|---|---|---|
| | FXG PCR+ | FXG PCR− | | |
| *Pneumocystis* microscopy+ | 36 | 1 | 37 | 97.30 Sensitivity |
| *Pneumocystis* microscopy− | 1 | 4 | 5 | 80.00 Specificity |
| Total | 37 | 5 | 42 | |
| | 97.30 PPV | 80.00 NPV | | |

The performance of the test in AIDS patients was excellent, and higher Ct values were obtained in this group (24.57-34.93). The calculations for specificity and NPV are limited by only having 4 true negative samples for testing.

TABLE 16

| PCP non-AIDS/H1V | | | | |
|---|---|---|---|---|
| | FXG PCR+ | FXG PCR− | | |
| *Pneumocystis* microscopy+ | 31 | 1 | 32 | 96.88 Sensitivity |
| *Pneumocystis* microscopy− | 15 | 101 | 116 | 87.07 Specificity |
| Total | 48 | 100 | 148 | |
| | 67.39 PPV | 99.02 NPV | | |

In the non-AIDS patients a larger number of true negative samples were obtained, and the Ct range of positive results was greater (23.55-37.55). The sensitivity is high at 96.88, and the NPV is also high at 99.02.

The proposed interpretation criteria in the IFU will enable positive results to be reported, even if inhibition is detected (ie a raised IAC Ct value). These results were excluded from the tables above. Six *P. jirovecii* results fall into this category, and in 5 cases the microscopy was positive (Ct values of 21.06, 22.24, 25.18, 25.26, 33.53 and 35.91). The Ct values in these samples containing an inhibitor were generally low, and only the highest (35.91) was microscopy negative.

*Aspergillus* Results

The analysis steps were as follows: (i) results which had an internal amplification control (IAC) out of range were highlighted and removed, (ii) sample types were grouped into BAL centrifuged or not, other respiratory specimens (including sputum) and tissue/biopsy samples, (iii) only those results with positive culture results (respiratory samples) or culture or histology positive for tissue were selected, (iv) PCR positive results were sorted by Ct value to assess lowest appropriate cut-off for positivity, (v) 2×2 tables of results were constructed using culture results or histology positive samples to determine the sensitivity, specificity, positive (PPV) and negative predictive (NPV) values and (vi) results inspected to determine any possible impact of prior antifungal therapy on sensitivity.

The cut-off for positivity was determined by inspection of the data and was determined to be at the limit of detection (Ct 38.6). This cut-off was reinforced by examination of the 15 samples from Manchester from normal controls in which 2 has Ct values of 38.82 and 38.4. Very low levels of *Aspergillus* spp. are found in normal lungs and so a cut-off at this level is appropriate to detect a pathogen, which is found in small quantities even in severely ill patients. In fact the sample with a Ct value of 38.4 grew *Penicillium* spp. and another sample grew *A. fumigatus,* but was negative by the test assay. These data are consistent with very low levels of fungi in the lungs of normal people and indicate that the assay is operating at this level of detection.

Based on the IAC cut-off, 10 BAL samples (5 centrifuged and 5 uncentrifuged), 5 other respiratory samples and no tissue/biopsy samples were excluded from analysis because the IAC was out of range.

The results of the BAL samples centrifuged and non-centrifuged are shown below. Although there are slightly fewer samples and fewer positive samples in the uncentrifuged group, the impact of centrifugation as a preliminary step in extraction appears clear from these data. The sensitivity falls from 73% to 29%, although the specificity is essentially unchanged. On the basis of this analysis, only centrifuged BAL samples were included in the overall analysis. Centrifugation could account for the difference, but other factors could be relevant, including the patient population (large proportion of ICU patients), processing differences and storage factors.

TABLE 17

| BAL only (centrifuged) | | | | |
|---|---|---|---|---|
| | FXG PCR+ | FXG PCR− | | |
| *Aspergillus* culture +ve | 19 | 8 | 26 | 70.37 Sensitivity |
| *Aspergillus* culture −ye | 4 | 92 | 97 | 95.83 Specificity |
| | 23 | 100 | 123 | |
| | 82.61 PPV | 92.00 NPV | | |

TABLE 18

| Uncentrifuged BAL samples | | | | |
|---|---|---|---|---|
| | FXG PCR+ | FXG PCR− | | |
| *Aspergillus* culture+ | 5 | 12 | 17 | 29.41 Sensitivity |
| *Aspergillus* culture− | 3 | 75 | 77 | 96.15 Specificity |
| | 8 | 87 | 95 | 0 |
| | 62.50 PPV | 86.21 NPV | | |

The other respiratory samples tested included sputum, bronchial aspirations, endotracheal aspirations, lung aspirations, one pulmonary wound drainage and one nasal secretion. Most of the sputum samples were from cystic fibrosis patients. The volumes processed varied, and there is no centrifugation step in the processing of these usually small samples. The results are shown below for these 75 samples.

TABLE 19

| Sputum and non-BAL respiratory samples | | | | |
|---|---|---|---|---|
| | FXG PCR+ | FXG PCR− | | |
| *Aspergillus* culture+ | 15 | 4 | 19 | 78.95 Sensitivity |
| *Aspergillus* culture− | 7 | 49 | 56 | 87.50 Specificity |
| | 22 | 53 | 75 | |
| | 68.18 PPV | 92.45 NPV | | |

Compared with the centrifuged BAL samples, the sensitivity is similar at 79% versus 73%. Proportionately there slightly more assay positive, culture negative results with other respiratory samples than with BAL, leading to a slightly lower specificity 88% versus 96%, and lower PPV (68% versus 83%). These differences probably reflect many factors, such as sample volume and antifungal treatment.

TABLE 20

| All respiratory samples together (centrifuged BALs) | | | | |
|---|---|---|---|---|
| | FXG PCR+ | FXG PCR− | | |
| *Aspergillus* culture+ | 34 | 12 | 45 | 73.91 Sensitivity |
| *Aspergillus* culture− | 11 | 142 | 153 | 92.76 Specificity |
| | 45 | 153 | 198 | |
| | 75.56 PPV | 92.16 NPV | | |

Of the 198 respiratory samples analysed, 34 were both culture positive and assay positive, 142 were true negatives, with 11 false positive FXG PCR and 12 FXG PCR false negatives. This yields sensitivity and PPV values of 73.9% and 75.6% respectively and specificity and NPV values of 92.8% and 92.2% respectively. Of note, 3 BAL samples were culture positive for *Penicillium* spp., which is not distinguished from *Aspergillus* spp. by the assay. If these are recorded as true positives, the sensitivity rises to 75.5%, the specificity to 94.6% and the PPV and NPV to 82.2% and 92.2% respectively. Also of note two patients with zygomycosis caused by *Rhizopus* spp. were not detected by the assay, nor were eight samples from patients colonized by *Candida albicans,* nor one colonized by three species of *Paecilomyces* and *Candida tropicalis.* Six microscopy positive samples for non-septate hyphae (but culture negative) were negative in the assay.

There were 15 samples excluded from the analysis because the IAC was out of range. The proposed interpretation criteria in the IFU will allow positive results to be reported, even if inhibition is detected (i.e. a raised IAC Ct value). Among these 15 samples, 13 were both culture and assay negative and two were culture positive and assay negative. Therefore, it is not possible to confirm with this dataset that this interpretation is correct, and it will need confirmation in future studies.

There were 31 fresh lung tissue samples processed by the MycXtra™ extraction method (preceeded by proteinase K digestion) from Innsbruck. These were selected because they were generally positive samples from at risk patients, and no controls or negatives were processed alongside. Two analyses were done: one compared FXG PCR results with septate hyphae (all Aspergilli causing tissue invasive disease have septate hyphae, as do other less common invasive fungi such as *Scedosporium* spp. *Fusarium* spp., *Penicillium* spp. and others) and another compared with culture of *Aspergillus* spp. Both tables are shown below. Cultures were positive for *A. fumigatus* and *A. terreus*.

TABLE 21

Septate hyphae only

| | FXG PCR+ | FXG PCR− | | | |
|---|---|---|---|---|---|
| Histology+ | 14 | 9 | 23 | 60.87 | Sensitivity |
| Histology− | 0 | 7 | 7 | 100 | Specificity |
| | 14 | 16 | 30 | | |
| | 100 PPV | 43.75 NPV | | | |

TABLE 22

*Aspergillus* culture +ve

| | FXG PCR+ | FXG PCR− | | | |
|---|---|---|---|---|---|
| *Aspergillus* culture+ | 12 | 3 | 15 | 80.00 | Sensitivity |
| *Aspergillus* culture− | 2 | 14 | 16 | 87.5 | Specificity |
| | 14 | 17 | 31 | | |
| | 85.71 PPV | 82.35 NPV | | | |

The data show that the culture performance is better than the histology performance, principally because there are six more assay positive results compared to culture than to histology. This suggests, but does not confirm, that some septate hyphae seen are not Aspergilli. Overall the 100% PPV for the assay compared with histology is helpful clinically, combined with culture results, and the high sensitivity (80%) compared with culture is acceptable.

The vast majority of positive cultures were *A. fumigates* with rather fewer *A. terreus* positives and one *A. flavus* positive. The assay detected these three species, the most common pathogenic species (>98%). One *A. niger* and one *A. glaucus* isolate were cultured from samples and both were negative in the assay. In both cases they were mixed positive cultures, (*C. albicans* and *Rhizopus oryzae*). Neither was implicated in disease.

The real-time detection assay performed well for the rapid detection of *Pneumocystis jirovecii* and *Aspergillus* spp. in a large retrospective multicentre study. The data are consistent with high efficiency extraction of both fungal genera and detection limits of <10 fungal cells. *Pneumocystis* is an alveolar pathogen and is therefore present in large amounts in disease in the bronchi and small airways. Aspergilli usually cause parenchymal disease (invasive aspergillosis) in which small numbers of fungal cells are present in the airways, but also may colonise and infect the large airways, with large numbers of fungal cells present. The clinical performance data are consistent with these different pathologies, with a higher sensitivity demonstrable for *P. jirovecii* than *Aspergillus*. The specificity of the *Aspergillus* component of the assay is not absolute, and so additional fungi are detected. These are primarily fungi with a similar antifungal susceptibility profile to *Aspergillus*, with the single exception of *Fusarium* spp. which is not susceptible to the echinocandins or itraconazole. Test failure due to PCR inhibition was infrequent, and of uncertain cause, as the MycXtra™ kit removes many potential inhibitors, including inhaled drugs. For *Pneumocystis* (and by extension to *Aspergillus*) a positive result can be safely, even with an inhibitor present, whereas a negative one cannot. Additional data on a small number of lung biopsy specimens shows good performance, especially when compared to culture.

We claim:

1. A kit for testing for the presence or absence of an identifying region of fungal nucleic acid comprising SEQ ID NO: 14, the complement or transcript thereof, or a sequence having 80% or more sequence identity with SEQ ID NO: 14, the complement or transcript thereof, in a human clinical sample comprising a molecular beacon probe comprising SEQ ID NO: 17 and a pair of primers comprising SEQ ID NO: 15 and SEQ ID NO: 16.

2. The kit of claim 1 further comprising one or more internal PCR amplification controls.

* * * * *

SEQUENCE LISTING

<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
tcgattccgg agagggagc                                                  19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
gccctatcaa ctttcgatgg                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
gccttccttg gatgtggtag                                              20

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
cgcgattcga ttccggagag ggagcatcgc g                                 31

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
gatgattcat aataactttt cg                                           22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
tagataaaaa atcaatgcct tcgg                                         24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
catggtaggc cactatccta c                                            21

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
cgcgatgatg attcataata acttttcgat cgcg                              34

-continued

```
<210> SEQ ID NO 9
<211> LENGTH: 640
<212> TYPE: DNA
<213> ORGANISM: Zea mays

<400> SEQUENCE: 9
taatgaattc aatgattcaa aaaaaactaa gagatggatt aaattataca aggaatcctg      60
gtttcaaaga aaagtaaaat ggggatatgg cgaaatcggt agacgctacg gacttgattg     120
tattgagcct tggtatggaa acctgctaag tggtaacttc caaattcaga gaaaccctgg     180
aatgaaaaat gggcaatcct gagccaaatc cctttttttga aaaacaagtg gttctcaaac    240
tagaacccaa aggaaaagga taggtgcaga gactcaatgg aagctgttct aacgaatcga     300
agtaataacg attaatcaca gaacccatat tataatatag gttctttatt ttattttttag    360 aatgaaatta ggaatgatta tgaaatagaa aattcataat tttttttttag aattattgtg    420 aatctattcc aatcaaatat tgagtaatca aatccttcaa ttcattgttt tcgagatctt     480
ttaattttaa aaagtggatt aatcggacga ggataaagag agagtcccat tctacatgtc     540
aatactgaca acaatgaaat ttctagtaaa aggaaaatcc gtcgacttta taagtcgtga     600
gggttcaagt ccctctatcc ccaaaccctc ttttattccc                           640

<210> SEQ ID NO 10
<211> LENGTH: 20
<212> TYPE: DNA
<213> ORGANISM: Zea mays

<400> SEQUENCE: 10
caatcctgag ccaaatccct                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
cctgctaagt ggtaacttcc                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
tgagtctctg cacctatcct                                                  20

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
cgcacgcaat cctgagccaa atccctcgtg cg                                    32
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
agttgaacct tgggtctggc                                                    20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
ggtaattcca gctccaatag c                                                  21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 16
ggcctgcttt gaacactcta a                                                  21

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
cgcgatagtt gaaccttggg tctggcatcg cg                                      32

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 18
ctaggatata gctggttttc tgc                                                23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
gcaaagtact cagaagaatt gtgg                                               24

<210> SEQ ID NO 20

```
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
tccctcgaga tattcagtgc                                                20

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
cgcagcctag gatatagctg gttttctgcg ctgcg                               35

<210> SEQ ID NO 22
<211> LENGTH: 521
<212> TYPE: DNA
<213> ORGANISM: Candida tropicalis

<400> SEQUENCE: 22
accttaacga ggaacaattg gagggcaagt ctggtgccag cagccgcggt aattccagct    60
ccaaaagcgt atattaaagt tgttgcagtt aaaaagcttc gtagttgaac cttgggcttg   120
gttggccggt cccatctttc tgatgcgtac tggaacccaa ccgaagcctt tccttctggc   180
tagccttttg gcgaacccag gactttact ttgaaaaaat tagagtgttc aaagcaggcc    240
tttgctcgaa tatattagca tggaataata gaataggacg ttatggttct attttgttgg   300
tttctaggac catcgtaatg attaataggg accggtcggg ggtatcagta ttcagttgtc   360
agaggtgaaa ttcttggatt tactgaagac taactactgc gaaaagcatt taccaaggac   420
gttttgcatt aatcaagaac gaaagttagg ggatcgaaga tgatcagata ccgtcgtagt   480
cttaaccata aactatgccg actagggatc ggttgttgtt c                      521

<210> SEQ ID NO 23
<211> LENGTH: 515
<212> TYPE: DNA
<213> ORGANISM: Candida parapsilosis

<400> SEQUENCE: 23
accttaacga ggaacaattg gagggcaagt ctggtgccag cagccgcggt aattccagct    60
ccaaaagcgt atattaaagt tgttgcagtt aaaaagctcg tagttgaacc ttgggcttgg   120
ttggccggtc catctttttt gatgcgtact ggacccagcc gagccttttcc ttctggctag   180 ccttttggc gaaccaggac ttttacttttg aaaaaattag agtgttcaaa gcaggccttt   240
gctcgaatat attagcatgg aataatagaa taggacgtta tggttctatt tgttggtttt   300
ctaggaccat cgtaatgatt aatagggacg tcggggggta tcagtattca gttgtcagag   360
gtgaaattct tggatttact gaagactaac tactgcgaaa gcatttacca aggacgtttt   420
cattaatcaa gaacgaaagt taggggatcg aagatgatca gataccgtcg tagtcttaac   480
cataaactat gccgactagg gatcggttgt tgttc                             515

<210> SEQ ID NO 24
<211> LENGTH: 513
```

<212> TYPE: DNA
<213> ORGANISM: Candida dubliniensis

<400> SEQUENCE: 24

```
accttaacga ggaacaattg gagggcaagt ctggtgccag cagccgcggt aattccagct    60
ccaaaagcgt atattaaagt tgttgcagtt aaaaagctcg tagttgaacc ttgggcttgg   120
ctggccggtc catcttttg atgcgtatgg acccagccga gcctttcttc tggctagcca   180
tttatggcga accaggactt ttactttgaa aaaattagag tgttcaaagc aggcctttgc   240
tcgaatatat tagcatggaa taatagaata ggacgttatg gttctatttt gttggtttct   300
aggaccatcg taatgattaa tagggacggt cgggggtatc agtattcagt tgtcagaggt   360
gaaattcttg gatttactga agactaacta ctgcgaaagc atttaccaag gacgttttca   420
ttaatcaaga acgaaagtta ggggatcgaa gatgatcaga taccgtcgta gtcttaacca   480
taaactatgc cgactaggga tcggttgttg ttc                                513
```

<210> SEQ ID NO 25
<211> LENGTH: 515
<212> TYPE: DNA
<213> ORGANISM: Candida albicans

<400> SEQUENCE: 25

```
accttaacga ggaacaattg gagggcaagt ctggtgccag cagccgcggt aattccagct    60
ccaaaagcgt atattaaagt tgttgcagtt aaaaagctcg tagttgaacc ttgggcttgg   120
ctggccggtc catcttttg atgcgtactg gacccagccg agcctttcct tctgggtagc   180
catttatggc gaaccaggac ttttactttg aaaaaattag agtgttcaaa gcaggccttt   240
gctcgaatat attagcatgg aataatagaa taggacgtta tggttctatt tgttggttt   300
ctaggaccat cgtaatgatt aatagggacg tcgggggta tcagtattca gttgtcagag   360
gtgaaattct tggatttact gaagactaac tactgcgaaa gcatttacca aggacgtttt   420
cattaatcaa gaacgaaagt taggggatcg aagatgatca gataccgtcg tagtcttaac   480
cataaactat gccgactagg gatcggttgt tgttc                              515
```

<210> SEQ ID NO 26
<211> LENGTH: 529
<212> TYPE: DNA
<213> ORGANISM: Candida guilliermondii

<400> SEQUENCE: 26

```
accttaacga ggaacaattg gagggcaagt ctggtgccag cagccgcggt aattccagct    60
ccaatagcgt atattaaagt tgttgcagtt aaaaagctcg tagttgaact ttgggcttgg   120
ttggccggtc cgccttttg gcgagtactg gacccaaccg agcctttcct tctggctaac   180
cattcgccct tgtggtgttt ggcgaaccag gacttttact ttgaaaaaat tagagtgttc   240
aaagcaggcc tttgctcgaa tatattagca tggaataata gataggacg ttatggttct   300
attttgttgg tttctaggac catcgtaatg attaataggg acggtcgggg gcatcagtat   360
tcagttgtca gaggtgaaat tcttagattt actgaagact aactactgcg aaagcatttg   420
ccaaggacgt tttcattaat caagaacgaa agttagggga tcgaagatga tcagataccg   480
tcgtagtctt aacccataaa ctatgccgac tagggatcgg tgttgttc                529
```

<210> SEQ ID NO 27
<211> LENGTH: 508
<212> TYPE: DNA

<213> ORGANISM: Candida lusitaniae

<400> SEQUENCE: 27

| | | |
|---|---|---|
| accttaacga ggaacaattg agggcaagt ctggtgccag cagccgcggt aattccagct | 60 |
| ccaagagcgt atattaaagt tgttgcagtt aaaaagctcg tagttgaacc ttggaggcgc | 120 |
| cgtgccggtc cgcttaggcg agcactggag gcggcgcctc tttccctcct cctcttagca | 180 |
| ataagaggag gactgttact ttgagtaaat gagagtgttc aaagcaggcg cacgcttgaa | 240 |
| tctgttagca tggaataata gaataggacg catggttcta ttttgttggt ttctaggacc | 300 |
| catcgtaatg attaataggg acggtcgggg gcatcagtat tcagttgtca gaggtgaaat | 360 |
| tcttggattt actgaagact aactactgcg aaagcatttg ccaaggacgt tttcattaat | 420 |
| caagaacgaa agttagggga tcgaagatga tcagataccg tcgtagtctt aaccataaac | 480 |
| tatgccgact agggatcggg cggcgttc | 508 |

<210> SEQ ID NO 28
<211> LENGTH: 528
<212> TYPE: DNA
<213> ORGANISM: Candida glabrata

<400> SEQUENCE: 28

| | | |
|---|---|---|
| accttaacga ggaacaattg agggcaagt ctggtgccag cagccgcggt aattccagct | 60 |
| ccaatagcgt atattaaagt tgttgcagtt aaaaagctcg tagttgaact ttgggcctgg | 120 |
| gtggccggtc cgatttttc gtgtactgga atgcacccgg gcctttcctt ctggctaacc | 180 |
| ccaagtcctt gtggcttggc ggcgaaccag gactttact ttgaaaaaat tagagtgttc | 240 |
| aaagcaggcg tattgctcga atatattagc atggaataat ggaataggac gtttggttct | 300 |
| attttgttgg tttctaggac catcgtaatg attaataggg acggtcgggg gcatcagtat | 360 |
| tcaattgtca gaggtgaaat tcttggattt attgaagact aactactgcg aaagcatttg | 420 |
| ccaaggacgt tttcattaat caagaacgaa agttagggga tcgaagatga tcagataccg | 480 |
| tcgtagtctt aaccataaac tatgccgact agggatcggg tggtgttt | 528 |

<210> SEQ ID NO 29
<211> LENGTH: 509
<212> TYPE: DNA
<213> ORGANISM: Candida krusei

<400> SEQUENCE: 29

| | | |
|---|---|---|
| accttaacga ggaacaattg agggcaagt ctggtgccag cagccgcggt aattccagct | 60 |
| ccaatagcgt atattaaagt tgttgcagtt aaaaagctcg tagttgaact ttgggcctgg | 120 |
| gcggacggtc tacctatggt aagcactgtt gcggccgggt ctttccttct ggctagccct | 180 |
| cgggcgaacc aggacgatta ctttgaggaa attagagtgt caaagcagg cctttgctcg | 240 |
| gatatattag catggaataa tagaatagga cgcatggttc tattttgttg gtttctagga | 300 |
| ccatcgtaat gattaatagg gacggtcggg ggcatcagta ttcagtcgtc agaggtgaaa | 360 |
| ttcttggatt gactgaagac taactactgc gaaagcattt gccaaggacg ttttcattaa | 420 |
| tcaagaacga aagttagggg atcgaagatg atcagatacc gtcgtagtct taaccataaa | 480 |
| ctatgccgac tagggatcgg gtggtgcta | 509 |

<210> SEQ ID NO 30
<211> LENGTH: 20
<212> TYPE: DNA
<213> ORGANISM: Artificial Sequence

```
<220> FEATURE:
<223> OTHER INFORMATION: Description of Artificial Sequence: Synthetic
      Oligonucleotide

<400> SEQUENCE: 30 cctttttggcg aacccaggac                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
attggagggc aagtctggtg                                                     20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32
ccgatcccta gtcggcatag                                                     20

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33
cgcagccctt ttggcgaacc caggacgctg cg                                       32

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 34
tctggctagc ctttttggcg                                                     20

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 35
cggacgtctg gctagccttt ttggcgcgtc cg                                       32

<210> SEQ ID NO 36
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      Oligonucleotide

<400> SEQUENCE: 36
ttctgggtag ccatttatgg                                                    20

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 37
cggacgttct gggtagccat ttatggcgtc cg                                      32

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 38
gctaacccca agtccttgtg                                                    20

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 39
cggacggcta accccaagtc cttgtgcgtc cg                                      32

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 40
tcgggcgaac caggacgatt                                                    20

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 41
gcagttaaaa agctcgtagt tgaac                                              25

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
```

Oligonucleotide

<400> SEQUENCE: 42
aaaggcctgc tttgaacact ct                                              22

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 43
cgcagctcgg gcgaaccagg acgattgctg cg                                   32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 44
ccgtggctgc ggcttaattt gactcaccac gg                                   32

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 45
cgcgacacat ccaaggaagg cagcaggtcg cg                                   32

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 46
taattccagc tccaatagcg                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 47
ccagaaggaa aggtccagcc                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 48
aattgacgga agggcaccac                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 49
tgtctggacc tggtgagttt                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 50
agagggagcc tgagaaacgg                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 51
cggctgctgg caccagactt                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 52
ctgcggctta atttgactca                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 53
acatccaagg aaggcagcag                                               20
```